United States Patent [19]
Baker et al.

[11] Patent Number: 5,291,535
[45] Date of Patent: * Mar. 1, 1994

[54] METHOD AND APPARATUS FOR DETECTING EXCESS/INSUFFICIENT SOLDER DEFECTS

[75] Inventors: Bruce D. Baker, Olivenhain; Robert L. Corey, San Diego; John A. Adams; Edward W. Ross, both of Escondido, all of Calif.

[73] Assignee: Four Pi Systems Corporation, San Diego, Calif.

[*] Notice: The portion of the term of this patent subsequent to May 15, 2007 has been disclaimed.

[21] Appl. No.: 740,631

[22] Filed: Aug. 5, 1991

Related U.S. Application Data

[63] Continuation-in-part of Ser. No. 479,092, Feb. 12, 1990, Pat. No. 5,097,492, which is a continuation of Ser. No. 115,171, Oct. 30, 1987, Pat. No. 4,926,452.

[51] Int. Cl.$^5$ ............................................. G01N 23/04
[52] U.S. Cl. ...................................... 378/22; 378/207; 378/62
[58] Field of Search ........................ 378/22, 62, 207, 4; 358/111

[56] References Cited

U.S. PATENT DOCUMENTS

| | | | |
|---|---|---|---|
| 4,481,664 | 11/1984 | Linger et al. | 356/394 |
| 4,561,104 | 12/1985 | Martin | 382/8 |
| 4,575,751 | 3/1986 | Duschl | 382/8 |
| 4,628,531 | 12/1986 | Okamoto et al. | 382/34 |
| 4,677,473 | 6/1987 | Okamoto et al. | 382/34 |
| 4,688,939 | 8/1987 | Ray | 258/572 |
| 4,731,855 | 3/1988 | Suda et al. | 382/8 |
| 4,803,639 | 2/1989 | Steele et al. | 378/58 |
| 4,809,308 | 2/1989 | Adams et al. | 378/58 |
| 4,852,131 | 7/1989 | Armistead | 378/58 |
| 4,926,452 | 5/1990 | Baker et al. | 378/22 |
| 5,097,492 | 3/1992 | Baker et al. | 378/22 |

FOREIGN PATENT DOCUMENTS

| | | |
|---|---|---|
| 143290 | 11/1979 | Japan . |
| 161551 | 8/1985 | Japan . |

OTHER PUBLICATIONS

Hasenkamp, "Radiographic Laminography", *Materials Evaluation*, Aug. 1974, pp. 169–180.

Moler, "Development of a Continuous Scanning Laminograph", Final Report No. IITRI V6034-24, Oct. 1968.

Blanche, "Nondestructive Testing Techniques for Multilayer Printed Wiring Boards", Nondestructive Testing: Trends and Technique, NASA SP-5082, Oct. 1986, pp. 1–13.

(List continued on next page.)

*Primary Examiner*—David P. Porta
*Assistant Examiner*—Don Wong
*Attorney, Agent, or Firm*—Dennis H. Epperson

[57] ABSTRACT

A method and apparatus for the detection of excess or insufficient solder conditions at electrical connections on printed circuit boards are disclosed. The invention analyzes a cross-sectional image of an electrical connection to obtain the average solder thickness of the connection. This average solder thickness is then compared to an upper threshold value to determine if the connection is an excess solder defect, and a lower threshold value to determine if the connection is an insufficient solder defect. In one embodiment, the present invention compensates for variations in image intensity due to the background by employing a first and second correction factor in the calibration technique. The first correction factor is the measured background gray scale value local to the connection, while the second correction factor is determined to have a substantially linear relationship to the background image intensity local to each solder connection. The present invention further includes a process control feedback system which detects and compensates for trends in the solder application process. This helps to insure that defective solder joints are avoided before they are produced. In one embodiment, the process control feedback system is fully automated.

31 Claims, 41 Drawing Sheets

OTHER PUBLICATIONS

Hamre, "Nondestructive Testing Techniques for Multilayer Printed Wiring Boards", Report No. IITRI-E60-24-15, Sep. 1965.

Soron, IRT Corp., "X-Ray Inspection Meets Increased PWB Throughput", Density Challenge—Part 1, *Electronics*, Oct. 1987, pp. 36-37.

Pound, "Image Processing Boosts the Power of Non-destructive Testing", *Electronic Packaging and Production*, Jun. 1985.

Casey, "X-Ray Inspection", *Manufacturing Systems*, Jul. 1987, p. 18ff.

Phelps, Christi, "Four Pi Captures Contract, Capital; Unveils Product", *San Diego Business Journal*, Week of Oct. 10-16, 1988.

Stanley et al., "A New NDE Capability for Thin-Shelled Structures", AFWAL-TR-84-4120, Materials Lab, Wright Patterson AFB, Sep., 1984.

Deane et al., IRT Corp., "Using X-Ray Vision to Verify SMD-Board Quality," *Electronics Test*, Feb., 1987, pp. 32-35.

Corey, IRT Corp., "Artificial Perception Gives Super Vision", *Research and Development*, Oct., 1984.

LaClair, "Nondestructive Measurement and Inspection Process", IBM Technical Disclosure Bulletin, vol. 18, No. 12, May, 1976.

Hufault et al., "Lead-Indium Solder Joint Analysis", IBM Technical Disclosure Bulletin, vol. 19, No. 11, Apr., 1977.

Wittenberg, "IRT Improves SMT X-Ray Inspection System", *Electronic Engineering Times*, Oct. 5, 1987, p.53.

Four Pi Systems product brochure for "3DX Series 2000" Automated Inspection System, Copyright 1988.

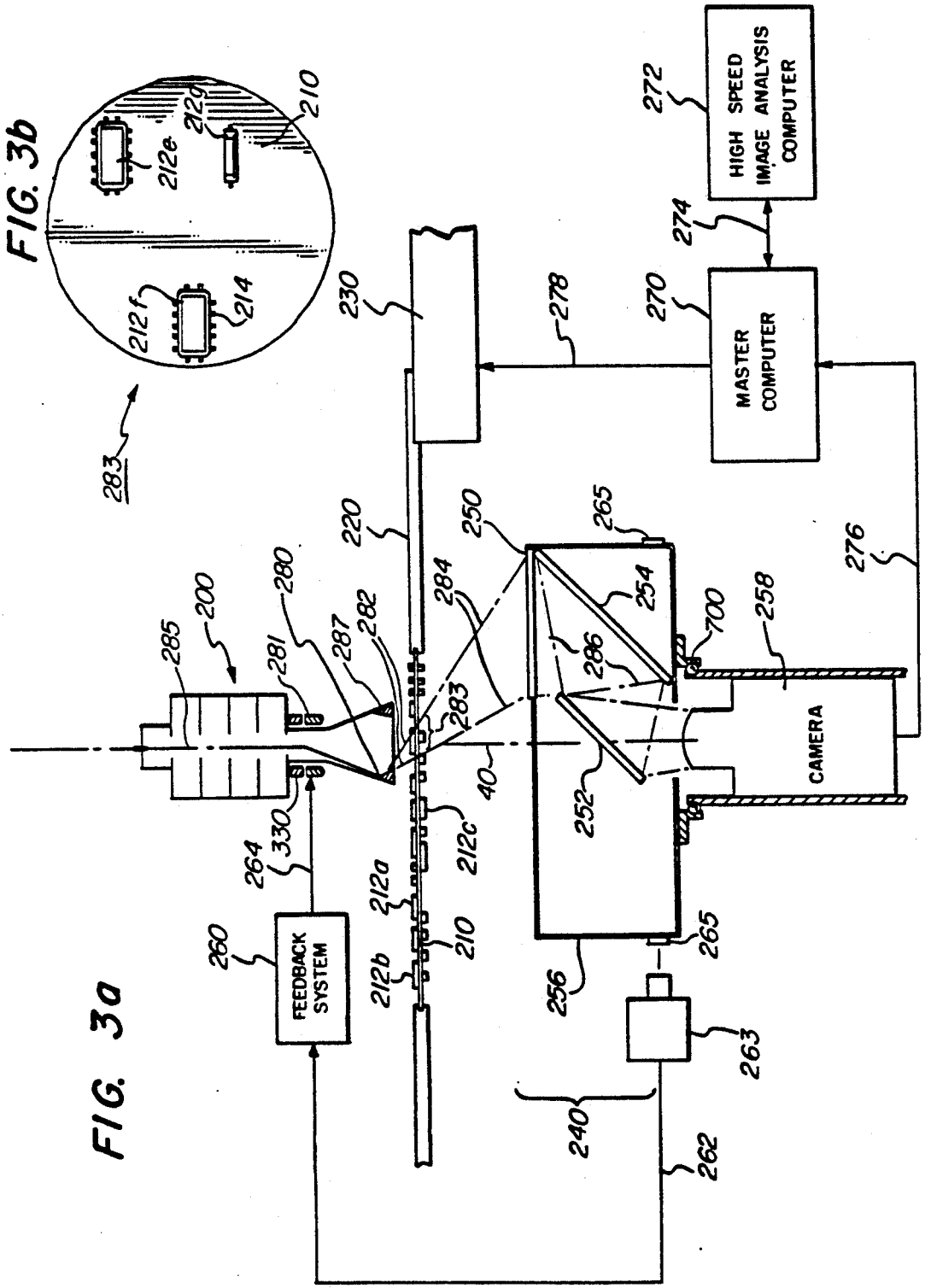

FIG. 27
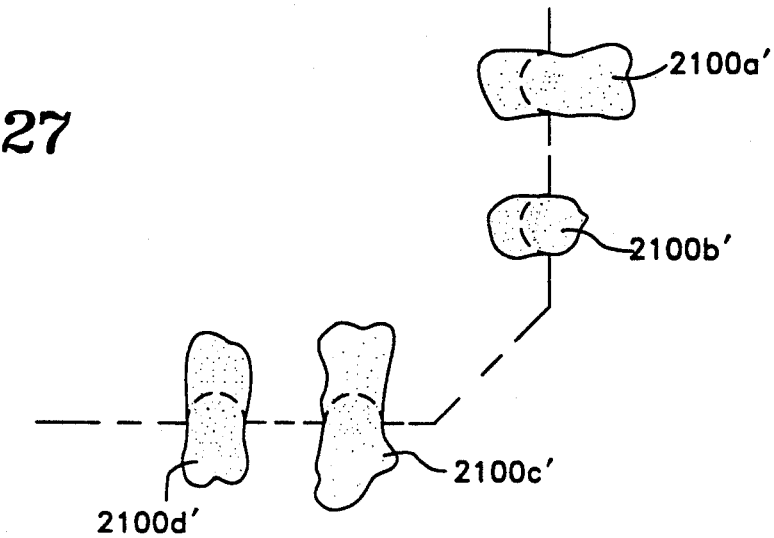
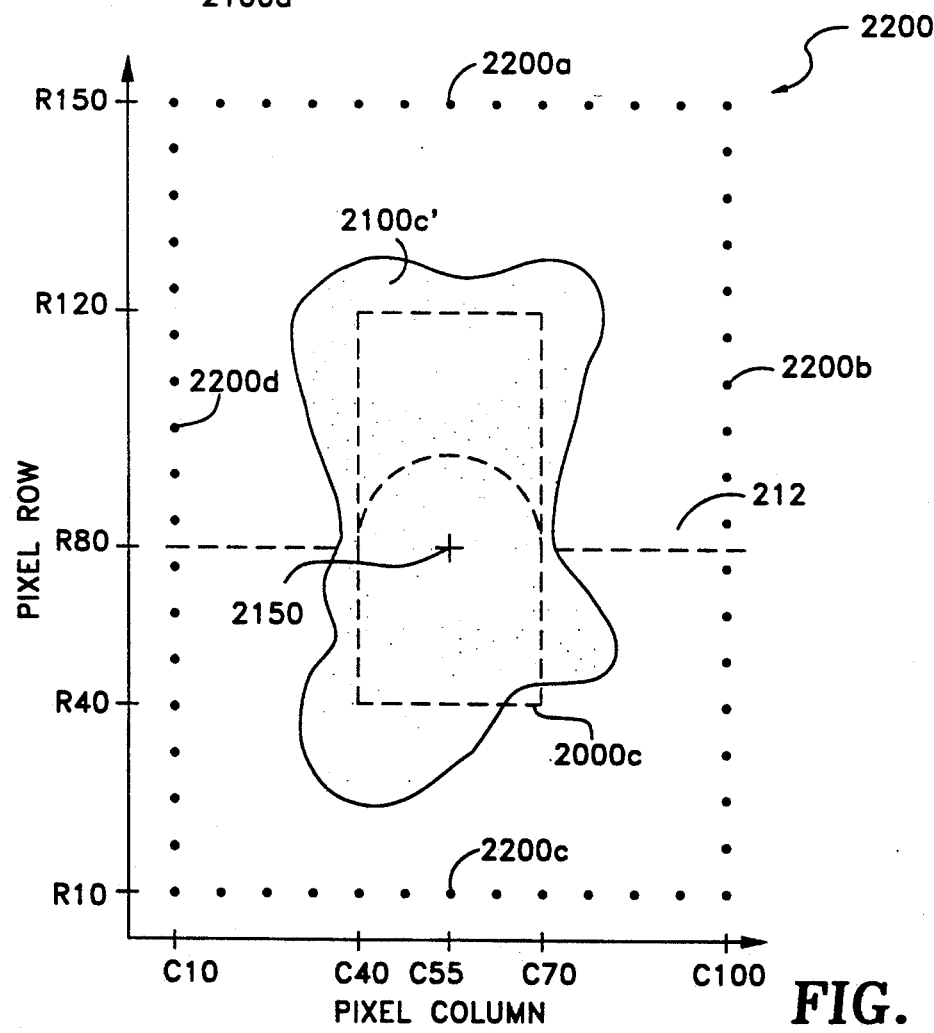
FIG. 28

TUNGSTEN STEP WEDGE
AT THREE PLACES (BKG SUBTRACTED)

FOREGROUND VS. BACKGROUND GRAY LEVEL

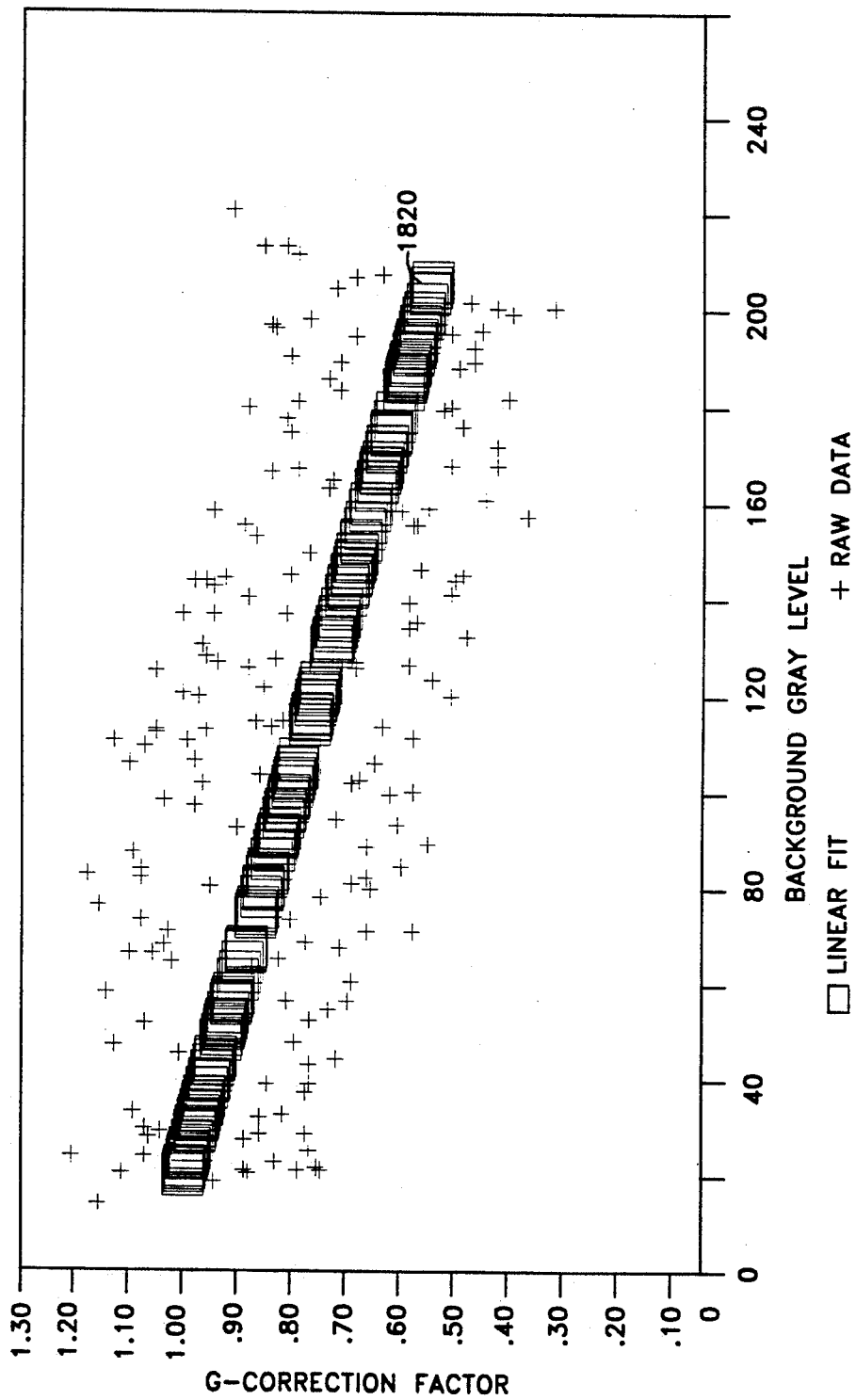

METHOD AND APPARATUS FOR DETECTING EXCESS/INSUFFICIENT SOLDER DEFECTS

RELATED APPLICATIONS

This application is a continuation-in-part of patent application Ser. No. 479,092, filed Feb. 12, 1990, inventors Baker et al., and entitled "Automated Laminography System for Inspection of Electronics"; now U.S. Pat. No. 5,097,492 which is a continuation of application Ser. No. 115,171, filed Oct. 30, 1987, inventors Baker et al., entitled "Automated Laminography System for Inspection of Electronics", which issued on May 15, 1990 as U.S. Pat. No. 4,926,452.

FIELD OF THE INVENTION

The invention relates generally to the inspection of circuit boards using a computerized laminography system for rapid, high resolution inspection of manufactured electronic items, especially to the inspection of a circuit board for excess or insufficient solder defects.

BACKGROUND OF THE INVENTION

Rapid and precise quality control inspections of the soldering and assembly of electronic devices have become priority items in the electronics manufacturing industry. The reduced size of components and solder connections, the resulting increased density of components on circuit boards and the advent of surface mount technology (SMT), which places solder connections underneath device packages where they are hidden from view, have made rapid and precise inspections of electronic devices and the electrical connections between devices very difficult to perform in a manufacturing environment.

Many existing inspection systems for electronic devices and connections make use of penetrating radiation to form images which exhibit features representative of the internal structure of the devices and connections. These systems often utilize conventional radiographic techniques wherein the penetrating radiation comprises X-rays. Medical X-ray pictures of various parts of the human body, e.g., the chest, arms, legs, spine, etc., are perhaps the most familiar examples of conventional radiographic images. The images or pictures formed represent the X-ray shadow cast by an object being inspected when it is illuminated by a beam of X-rays. The X-ray shadow is detected and recorded by an X-ray sensitive material such as film or other suitable means.

The appearance of the X-ray shadow or radiograph is determined not only by the internal structural characteristics of the object, but also by the direction from which the incident X-rays strike the object. Therefore, a complete interpretation and analysis of X-ray shadow images, whether performed visually by a person or numerically by a computer, often requires that certain assumptions be made regarding the characteristics of the object and its orientation with respect to the X-ray beam. For example, it is often necessary to make specific assumptions regarding the shape, internal structure, etc. of the object and the direction of the incident X-rays upon the object. Based on these assumptions, features of the X-ray image may be analyzed to determine the location, size, shape, etc., of the corresponding structural characteristic of the object, e.g., a defect in a solder connection, which produced the image feature. These assumptions often create ambiguities which degrade the reliability of the interpretation of the images and the decisions based upon the analysis of the X-ray shadow images. One of the primary ambiguities resulting from the use of such assumptions in the analysis of conventional radiographs is that small variations of a structural characteristic within an object, such as the shape, density and size of a defect within a solder connection, are often masked by the overshadowing mass of the solder connection itself as well as by neighboring solder connections, electronic devices, circuit boards and other objects. Since the overshadowing mass and neighboring objects are usually different for each solder joint, it is extremely cumbersome and often nearly impossible to make enough assumptions to precisely determine shapes, sizes and locations of solder defects within individual solder joints.

In an attempt to compensate for these shortcomings, some systems incorporate the capability of viewing the object from a plurality of angles. The additional views enable these systems to partially resolve the ambiguities present in the X-ray shadow projection images. However, utilization of multiple viewing angles necessitates a complicated mechanical handling system, often requiring as many as five independent, non-orthogonal axes of motion. This degree of mechanical complication leads to increased expense, increased size and weight, longer inspection times, reduced throughput, impaired positioning precision due to the mechanical complications, and calibration and computer control complications due to the non-orthogonality of the axes of motion.

Many of the problems associated with the conventional radiography techniques discussed above may be alleviated by producing cross-sectional images of the object being inspected. Tomographic techniques such as laminography and computed tomography (CT) are often used in medical applications to produce cross-sectional or body section images. In medical applications, these techniques have met with widespread success, largely because relatively low resolution on the order of one or two millimeters (0.04 to 0.08 inches) is satisfactory and because speed and throughput requirements are not as severe as the corresponding industrial requirements. However, no laminography inspection system has yet met with commercial success in an industrial application because of shortcomings in precision and/or speed of inspection. This is because existing laminography systems have been incapable of achieving the high positional accuracies and image resolutions necessary to solve industrial inspection problems while operating at the speeds necessary to make them practical in a production environment.

In the case of electronics inspection, and more particularly, for inspection of electrical connections such as solder joints, image resolution on the order of several micrometers, for example, 20 micrometers (0.0008 inches) is necessary. Furthermore, an industrial solder joint inspection system must generate multiple images per second in order to be practical for use on an industrial production line. Heretofore, laminography systems have not been able to achieve these speed and accuracy requirements necessary for electronics inspection.

Laminography systems for the production of cross-sectional images have taken several forms. One system is described in U.S. Pat. No. 3,928,769 entitled "LAMINOGRAPHIC INSTRUMENT." The radiation source and the detector described therein are mechanically coupled to achieve the required geometry and synchronized motion of the source and detector. This type of system has the disadvantage of having to move the relatively high mass of some combination of high mass elements including the radiation source, object under inspection and detector. This becomes especially difficult when X-ray tubes and camera equipment are to be used. The speed of this system is severely restricted due to the fact that it is extremely difficult to move these relatively large masses rapidly and precisely. This system also has limitations on the resolution that can be obtained due to the imprecision and degradation over time of the many complicated moving parts.

In another system described in U.S. Pat. No. 4,211,927 entitled "COMPUTERIZED TOMOGRAPHY SYSTEM," the mechanical motions of the radiation source and detector are electronically driven by separate stepper motors whose timing is controlled by the same computer. The motion of each component is referenced to a respective predetermined central calibration location. Thus, even though the source and detector are driven by the same computer, there is no direct link correlating the position of the source with the position of the detector. The performance of this system is also limited by the speed at which the massive radiation source and detector can be oscillated and by the precision, synchronization and stability of the moving parts.

In U.S. Pat. No. 4,516,252 entitled "DEVICE FOR IMAGING LAYERS OF A BODY," a plurality of radiation sources, each fixed in space at a different location, is used in lieu of a single oscillating source. The location of an image detector is moved electronically in synchronization with the activation of the plural sources. While this approach eliminates the problems inherent with mechanically moving the radiation source and detector, it entails the disadvantage in cost of requiring multiple radiation sources. The resulting image quality is also degraded because the desired blurring of out of focus features is not continuous, but rather discretized, due to the finite number of radiation source positions. Thus, unwanted features remain in the image as a plurality of distinct artifacts.

U.S. Pat. No. 2,667,585 entitled "DEVICE FOR PRODUCING SCREENING IMAGES OF BODY SECTIONS" shows a stationary X-ray tube with the radiation source motion provided by electrostatic deflection of the electron beam in the X-ray tube, thus causing the electron beam to trace a path over the surface area of a flat target anode. Opposite the X-ray tube is a detector image tube containing electron optics which deflect the resulting electron image onto a stationary detector. The deflection circuit of the X-ray tube and the deflection circuit of the image tube are driven from the same voltage supply so as to simultaneously drive the motion of the X-ray source and the deflection of the resultant image in the detector. This system thus avoids many of the disadvantages associated with mechanically moving the radiation source and detector. However, this system has no provision for consistently maintaining the focus and energy of the electron beam as the beam is swept over the target surface. This causes the X-ray spot to vary in both size and intensity, which seriously limits the resolution achievable with the device. The use of electron optics to deflect the electron image also limits the detection resolution achievable with this device. This problem becomes especially severe as the image is deflected through large angles. Similarly, accuracy in the positioning of the X-ray spot is lost as the beam is deflected through severe angles. These characteristics substantially limit the resolution achievable with this technique. Furthermore, the technique is practical only for operation within a relatively small range of viewing angles, which limits the desired laminographic blurring effect of unwanted features and consequently limits the resolution in a direction normal to the plane of focus.

All of the above described laminography systems are directed to performing body section radiography and, as such, are not designed to produce high resolution images in rapid succession. Furthermore, such systems need not operate in a continuous duty cycle nor in an environment compatible with the manufacturing of electronics.

Many of the deficiencies found in presently used electronic inspection systems could be overcome with a high resolution, high speed laminographic inspection system. Such a system would be particularly well suited for the inspection of electrical connections such as solder joints in electronic assemblies. A high resolution laminograph of a solder joint should be capable of unambiguously revealing features in the solder joint which are indicative of the joint quality. Unfortunately, even though many attempts have been made to utilize laminographic techniques in industrial inspection environments, prior systems have consistently fallen short of optimum performance because of poor image resolution or prohibitively long inspection times, or both. Techniques previously used to improve resolution invariably resulted in long inspection times. Likewise, techniques previously used to decrease inspection time have generally sacrificed image resolution. A need thus exists for a high speed, high resolution industrial laminography system capable of inspecting electronics in industrial environments.

A particular type of solder defect is the deposition of too much solder on a connection pad, known as an excess solder defect, and the deposition of too little solder on a connection pad, known as an insufficient solder defect. Excess solder may result in the presence of solder on portions of the circuit board, the component, or the conductive pad regions, where solder is unnecessary or even detrimental to performance of the connection. Insufficient solder may result in poor fillet quality and may not provide sufficient strength to the connection between conductive pads of a component and circuit board. Thus, it is desirable to provide a procedure for detecting excess/insufficient solder defects which utilizes the advantages provided by laminographic circuit board inspection techniques.

In the past, methods for detecting excess/insufficient solder defects have been unduly complex, and many of these methods have been based on unreliable assumptions which lead to misleading measurements. In addition to this, some systems require that multiple procedures for detecting excess/insufficient solder defects be used. For example, in one prior system, separate procedures are used to detect excess solder on the bottom lead of a through-hole joint, excess solder on the top lead of a through-hole joint, and excess solder on the contact pad of a surface mount solder joint.

One obstacle with detecting excess/insufficient solder defects is that, with prior circuit board inspection systems, it is difficult to obtain an accurate measurement of the solder thickness of some types of solder joints. Thus, some systems attempt to determine solder thickness by indirect means such as measuring the angle at which solder bulges from a solder joint. One prior device takes multiple X-ray images of the same solder joint from different levels and angles in order to obtain information relating to the characteristics of the solder joint. Unfortunately, this technique is time consuming due to the multiple images which must be processed for each inspected solder joint. Also, each view requires that many different procedures be used for determining the characteristics of the solder connection. Thus, there also exists a need for a high resolution circuit board inspection device which can simply and accurately determine the characteristics of solder joints on a circuit board in a short time period.

SUMMARY OF THE INVENTION

The present invention is directed to a method and apparatus for the detection of excess or insufficient solder defects at electrical connections between electronic components which are mounted on printed circuit boards. The invention analyzes a cross-sectional image of an electrical connection by first obtaining the positional data which indicates the location and dimensions of the connection to be analyzed. The method further includes the step of defining a region of interest within the image region of the connection. The gray scale value of the background image local to the image of the connection is calibrated out, and then the average gray scale value is calculated within the region of interest. The calibrated average gray scale within the region of interest is then converted to solder thickness to obtain the average solder thickness within the region of interest. This average solder thickness is then compared to an upper threshold value to determine if the connection is an excess solder defect, and a lower threshold value to determine if the connection is an insufficient solder defect.

In one embodiment, the present invention compensates for variations in image intensity due to the background by employing a first and second correction factor in the calibration technique. The first correction factor is simply the measured background gray scale value local to the connection, while the second correction factor is determined to have a substantially linear relationship to the background image intensity local to each solder connection. By sampling the image intensities of solder connections of like thicknesses on different parts of a circuit board having different background levels, this linear relationship can be determined.

The present invention further includes a process control feedback system which detects and compensates for trends in the solder application process. For example, if an upward trend in solder thickness is detected, the process control feedback system would send a signal to the solder application device to reduce the amount of solder deposited on the contact pads. This helps to insure that defective solder joints are avoided before they are produced. In one embodiment, the process control feedback system is fully automated, although it is possible to implement the process control system manually, or in a semi-automated fashion.

BRIEF DESCRIPTION OF THE DRAWINGS

FIG. 2e shows a conventional, two-dimensional X-ray projection image of the object in FIG. 2a.

FIG. 3a is a diagrammatic cross-sectional view of a first preferred embodiment of the image forming apparatus used in accordance with the invention, showing how the laminographic image is formed and viewed by a camera.

FIG. 3b shows a top view enlargement of an inspection region shown in FIG. 3a.

FIG. 3c is a perspective view of the embodiment of the laminographic apparatus used in accordance with the invention shown in FIG. 3a.

FIG. 9b shows an X-ray image of the test fixture of FIG. 9a.

FIG. 10b is a continuation of the flowchart in FIG. 10a.

FIG. 20b is a continuation of the flowchart in FIG. 20a.

FIGS. 25a–25e the means by which a doughnut operator can be used to detect the centroid of a contact pad.

FIG. 27 is a cross-sectional view of the Leadless Chip Carrier connections shown in FIG. 26.

FIG. 28 is an enlarged cross-sectional view showing in greater detail the excess solder connection of FIG. 27.

FIG. 45 is a graph which plots the G-correction factor versus various background gray levels.

DETAILED DESCRIPTION OF THE PREFERRED EMBODIMENT

As used throughout, the term "radiation" refers to electromagnetic radiation, including but not limited to the X-ray, gamma and ultraviolet portions of the electromagnetic radiation spectrum.

Figure 1:
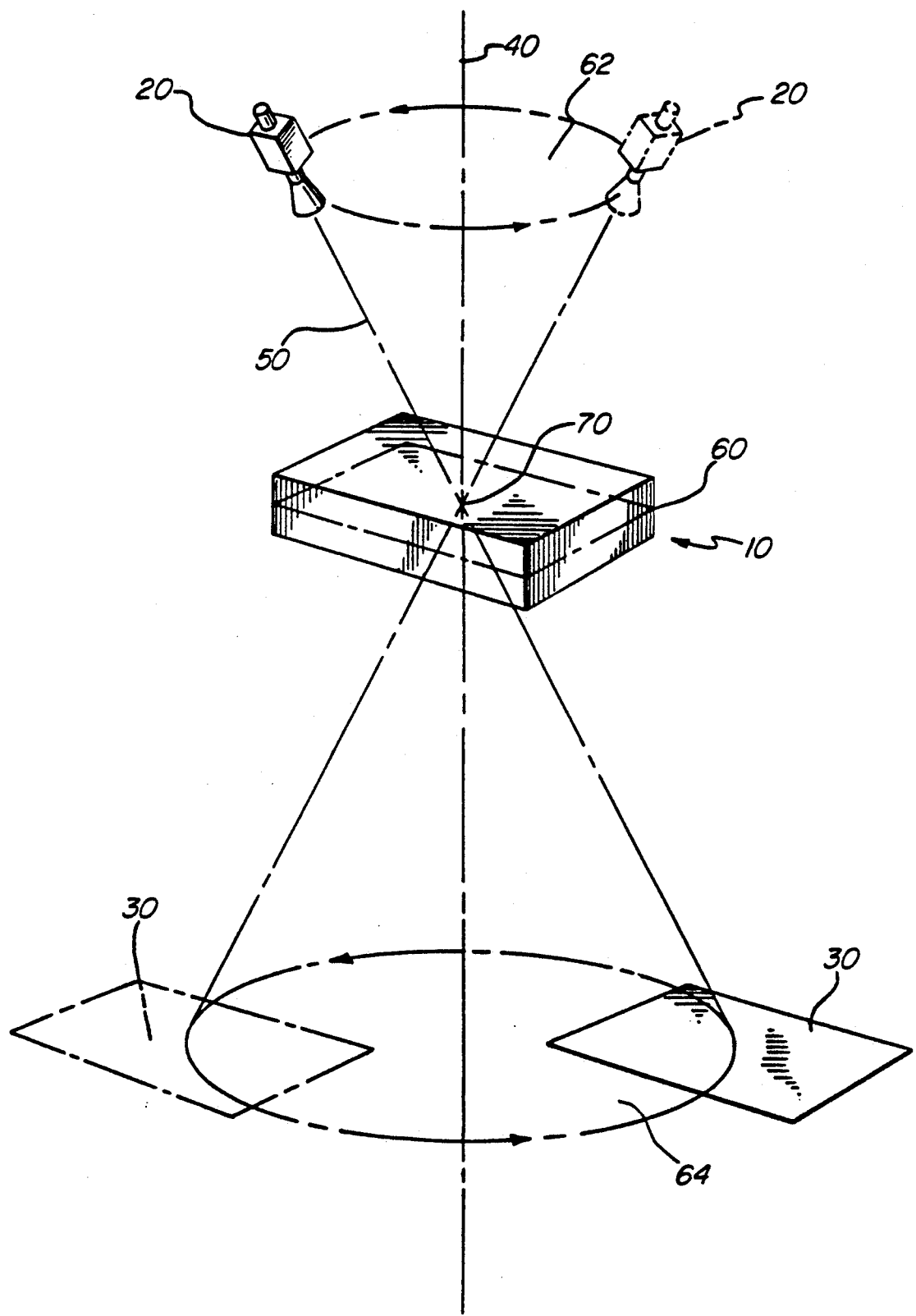
FIG. 1 is a schematic representation of a laminography system illustrating the principles of the technique.

FIG. 1 shows a schematic representation of the laminographic geometry used in the present invention. An object 10 under examination, for example, a circuit board, is held in a stationary position with respect to a source of X-rays 20 and an X-ray detector 30. Synchronous rotation of the X-ray source 20 and detector 30 about a common axis 40 causes an X-ray image of the plane 60 within the object 10 to be formed on the detector 30. The image plane 60 is substantially parallel to the planes 62 and 64 defined by the rotation of the source 20 and detector 30, respectively. The image plane 60 is located at the intersection 70 of a central ray 50 from the X-ray source 20 and the common axis of rotation 40. This point of intersection 70 acts as a fulcrum for the central ray 50, thus causing an in-focus cross-sectional X-ray image of the object 10 at the plane 60 to be formed on detector 30 as the source and detector synchronously rotate about the intersection point 70. Structure within the object 10 which lies outside of plane 60 forms a blurred X-ray image on detector 30.

The laminographic geometry shown in FIG. 1 is the geometry preferred for the present invention. However, it is not necessary that the axis of rotation of the radiation source 20 and the axis of rotation of the detector 30 be coaxial. The conditions of laminography are satisfied and a cross-sectional image of the layer 60 will be produced as long as the planes of rotation 62 and 64 are mutually parallel, and the axes of rotation of the source and the detector are mutually parallel and fixed in relationship to each other. This reduces the number of constraints upon the mechanical alignment of the apparatus used in accordance with the present invention.

FIGS. 2a–2e show laminographs produced by the above described laminographic technique. The object 10 shown in FIG. 2a has test patterns in the shape of an arrow 81, a circle 82 and cross 83 embedded within the object 10 in three different planes 60a, 60b and 60c, respectively.

Figure 2A:
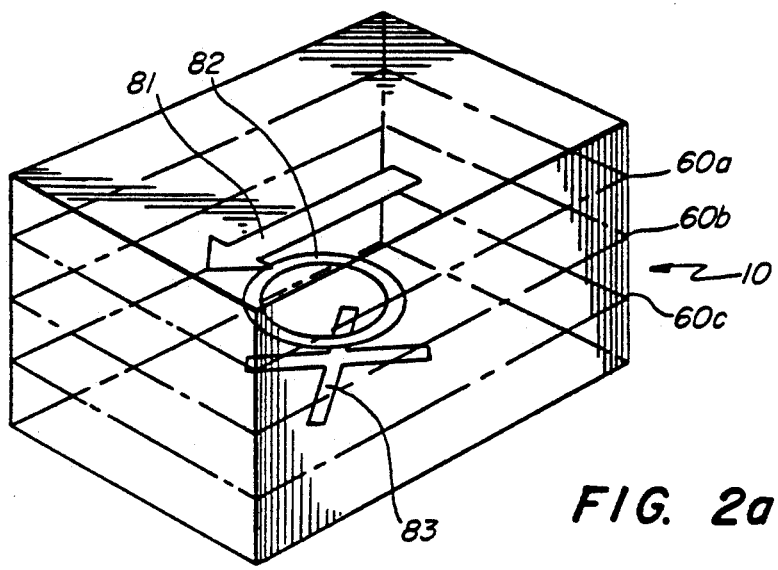
FIG. 2a shows an object having an arrow, a circle and a cross embedded in the object at three different planar locations.
Figure 2B:
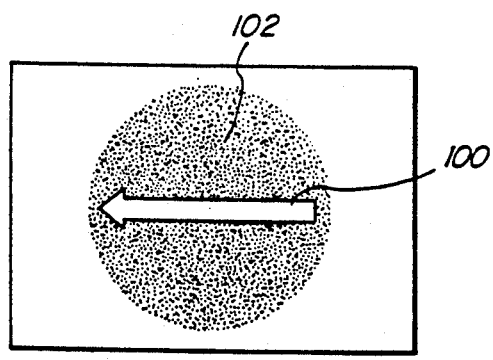
FIG. 2b shows a laminograph of the object in FIG. 2a focused on the plane containing the arrow.

FIG. 2b shows a typical laminograph of object 10 formed on detector 30 when the point of intersection 70 lies in plane 60a of FIG. 2a. The image 100 of arrow 81 is in sharp focus, while the images of other features within the object 10, such as the circle 82 and cross 83 form a blurred region 102 which does not greatly obscure the arrow image 100.

Figure 2D:
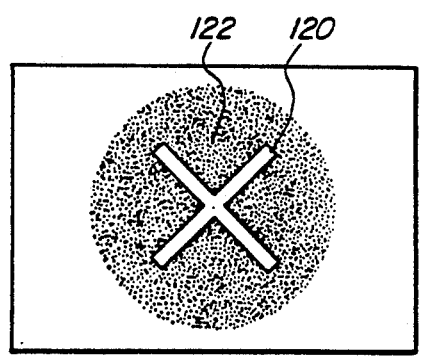
FIG. 2d shows a laminograph of the object in FIG. 2a focused on the plane containing the cross.
Figure 2C:
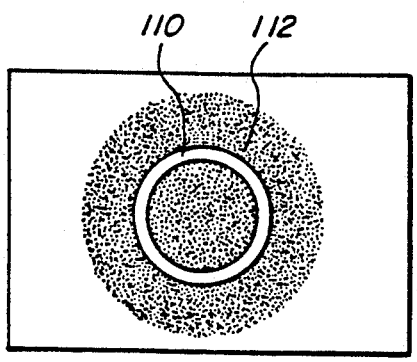
FIG. 2c shows a laminograph of the object in FIG. 2a focused on the plane containing the circle.

Similarly, when the point of intersection 70 lies in plane 60b, the image 110 of the circle 82 is in sharp focus as seen in FIG. 2c. The arrow 81 and cross 83 form a blurred region 112.

FIG. 2d shows a sharp image 120 formed of the cross 83 when the point of intersection 70 lies in plane 60c. The arrow 81 and circle 82 form blurred region 122.

Figure 2E:
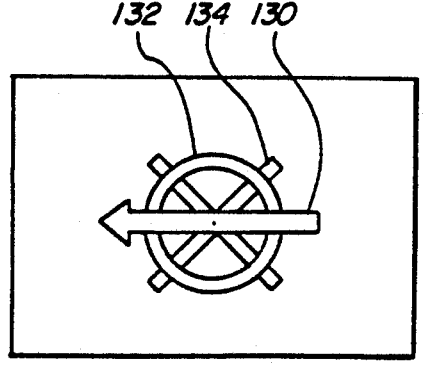

For comparison, FIG. 2e shows an X-ray shadow image of object 10 formed by conventional projection radiography techniques. This technique produces sharp images 130, 132 and 134 of the arrow 81, circle 82 and cross 83, respectively, which overlap one another. FIG. 2e vividly illustrates how multiple characteristics contained within the object 10 may create multiple overshadowing features in the X-ray image which obscure individual features of the image.

FIG. 3a illustrates a schematic diagram of a laminographic apparatus used in accordance with the invention. In this embodiment, an object under inspection is a printed circuit board 210 having multiple electronic components 212 mounted on the board 210 and electrically interconnected via electrical connections 214 (See FIG. 3b). Typically, the electrical connections 214 are formed of solder. However, various other techniques for making the electrical connections 214 are well know in the art and even though the invention will be described in terms of solder joints, it will be understood that other types of electrical connections 214 including, but not limited to, conductive epoxy, mechanical, tungsten and eutectic bonds may be inspected utilizing the invention. FIG. 3b, which is a top view enlargement of a region 283 of the circuit board 210, more clearly shows the components 212 and solder joints 214.

The laminographic apparatus acquires cross-sectional images of the solder joints 214 using the previously described laminographic method or other methods capable of producing equivalent cross-sectional images. The cross-sectional images of the solder joints 214 are automatically evaluated to determine their quality. Based on the evaluation, a report of the solder joint quality is presented to the user.

The laminographic apparatus, as shown in FIG. 3a, comprises an X-ray tube 200 which is positioned adjacent printed circuit board 210. The circuit board 210 is supported by a fixture 220. The fixture 220 is attached to a positioning table 230 which is capable of moving the fixture 220 and board 210 along three mutually perpendicular axes, X, Y and Z. A rotating X-ray detector 240 comprising a fluorescent screen 250, a first mirror 252, a second mirror 254 and a turntable 256 is positioned adjacent the circuit board 210 on the side opposite the X-ray tube 200. A camera 258 is positioned opposite mirror 252 for viewing images reflected into the mirrors 252, 254 from fluorescent screen 250. A feedback system 260 has an input connection 262 from a sensor 263 which detects the angular position of the turntable 256 and an output connection 264 to X and Y deflection coils 281 on X-ray tube 200. A position encoder 265 is attached to turntable 256. The position sensor 263 is mounted adjacent encoder 265 in a fixed position relative to the axis of rotation 40. The camera 258 is connected to a master computer 270 via an input line 276. The master computer 270 is connected to a high speed image analysis computer 272. Data is transferred between the master computer 270 and the image analysis computer 272 via data bus 274. An output line 278 from master computer 270 connects the master computer to positioning table 230.

Figure 3C:
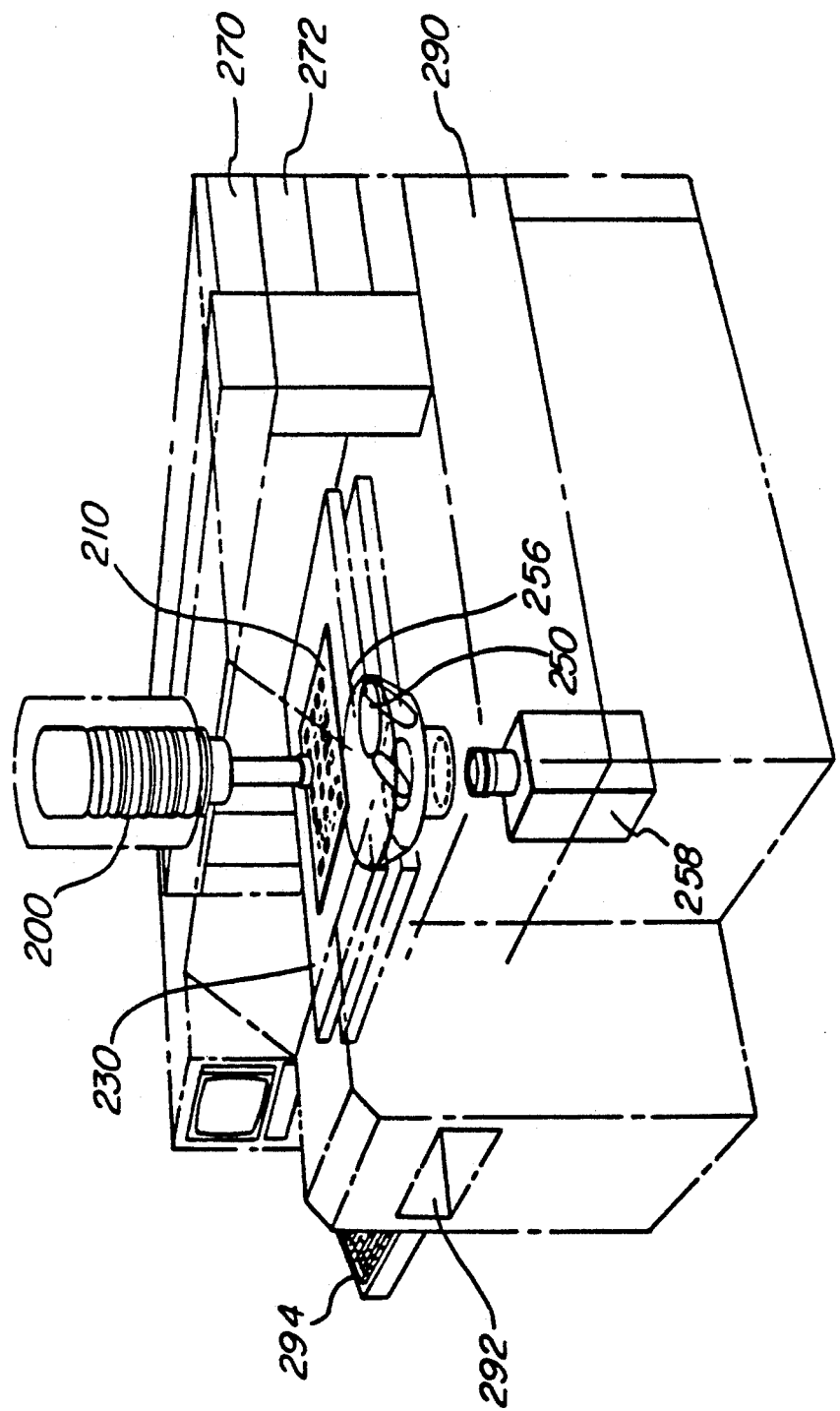

A perspective view of the laminographic apparatus is shown in FIG. 3c. In addition to the X-ray tube 200, circuit board 210, fluorescent screen 250, turntable 256, camera 258, positioning table 230 and computers 270, 272 shown in FIG. 3a, a granite support table 290, a load/unload port 292 and an operator station 294 are shown. The granite table 290 provides a rigid, vibration free platform for structurally integrating the major functional elements of the laminographic apparatus, including but not limited to the X-ray tube 200, positioning table 230 and turntable 256. The load/unload port 292 provides a means for inserting and removing circuit boards 210 from the machine. The operator station 294 provides an input/output capability for controlling the functions of the laminographic apparatus as well as for communication of inspection data to an operator.

In operation of the laminographic apparatus as shown in FIGS. 3a and 3c, high resolution, cross-sectional X-ray images of the solder joints 214 connecting components 212 on circuit board 210 are acquired using the X-ray laminographic method previously described in reference to FIGS. 1 and 2. Specifically, X-ray tube 200, as shown in FIG. 3a, comprises a rotating electron beam spot 285 which produces a rotating source 280 of X-rays 282. The X-ray beam 282 illuminates a region 283 of circuit board 210 including the solder joints 214 located within region 283. X-rays 284 which penetrate the solder joints 214, components 212 and board 210 are intercepted by the rotating fluorescent screen 250.

Dynamic alignment of the position of the X-ray source 280 with the position of rotating X-ray detector 240 is precisely controlled by feedback system 260. The feedback system correlates the position of the rotating turntable 256 with calibrated X and Y deflection values stored in a look-up table (LUT). Drive signals proportional to the calibrated X and Y deflection values are transmitted to the steering coils 281 on the X-ray tube 200. In response to these drive signals, steering coils 281 deflect electron beam 285 to locations on an annular shaped target anode 287 such that the position of the X-ray source spot 280 rotates in synchronization with the rotation of detector 240 in the manner previously discussed in connection with FIG. 1.

X-rays 284 which penetrate the board 210 and strike fluorescent screen 250 are converted to visible light 286, thus creating a visible image of a single plane within the region 283 of the circuit board 210. The visible light 286 is reflected by mirrors 252 and 254 into camera 258. Camera 258 typically comprises a low light level closed circuit TV (CCTV) camera which transmits electronic video signals corresponding to the X-ray and visible images to the master computer 270 via line 276. The electronic video format image is transferred to the high speed image analysis computer 272 via line 274. The image analysis computer 272 analyzes and interprets the image to determine the quality of the solder joints 214.

Master computer 270 also controls the movement of positioning table 230 and thus circuit board 210 so that different regions of circuit board 210 may be automatically positioned within inspection region 283.

ROTATING X-RAY SOURCE

Figure 4:
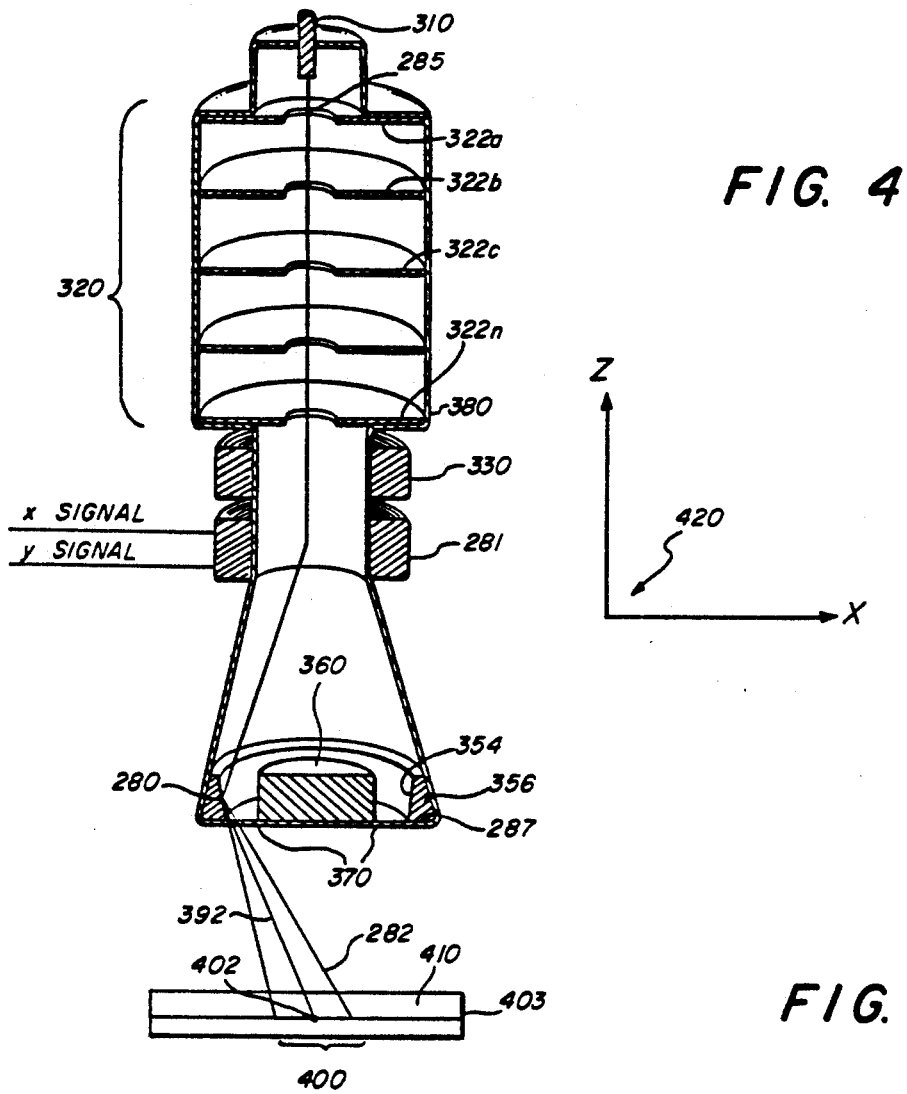
FIG. 4 shows details of an X-ray tube having a rotating spot source of X-rays for use in the preferred embodiment.

FIG. 4 illustrates an X-ray tube 200 capable of providing the rotating beam of X-rays 282 for producing high resolution laminographs of circuit boards. The tube 200 comprises an electron gun 310 mounted adjacent a high voltage electrode section 320. Focus coils 330 and steering coils 281 are positioned intermediate the electrode section 320 and the annular shaped target anode 287. An electron beam stop 360 and X-ray window 370 are mounted within the central area defined by the annular shaped anode 287. A vacuum envelope 380 encloses the evacuated portions of the X-ray tube assembly 200.

In operation, electron gun 310 emits an electron beam 285 into the high voltage electrode section 320. A high DC voltage is applied between the electron gun 310 and target anode 287 to accelerate and guide electron beam 285 toward a collision with the anode 287. Portions of the high voltage signal are applied to electrodes 322 which guide, accelerate, and shape electron beam 285. In a preferred embodiment, the high voltage signal is approximately 160 kilovolts and is capable of providing approximately 7.5 microamps of current through electron beam 285 to anode 287. Preferably, the high voltage signal is maintained constant to within an accuracy of approximately 0.01%. It will be understood that these values are exemplary and that other voltages, currents, and accuracies may also be used.

After traversing electrode section 320, the electron beam 285 enters a region of the tube wherein the shape and direction of the electron beam are affected by the focus coils 330 and steering coils 281. In a preferred embodiment, the coils 330 and 281 produce electromagnetic fields which interact with the electron beam 285 to focus as well as direct the electron beam 285 toward specific locations on the anode 287. The X-ray source 280 coincides with these specific locations from which the X-ray beam 282 is emitted. In this manner, an extremely small, approximately 20-micron diameter electron beam spot is formed on the anode 287 at these locations. As is well known in the field of radiography, the size of this spot plays a very important role in determining the overall resolution of the X-ray images obtained from the source of X-rays 280.

The steering coils 281, in combination with the annular shaped anode 287 enable the X-ray tube 200 to provide X-rays from source 280 wherein the location of the source 280 moves in a circular pattern around the anode. The circular pattern is centered about a fulcrum point 402 located within a cross-sectional image plane 403 of object 410.

Specifically, the steering coils 281 are capable of directing the electron beam 285 toward any desired portion of an inner surface 354 of anode 287. By driving the electromagnetic coils 281 with appropriately synchronized X and Y drive signals, the electron beam 285 can be steered toward the anode 287 such that the beam inscribes a circular path along the inner surface 354 of the anode 287.

In a preferred embodiment, the steering coils 281 comprise separate X and Y electromagnetic coils which deflect electron beam 285 in the X and Y directions respectively. Electrical current flowing in the coils 281 creates magnetic fields which interact with the electron beam 285 causing the beam to be deflected. These coils 281 are similar in structure and function to the yoke coils found in cathode ray tubes (CRT). It will be understood, however, that electrostatic deflection techniques could also be used to deflect the electron beam 285.

The surface 354 upon which the electron beam 285 strikes the anode 287 is shaped so that a central X-ray 392 of X-ray beam 282 originates at source location 280 and is directed toward the fulcrum point 402. Thus, as the electron beam 285 circumscribes a circular path along the surface 354, the central beam 392 is always directed toward the same location 402.

The material forming the surface 354 of the anode 287 is selected so that the radiation produced when electron beam 285 strikes the surface 354 has the desired energy characteristics. The radiation produced by bombarding a target material with an accelerated electron beam is known as Bremsstrahlung radiation. The characteristics of Bremsstrahlung radiation are determined primarily by the energy of the electron beam and the material composition of the target into which the electron beam is directed. In a preferred embodiment, the surface 354 which is bombarded by electron beam 285 is covered with a layer of tungsten metal.

The substrate 356 on which the tungsten surface 354 is placed may be copper or other suitable metal. A material with a high heat conductivity, such as copper, is particularly well suited for this application since significant heating of the target anode 287 occurs when the energy of the electron beam 285 is deposited in the anode. The copper substrate 356 provides a very efficient heat conductor for removing this heat from the locations 280 where electron beam 285 collides with the anode 287.

The radiation beam 282 produced in the collision of electron beam 285 with tungsten layer 354 exits the tube 200 through a window 370. The window 370 forms a portion of the vacuum envelope of the tube 200 in which the electron beam 285 propagates which allows the X-rays produced within the tube at the surface 354 to exit the vacuum portion of the tube with minimal loss of intensity and energy. Titanium is commonly used to form X-ray windows for X-ray tubes and is preferred in this embodiment for window 370. However, it will be understood that other materials could also be used to form the window 370.

During the X-ray inspection of a circuit board or other object 410, it is often advantageous to turn off the X-rays while the circuit board is being moved so that different regions of the board fall within the inspection area 400. It is desirable that the X-rays be turned on and off as rapidly as possible. Additionally, it is desirable to perform the ON/OFF cycling so that the X-rays produced during all of the ON portions of the cycles have substantially identical energy, intensity and optical characteristics. X-ray tube 200 accomplishes this rapid ON/OFF stabilized cycling of the X-rays by directing the electron beam 285 into the beam stop 360. This diversion of electron beam 285 prevents X-rays from exiting the window 370. Thus, radiation production directed toward the object 410 is stopped, i.e. turned off, while the object is being repositioned. Steering coils 281 provide a fast means for accomplishing this deflection of electron beam 285 into the beam stop 360. This method of turning off the X-rays enables the electron beam 285 and all other functions of the X-ray tube which affect the X-ray beam 282 characteristics to be left undisturbed during the ON/OFF cycling. Therefore, when the electron beam 285 is redirected to the anode 287 for the ON portion of the cycles, the characteristics of X-ray beam 282 are substantially unchanged from previous ON cycles.

The beam stop 360 is formed of a material which is highly attenuative of X-rays, for example, lead or copper. The thickness, location, and shape of the beam stop 360 are selected to prevent X-rays from exiting the tube 200 via the window 370 when the beam is directed into the beam stop. These parameters are easily determined by one skilled in the art of X-ray tube design.

Figure 5:
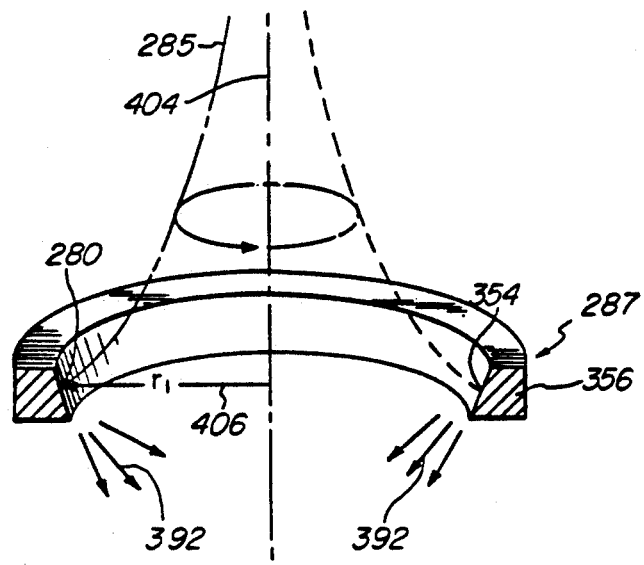
FIG. 5 is a cross-sectional view of the target anode of the X-ray tube shown in FIG. 4.

An enlarged cross-sectional view of anode 287 is shown in FIG. 5. In this preferred embodiment, the annular target surface 354 comprises a portion of a cone which is symmetric about an axis 404. The target anode 287 is mounted to the tube 200 such that the axis 404 of the cone coincides with the central Z axis of the tube 200. Thus, when the electron beam 285 is steered in a circular oscillation with the radius $r_1$ shown as 406, the effect is that of a moving spot source of radiation 280 having energy, intensity, and focus characteristics equivalent to conventional stationary radiation sources. It will be understood that other shapes for the anode 287 may be used which will produce equivalent results.

The X-ray source 200 thus provides a source of X-rays suitable for making high resolution X-ray images even when used in a geometry which magnifies the images. Additionally, source 200 has the capability of moving this source of X-rays in a circular pattern suitable for making laminographs. This circular motion is accomplished without sacrificing image resolution or speed of acquisition. Since the rotation of the radiation source is accomplished electronically, no moving parts are needed, thus eliminating vibrations and other undesirable characteristics of mechanical systems. An X-ray source having the above described characteristics is available from Kevex Corporation as Model No. KM160R. Other electrically steered moving X-ray sources are described in U.S. Pat. No. 4,075,489 entitled "Method and Apparatus Involving the Generation of X-Rays"; U.S. Pat. No. 4,352,021 entitled "X-Ray Transmission Scanning System and Method and Electron Beam X-Ray Scan Tube for Use Therewith"; and U.S. Pat. No. 2,319,350 entitled "X-Ray Tube and Apparatus." These patents are hereby incorporated herein by reference.

ROTATING X-RAY DETECTOR

Figure 6:
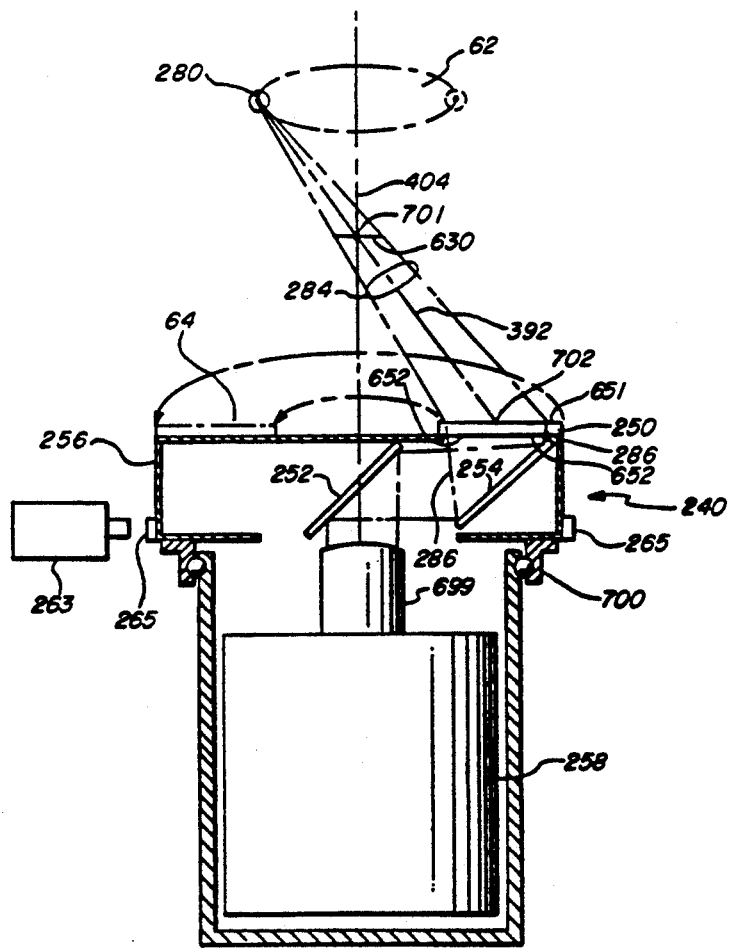
FIG. 6 is a cross-sectional view of the rotating X-ray detector and camera system.

Shown in FIG. 6 is an embodiment of the rotating X-ray detector system 240 discussed previously in connection with FIG. 3a and used in conjunction with the rotating X-ray source 280 to acquire cross-sectional images of an object 630. As shown in FIG. 6, an X-ray image of the object 630 is formed on the rotating fluorescent screen 250 by X-ray beam 284. Screen 250 converts these X-rays to optical signals 286 for detection by conventional optical devices. In the preferred embodiment, the optical signals 286 from rotating fluorescent screen 250 are detected by the closed circuit TV (CCTV) camera 258. Camera 258 converts the optical signals 286 to electrical signals for further processing by computer systems 270 and 272. The optical image formed on the screen 250 rotates with the screen. In order to eliminate the need for mechanical motion of the CCTV camera 258 which views the rotating optical image, the optical image is derotated within the rotating detector 240 by optical mirrors 252 and 254 so that the rotating optical images formed on the rotating screen 250 appear stationary as viewed by the camera.

The rotating X-ray detector 240 comprises the turntable 256 rotatably mounted about the axis 404 by a bearing 700. It is noted that the axis 404 is nominally the same axis about which the source of rotating X-rays 280 revolves. The fluorescent screen 250 is attached to the top of turntable 256. The two mirrors 252 and 254 are mounted within turntable 256 parallel to one another and at an angle of 45° with respect to axis 404. The mirror 252 is mounted in the center of turntable 256 so that it intersects the axis 404 near the center of the mirror. The mirror 254 is mounted within turntable 256 so that it faces both the first mirror 252 and the fluorescent screen 250. Fluorescent screen 250 and mirrors 252 and 254 are attached to turntable 256 so that the turntable, mirrors and screen rotate about axis 404 as a single unit. This arrangement of mirrors, turntable, and screen forms an optical derotation assembly for optical images formed on the screen 250 when the detector 240 is rotated about the axis 404.

An X-ray shadow image of the object 630 is formed on the fluorescent screen 250 when the X-ray beam 284 strikes the screen. The fluorescent screen 250 functions as an X-ray to optical converter. For example, when X-rays 284 strike the surface 651 of the screen 250 which faces the X-ray source 280, visible light 286 is emitted from the screen surface 652 opposite the X-ray source 280. Optical signals 286 emitted from the fluorescent screen surface 652 are reflected by the two parallel mirrors 252 and 254 into a lens 699 attached to the closed circuit TV camera 258.

The fluorescent screen 250 is mechanically rotated at a uniform angular velocity about the axis 404 in plane 64 which is substantially parallel to plane 62 defined by the circular motion of the moving spot source of radiation 280. The mirrors 252, 254 reflect the optical image from the rotating fluorescent screen into the stationary camera system 258 through the lens 699 so that the rotation of the image in the plane 64 is not apparent to the camera 258. This mirror arrangement has been previously described in U.S. Pat. No. 2,998,511 entitled "Tomoscope."

As a result of the fixed mounting of the fluorescent screen 250 to the rotating turntable 256, successive images of object 630 formed on the screen have different orientations with respect to the screen as it traverses its circular path about the axis 404. Thus, in order to avoid blurring of the image caused by the movement of the image with respect to the screen, it is desirable that the fluorescence of a point on the screen surface be suppressed abruptly after that point is no longer hit by an X-ray. In a preferred embodiment, the fluorescent screen 250 comprises praseodymium-doped gadolinium oxysulfide, $Gd_2O_2S:Pr$. Praseodymium-doped gadolinium oxysulfide is a scintillation material which is "fast" enough to prevent blurring due to motion of the image with respect to the screen and also provides sufficient light output for detection by the camera system 258.

Alternatively, "slower" screens may be used. However, in order to prevent motion blurring, the screen 250 must be rotatably mounted to the turntable 256 such that an image of object 630 formed on the screen remains stationary with respect to the screen. Such a motion may be accomplished, for example, by a set of gears which superimposes a circular motion of the screen with respect to the turntable in synchronization with the rotation of the turntable about the axis 404.

An alternative embodiment (not shown) for the rotating X-ray detector 240 which forms an optical derotation assembly replaces the two flat mirrors 252,254 with a suitably bent bundle of image conductors, e.g., optical fibers, which are coupled to the fluorescent screen 250 and rotate in unison with the screen. The image conductors transmit the image from the fluorescent screen 250 to a position centered on the axis of rotation 404, to the same effect as the two parallel mirrors shown in FIGS. 3a and 6. These image conductors may comprise optical fibers, electron conductors or equivalent devices.

CROSS-SECTIONAL IMAGE FORMATION

As previously discussed, a cross-sectional image of object 630 is formed on screen 250 as the screen 250 and X-ray source 280 synchronously rotate about axis 404. The blurring effects of the laminography method and image resolution are maximized when the cross-sectional image is acquired during a full rotation of the screen 250 and source 280 about the axis 404. The camera system 258 detects the development of the cross-sectional image on the fluorescent screen 250 by means of the optical derotation assembly comprising mirrors 252 and 254.

Since the fluorescent screen 250 may not emit high intensity optical signals, it is often advantageous to detect the optical signals 286 with a high sensitivity, low light level device. Use of a low light level detection device thus improves the detected image quality by detecting a larger portion of the optical signals 286 emitted from the fluorescent screen 250 during a single rotation of the screen. Many low light level camera systems incorporate an image intensifier as part of the camera system to improve the low light level sensitivity. One particular system is known as a silicon intensified target (SIT) camera and is capable of detecting extremely low levels of light. SIT camera systems are well known and readily available. An embodiment of the laminographic apparatus used in accordance with the present invention utilizes a SIT camera system which is based upon the RCA Model No. 4804BHP2-12 SIT tube.

In a preferred embodiment, one cross-sectional image is acquired in approximately 0.1 seconds during the rotation of the fluorescent screen 250 about the axis 404 at the rate of approximately 600 revolutions per minute. During one complete revolution, three video frames, each frame having a duration of 1/30 of a second, are collected by the camera 258. The three video frames are communicated from the camera 258 to master computer 270 (shown in FIG. 3a) where the three frames are averaged together, thus forming a digital representation of the cross-sectional image of the object 630 formed on the fluorescent screen 250 during a single rotation of the screen 250 about the axis 404. Alternatively, the camera 258 may be connected to a CRT, so that the cross-sectional image can be viewed directly.

SOURCE/DETECTOR SYNCHRONIZATION

Figure 7:
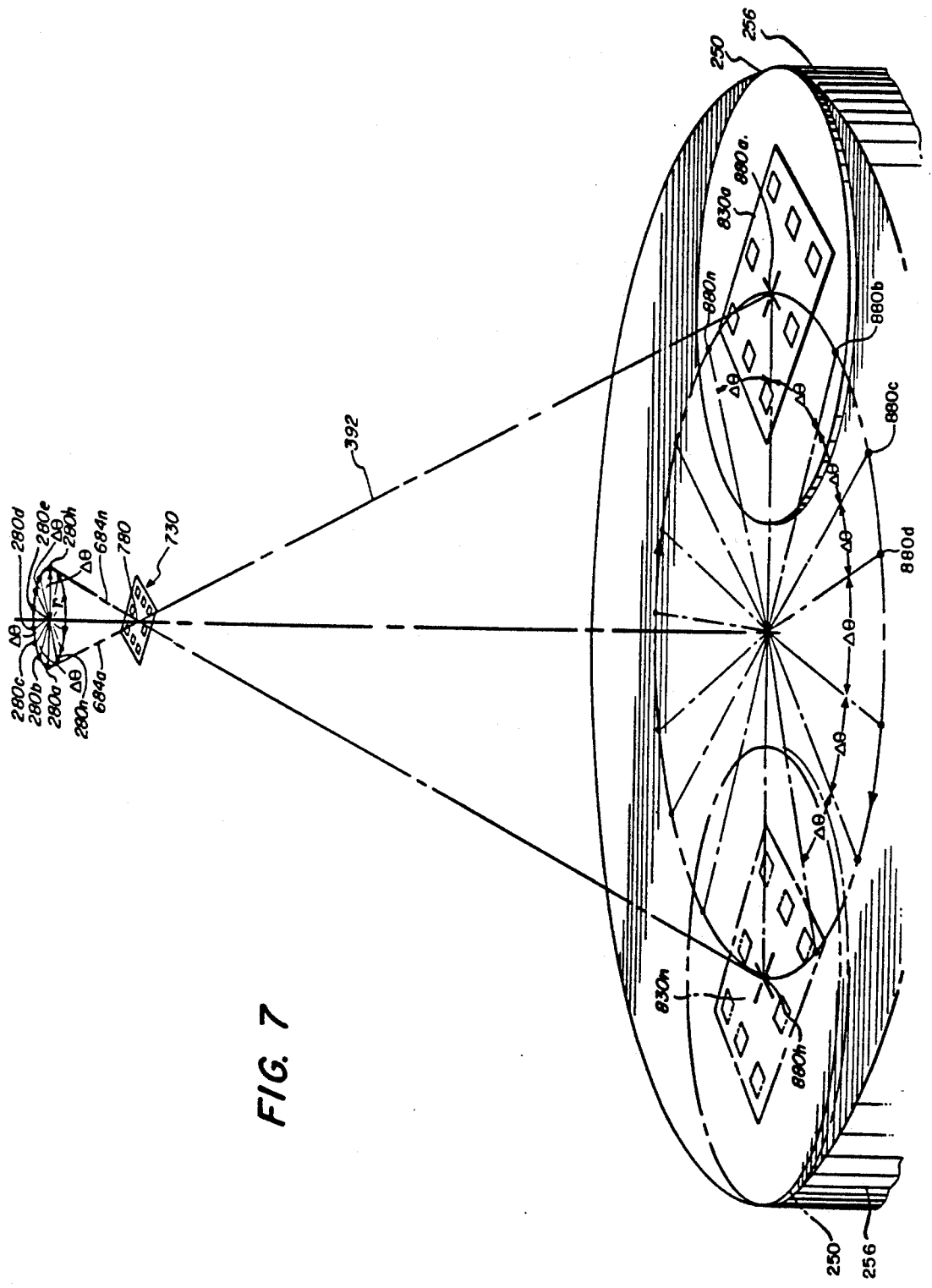
FIG. 7 is a schematic diagram illustrating the calibration procedure for synchronizing the X-ray source and detector positions.

Formation of a high resolution laminographic cross-sectional image depends upon the precise alignment and synchronization of the circular motions of the radiation source 280 and detector screen 250. As illustrated in FIG. 7, proper alignment and synchronization are achieved when central X-ray 392 from source 280 passes through a fixed point 780 lying on the axis 404, such that the central X-ray 392 is always directed to a single point 880 on the surface of detector screen 250. For the configuration shown in FIG. 7, this is clearly achieved when the angular positions of the source and detector screen, relative to a fixed reference position, are separated by 180°.

The preferred alignment and synchronization of the source 280 and detector screen 250 are maintained by the feedback system 260 shown in FIG. 3a. The position of the rotating turntable 256, upon which the X-ray detector screen 250 is mounted, is monitored by the sensor 263. The turntable position is communicated to the feedback system 260, which supplies drive signals corresponding to the position of the turntable to the electron beam deflection coils 281. The drive signals control the position of the X-ray source 280 such that the source 280 and screen 250 are always in alignment as the turntable rotates about the axis 404. In this manner, the feedback system maintains the precision geometry necessary for the production of high resolution cross-sectional images. This system compensates for alignment inaccuracies of the X-ray tube 200 and rotating X-ray detector 240; machining, mounting and fabrication inaccuracies and defects of the target anode 287 and its surface coating 354; aberrations, such as astigmatism, in the electron beam 285 path through the X-ray tube; and variations in the rotational velocity of the rotating turntable during image formation.

Figure 8:
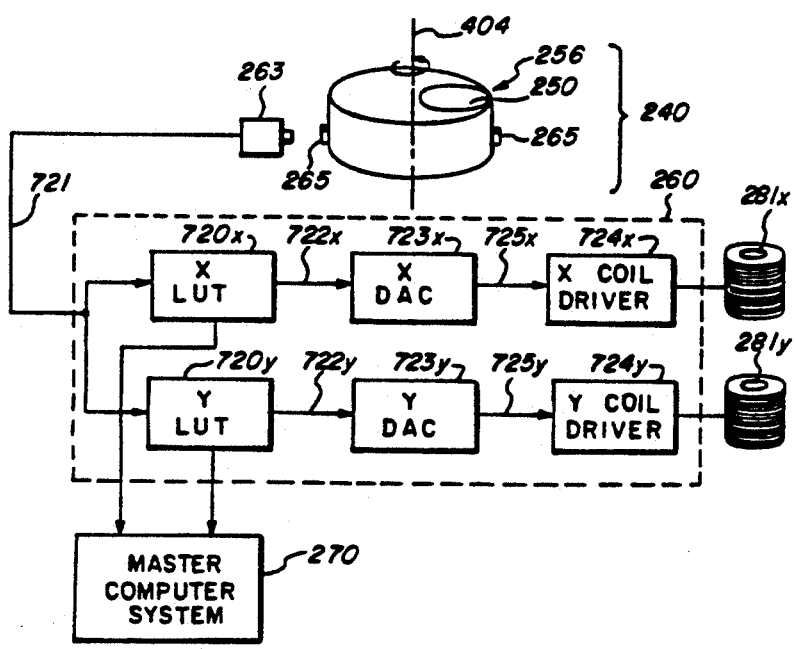
FIG. 8 is a schematic block diagram for the feedback control system used for the synchronization of the X-ray source and detector motions.

A detailed block diagram of feedback system 260 is shown in FIG. 8. Feedback system 260 comprises X and Y look-up tables (LUTs) 720X and 720Y, respectively, X and Y digital-to-analog converters (DACs) 723X and 723Y, respectively, and X and Y coil drivers 724X and 724Y, respectively. The LUTs 720X and 720Y are preferably solid state, digital random access memories (RAM). The feedback system links the rotating X-ray detector 240 to the X-ray tube deflection coils 281 under control of the master computer system 270.

As rotating X-ray detector 240 revolves about axis 404, the position sensor 263 detects the angular position of the detector 240 from the position encoder 265. The detected angular position is converted to X and Y address signals which correspond to the angular position of the detector. The address signals are communicated to the X and Y LUTs 720X, 720Y via a communication line 721. By means of a source/detector alignment calibration procedure, X and Y calibration data are determined and stored in the X and Y LUTs for each angular position of the detector. Thus, there exists a one to one correspondence between the X and Y addresses from the encoder and the X and Y calibration data in the LUT's. The X and Y calibration data are retrieved from the LUT's in the form of electronic digital signals. The electronic digital signals are transmitted from the X and Y LUTs to the X and Y DACs 723X and 723Y, respectively, via communication lines 722X and 722Y. The DACs convert the digital signals into analog electrical signals which travel via lines 725X and 725Y to the coil drivers 724X and 724Y. The coil drivers amplify their respective analog input signals and apply resulting output signals via lines 726X and 726Y to the coils 281X and 281Y, respectively, to achieve the precise deflection of the electron beam 285 required for proper alignment of the source and detector. The electron beam is deflected through interaction with magnetic fields generated by the application of the output signals to the coils 281. As the electron beam traverses the magnetic fields, it is deflected, thus moving the position of the X-ray source spot 280 on the anode 287. The distance the spot moves is proportional to the magnitude of the drive signals as determined by the calibration data.

The LUT calibration data are determined using the calibration configuration schematically illustrated in FIG. 7. A test pattern 730 is positioned between the X-ray source 280 and detector screen 250 such that test pattern 730 intersects the axis 404 at location 780. A conventional X-ray shadowgraph image 830 of test pattern 730 is formed on screen 250. The optical representation of X-ray image 830 on the screen is viewed by the camera 258 (See FIG. 3a). An electrical representation of the optical image is output from camera 258 by means of electrical signals on line 276 to master computer 270 and image analysis computer 272. The electrical signals on line 276 are digitized by computer 270 and stored in the memory of computer 270 in digital format.

Figure 9A:
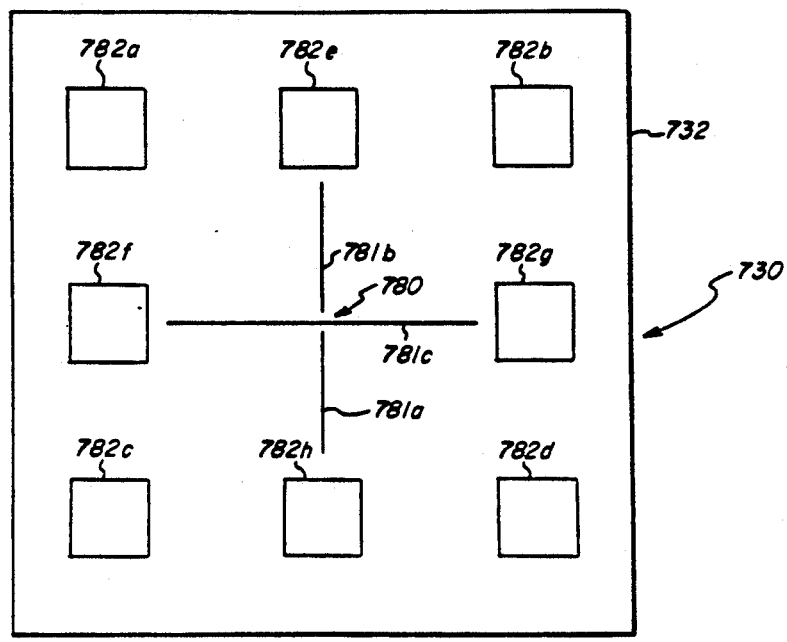
FIG. 9a illustrates a test fixture for use in the calibration procedure shown in FIG. 7.

A preferred embodiment of test pattern 730, shown in FIG. 9a, comprises a foundation 732 of material such as plastic, which is relatively transparent to X-rays. Foundation 732 is approximately 0.5×0.5 inch in length and width, and approximately 0.1 inch thick. At a center location 780 on foundation 732 are mounted three pieces of 0.001 inch diameter tungsten wire 781a, 781b and 781c, oriented such that wire 781c intersects the center location 780. Wires 781a and 781b are mounted to foundation 732 so that they are on opposite sides of wire 781c, and so that a line connecting wires 781a and 781b also intersects center location 780. Thus, wires 781a, 781b and 781c form a fiducial crosshair 781 having its center at location 780. Mounted around the crosshair 781 are eight markers 782 made of lead or other X-ray opaque material. Lead markers 782a through 782d are approximately 0.0625 inch square and 0.004 inch thick, and are located near the four corners of the foundation 732. Lead markers 782e through 782h are approximately 0.0625 inch square and 0.008 inch thick, and are positioned intermediate the markers 782a through 782d.

Figure 9B:
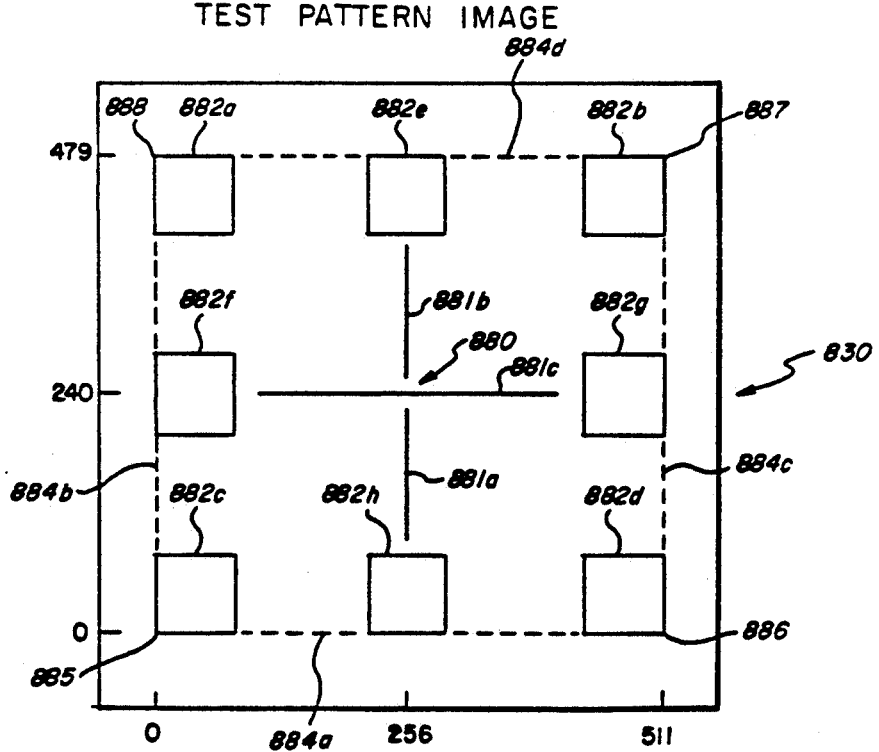

A representation of a typical X-ray shadowgraph image 830 of test pattern 730 is shown in FIG. 9b. Lead markers 782a through 782h form image regions 882a through 882h, respectively, of image 830. The center 780 of test pattern 730 is represented by image center 880. Likewise, tungsten wires 781a through 781c form image regions 881a through 881c, respectively.

A portion of image 830 represented by the dotted lines 884a through 884d forms a rectangular region of interest (ROI) 884 which surrounds the images of lead markers 882 and tungsten wires 881. Region of interest 884 is stored in the computer 270 in digital format. As is well known, digitally stored images comprise an array of pixels, each pixel representing a small portion of the image. Specifically, region of interest 884 is divided into a pixel grid comprising 512 columns along border 884a and 480 rows along border 884b. Each pixel in the grid may be represented by its corresponding column and row designation. For example, the lower left corner 885 of region of interest 884 is represented by the pixel (0,0). Similarly, corner 886 is represented by pixel (511,0), corner 887 is represented by pixel (511,479) and corner 888 is represented by pixel (0,479). The center location 880 is represented by pixel (256,240). In one embodiment, the distance between corners 885 and 886 of the image 830 corresponds to approximately 0.400 inches on the test pattern 730. Likewise, the distance between corners 885 and 888 of the image corresponds to approximately 0.375 inches on the test pattern.

Determination of the calibration data for the X and Y LUTs is performed either manually or automatically using the test pattern 730. Referring again to FIGS. 3a and 7, an initial alignment of the X-ray source 280, test pattern 730, turntable 256 and camera 258 is performed manually. First, the test pattern 730 is positioned so that the center 780 intersects the axis 404. The X-ray tube 200, turntable 256 and camera 258 are then mechanically aligned so that the test fixture image 830, formed on the screen 250, is continuously within the field of view of the camera throughout a complete revolution of the source 280 and turntable 256 about the axis 404. After the system is thus mechanically aligned, the turntable 256 is positioned at an initial angular position defined as $\theta=0°$. In this initial position, the center pixel (256,240) of the digital image detected by the camera and stored in the computer corresponds to a location 880a on the screen 250. The source 280 is positioned at a location 280a which corresponds to an angular position of approximately $\theta=180°$, thus placing the test pattern image 830 within the field of view of the camera. If the image center 880 of the test pattern image 830 does not fall within the center pixel (256,240), then the X and Y deflection values are adjusted to change the position 280a of the source 280, which in turn changes the location of the image center 880 on the screen 250. The deflection values are adjusted until the image center 880 is caused to be precisely located at center pixel location (256,240). These deflection values are then stored in the LUT's 720 as the calibration data for the turntable 256 position $\theta=0°$. Turntable 256 and screen 250 are then moved to a new angular position corresponding to an angle $\theta=\Delta\theta$. Source 280 is moved to a position 280b corresponding to an angular position of approximately $\theta=\Delta\theta+180°$, thus placing the test pattern image 830 within the field of view of the camera. If the image center 880 of the test pattern image 830 does not fall within the center pixel (256,240), then the X and Y deflection values are adjusted to change the position 280b of the source 280 so that the image center 880 is again caused to be precisely located at center pixel location (256,240). These deflection values are then stored in the LUT's as the calibration data for the turntable 256 position $\theta=\Delta\theta$. This procedure for determining the LUT calibration data is continued in increments of $\Delta\theta$ until the source 280 and turntable 256 have completed one revolution about the axis 404.

The LUT calibration data determined for positions 280a, 280b, 280c, . . . ,280n of the source are used to determine the formula representing a circle of radius r as a function of angular position $\theta$. The radius r is the nominal radius of the path followed by the rotating source 280. This formula is then used to calculate calibration data for locations of the source intermediate the locations 280a, 280b, 280c, . . . ,280n.

Figure 10A:
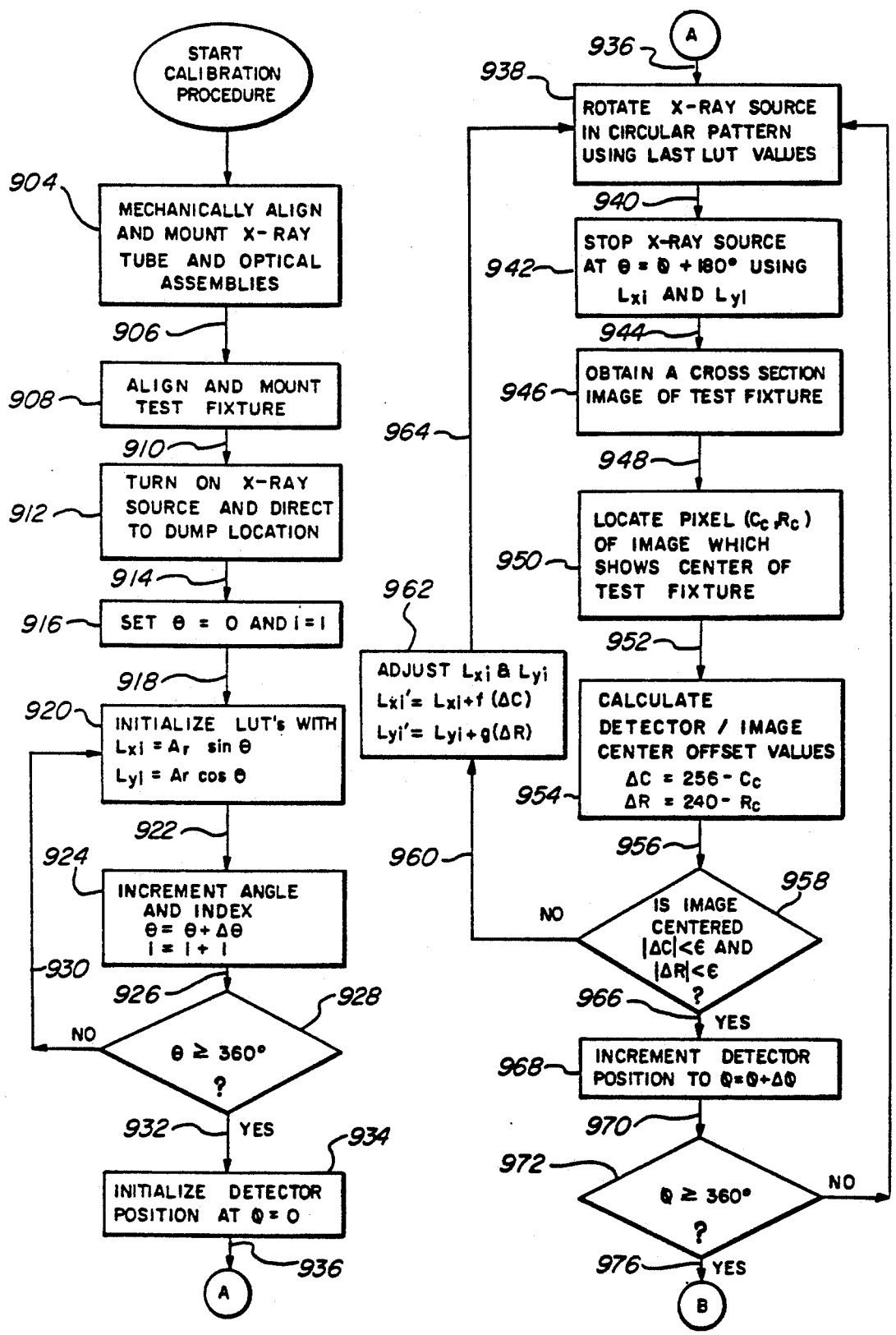
FIG. 10a is a flowchart of a procedure used to calibrate the synchronization of the X-ray source and detector positions.
Figure 10B:
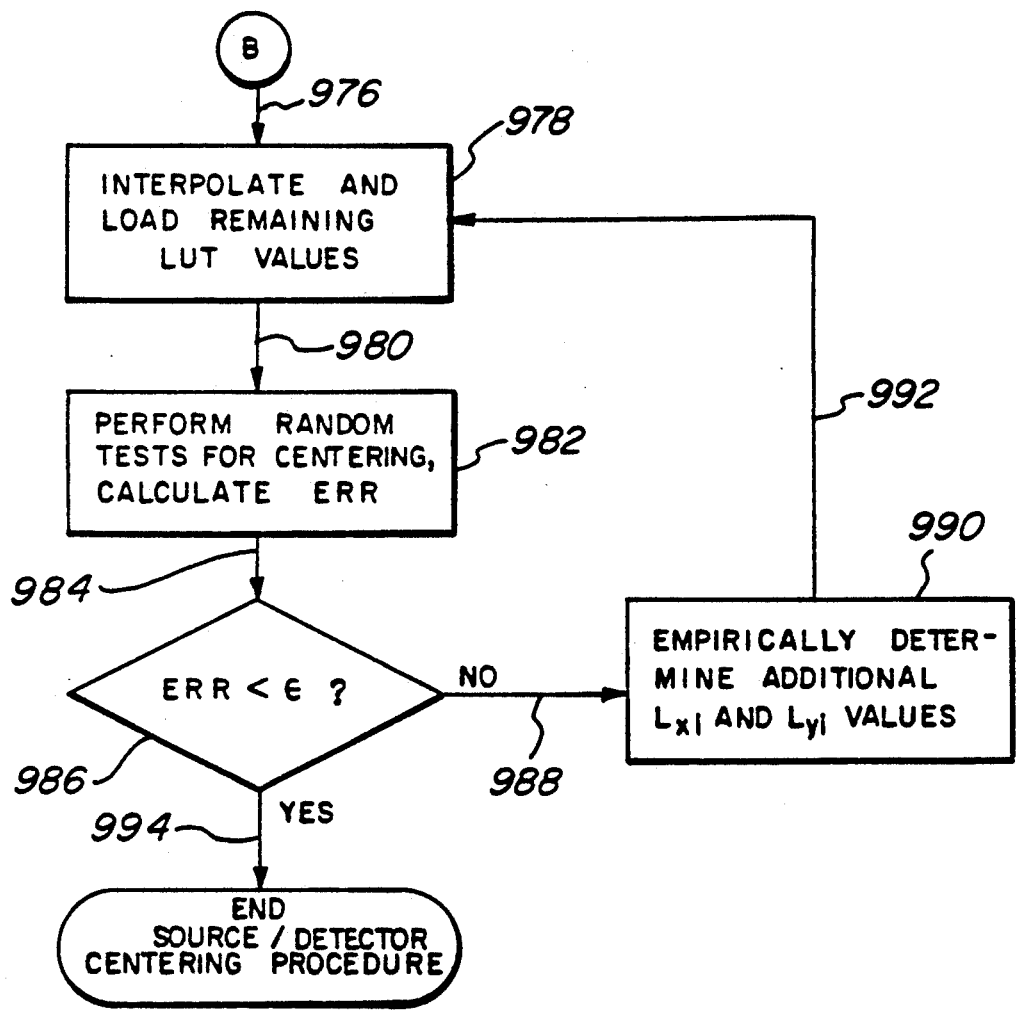

FIG. 10 illustrates a basic flow chart of the logical sequence of steps performed by the calibration procedure to determine the X and Y calibration data which are stored in the X and Y LUTs 720 for controlling the deflection coils 281. First, as previously described, the mechanisms of the laminographic apparatus, as shown in FIG. 3a, including the X-ray tube 200, turntable assembly 256 and XYZ positioning table 230 are assembled and mounted in approximate alignment. Next, test pattern 730 is mounted to the XYZ positioning table and moved by the XYZ positioning table to a position such that the center location 780 of the test pattern 730 coincides with the point 780 represented by the intersection of the central axis 404 and the nominal center X-ray 392 from the X-ray source 280 (See FIG. 7).

The step of mechanically aligning the X-ray tube 200 and optical assemblies is represented by an activity block 904 in FIG. 10. Control is passed from activity block 904 via a path 906 to an activity block 908, wherein the test fixture 730 is mounted and aligned on the positioning table. Control then passes via a path 910 to an activity block 912 wherein the X-ray source is turned on and the electron beam is directed to a beam dump location. This allows the X-ray tube to stabilize without subjecting the test pattern and detector to X-rays. Control proceeds via path 914 to an activity block 916 wherein the angular position variable $\theta$ and an address indexing variable i are initialized at $\theta = 0°$ and i = 1, respectively. Control is passed from activity block 916 to activity block 920 via a path 918. Activity block 920 represents the initialization of the LUTs with initial approximations given by $$L_{xi} = A_r \sin\theta \qquad (1)$$

$$L_{yi} = A_r \cos\theta \qquad (2)$$

where $A_r$ is proportional to the approximate radius of the rotating source 280 and i is the LUT address which contains deflection data corresponding to the angular position $\theta$. In activity block 924, reached via path 922 from block 920, the angular position $\theta$ is incremented by an amount $\Delta\theta$ and the index i is incremented by 1. In one preferred embodiment, the angular increment $\Delta\theta$ is approximately 0.022°, corresponding to approximately 16,384 angular positions in one revolution. In this embodiment, the X and Y LUT's each have at least 16384 address locations for the storage of deflection data corresponding to each discrete angular position, and the addressing index i takes on integral values ranging from 1 to at least 16384. Control then passes via path 926 to decision block 928. In decision block 928, the value of $\theta$ is checked to see if it is greater than or equal to 360°. If $\theta$ is not greater than or equal to 360°, then control returns to block 920 via path 930. If $\theta$ is greater than or equal to 360°, then control passes via path 932 to activity block 934. The steps from 920 through 928 form a loop wherein all of the available LUT addresses are loaded with initial deflection values which will cause the electron beam to circumscribe a circular path upon the anode of the X-ray tube. In the embodiment having 16,384 discrete angular positions, the steps 920 through 928 will be executed approximately 16,384 times.

Upon completion of the LUT initialization process, control passes via path 932 to activity block 934, wherein the detector is positioned at an initial reference location defined as $\theta = 0°$. Control is then transferred via path 936 to activity block 938, wherein the current data ($L_{xi}, L_{yi}$) stored in the LUT's are used to control the rotation of the X-ray source. When activity block 938 is entered via path 936, the current data in the LUT's are the initial values calculated in accordance with equations (1) and (2) and represent an initial approximation of the final values to be calculated by the below described calibration procedure.

Determination of the LUT calibration data proceeds via a path 940 to activity block 942. In block 942, the rotating X-ray source 280 is stopped at the angular position $\theta$ which is approximately equal to ($\theta + 180°$), where $\theta$ is the angular position of the X-ray detector. For example, when the detector is at the initial position $\theta = 0°$, then the X-ray detector is positioned at angular position 180° in block 942. In the embodiment having 16,384 angular positions and corresponding LUT addresses, the deflection values stored in LUT memory locations $L_{x8192}$ and $L_{y8192}$ will produce the deflection of the electron beam to the location on the anode corresponding to an angular position of the X-ray source of 180°.

Subsequent to stopping the rotating X-ray source at angle $\theta$ in activity block 942, control is passed via line 944 to activity block 946. In activity block 946, a cross-sectional image 830 of test pattern 730 is obtained and stored in a digital image memory. In a preferred embodiment, the image memory comprises a pixel grid having 512 columns and 480 rows.

A path 948 transfers control from activity block 946 to an activity block 950, wherein the pixel(s) ($C_c, R_c$) containing the location of the image center 880 of image 830 are located. $C_c$ and $R_c$ are the column and row designations respectively, of the image pixel containing the center of the image, and may be identified manually or automatically by means of computer analysis techniques.

The image center pixel position ($C_c, R_c$) determined in activity block 950 is transferred to activity block 954 via path 952, wherein the relative offset of the image center from the detector center is calculated according to the following equations.

$$\Delta C = 256 - C_c \qquad (3)$$

$$\Delta R = 240 - R_c \qquad (4)$$

$\Delta C$ and $\Delta R$ represent the distance by which the center of the test pattern image ($C_c, R_c$) is offset from the center of the digital image defined as pixel (256,240).

The $\Delta C$ and $\Delta R$ values calculated in activity block 954 are transferred via path 956 to decision block 958, wherein $\Delta C$ and $\Delta R$ are compared to the value zero. If $\Delta C$ or $\Delta R$ is not substantially equal to zero, i.e., if their absolute values are not less than some arbitrarily small number, $\epsilon$, then the test pattern image center is not coincident with the digital image center and control is passed via path 960 to activity block 962 where the LUT calibration data are adjusted accordingly.

In activity block 962, the LUT calibration data $L_{xi}$ and $L_{yi}$ are adjusted in accordance with the following equations.

$$L_{xi}' = L_{xi} + f(\Delta C, \Delta R) \qquad (5)$$

$$L_{yi}' = L_{yi} + g(\Delta C, \Delta R) \qquad (6)$$

Mathematical functions $f(\Delta C, \Delta R)$ and $g(\Delta C, \Delta R)$ are used to calculate the magnitude of adjustments for the LUT values $L_{xi}$ and $L_{yi}$ respectively, which will reduce the centering errors $\Delta C$ and $\Delta R$. The values $L_{xi}$ and $L_{yi}$ in the LUT's are replaced with the adjusted values $L_{xi}'$ and $L_{yi}'$ respectively. These adjusted LUT values are transmitted to the activity block 938 via line 964 and a first loop comprising the steps 938, 942, 946, 950, 954, 958, and 962 is re-executed until the image center is substantially coincident with the digital image center. When the image is centered, $\Delta C$ and $\Delta R$ are substantially equal to zero and control passes from decision block 958 via path 960 to activity block 968.

In block 968, the detector position is incremented by the amount $\Delta\theta$ to the next angular position ($\theta + \Delta\theta$). The new angular position of the detector is passed via path 970 to decision block 972 to determine if the new angle $\theta$ is greater than or equal to 360°. If $\theta$ is less than 360°, then control passes via path 974 to activity block 938. A second loop comprising the first loop and additional steps 968 and 972 is re-executed until the detector has completed one revolution, i.e., when $\theta$ is greater than or equal to 360°.

In a preferred embodiment, the angular increment $\Delta\theta$ is selected to be substantially larger than the angular increment $\Delta\theta$ between successive entries in the LUT's so that a calibration for a complete revolution can be calculated in a short period of time. For example, if the increment $\not=\theta$ is equal to 10°, then a complete revolution can be calculated with 35 executions of the second loop. The remaining LUT values corresponding to positions intermediate the 36 calculated positions are determined by interpolating between the adjacent calculated values as indicated in activity block 978. Control is then passed to activity block 982 via path 980 for random testing of the centering of the image.

In activity block 982, random angular positions are selected where the accuracy of the centering is determined. A centering error, ERR, is calculated which reflects the cumulative error of all of the selected positions. The centering error value is passed via path 984 to decision block 986 wherein the value is compared to zero or some other predetermined value. If ERR is not substantially zero, then control passes via path 988 to activity block 990.

In activity block 990, additional LUT values $L_{xi}$ and $L_{yi}$ which are located intermediate the first 36 values determined are empirically by re-executing the second loop for 36 additional values. For example, if the values determined in the first execution of the second loop were for the angles $\theta_1 = 0, 10, 20, 30, \ldots, 340$ and 350 degrees, then the intermediate angles determined in the second execution of the second loop would be $\theta_2 = 5, 15, 25, 35, \ldots, 345$ and 355 degrees.

A third loop comprising steps 978, 982, 986 and 990 is re-executed until the error value is substantially zero or until all of the LUT locations have been empirically determined. Control is then passed via path 994 to the end of the calibration procedure.

In a preferred embodiment, the total number of positions represented by the LUTs is approximately 16,000. The starting and stopping of the rotation of the electron beam indicated in blocks 938 and 942 between successive calibration locations serves at least two functions. First, excessive heating of the target anode on the X-ray tube is prevented by because the rotating electron beam does not strike any one spot on the anode for an extended period of time. Second, hysteresis effects in the steering coils are automatically compensated by continuous passage through complete hysteresis cycles. It will be understood that the above calibration procedure can either be performed manually under operator control or automatically under computer control.

Due to the finite amount of time required for the signals from the position encoder on the rotating detector to arrive at the LUT and the corresponding LUT values to drive the deflection coils on the X-ray tube, there may be a time differential or lag between the time the position of the rotating detector is sensed and transmitted to the LUT's and the time the corresponding deflection data is transmitted from the LUT's to the X-ray tube deflection coils. At very slow or zero rotation, this lag is insignificant. However, as the rotation rate increases, the lag becomes greater and greater. This lag may be compensated for by a phase offset inserted between the position encoder and the LUT. The optimum phase offset is determined by varying the offset while evaluating the focus of the image 830. For other than optimum offsets, the image will be blurred. The optimum offset will correspond to the sharpest image while the detector is rotating at a constant speed.

It will be understood that other calibration procedures may be used to synchronize the rotation of the X-ray source and detector.

COMPUTER CONTROL AND ANALYSIS SYSTEM

Figure 11:
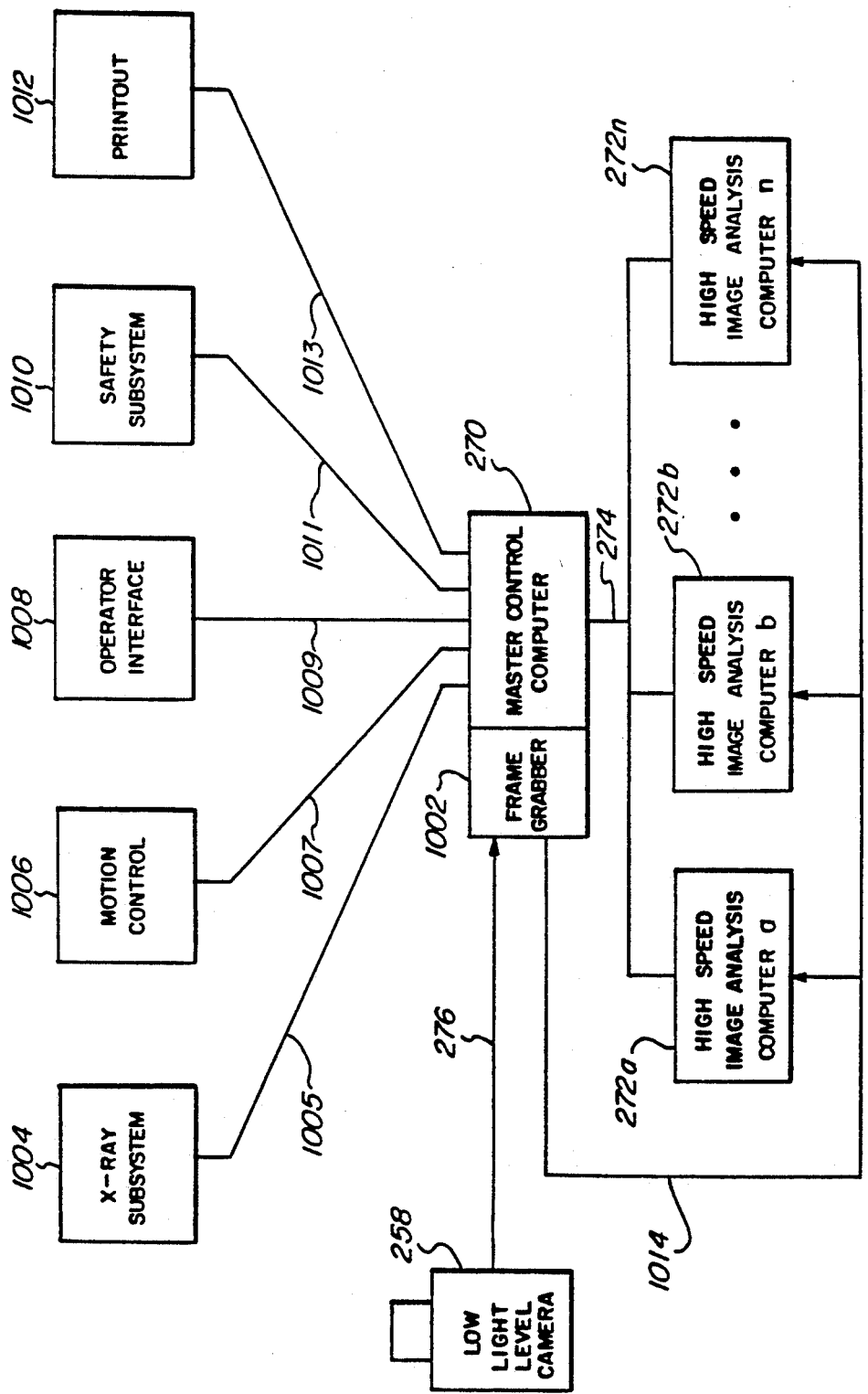
FIG. 11 is a block diagram of the computer control and analysis system.

FIG. 11 is a block diagram of the computer control and analysis system architecture for the automated laminography inspection system used in accordance with the present invention. The computer system is centered about the master control computer 270. A video frame grabber 1002 is incorporated into the computer 270 via a plug-in board. The low light level camera 258 is connected to master computer 270 via the line 276. A variety of subsystems, including X-ray 1004, motion control 1006, operator 1008, safety 1010, and printout 1012 communicate with the master computer via communication lines 1005, 1007, 1009, 1011 and 1013, respectively. Multiple high speed image analysis computers $272a, 272b, \ldots, 272n$, also called "analysis engines", communicate with the master computer via the data network 274. These communications take the form of "messages" that are passed between the master computer and the analysis engines via the data network 274. The analysis computers 272 also communicate with the frame grabber 1002 via a communication line 1014. In a preferred embodiment, each analysis computer 272 comprises a COMPAQ ® 386 processor board with an 80386 CPU, 5 megabytes of main RAM memory and a video frame grabber memory. The master computer 270 also comprises a COMPAQ ®386 processor board with an 80386 CPU. The analysis computers 272 are connected to the master computer 270 by a standard SCSI network.

In operation, the master computer 270 controls the operation of the inspection system through the various subsystems 1004 through 1012. The master computer also controls the acquisition and analysis of the laminographic images from which is derived a measure of the quality of the item under inspection. The master computer automatically controls the operation of the laminographic apparatus in two ways. First, a programmed sequence of movements is executed to acquire digital cross-sectional images. Second, a programmed analysis procedure automatically examines and interprets the digital cross-sectional images. The analysis of one image may be performed simultaneously with the acquisition of a second image. The analysis performed by the master computer system results in an output data listing which categorizes the various defects and other conditions that were detected in the item under examination.

Specifically, for the inspection of solder joints on printed circuit boards, as illustrated in FIGS. 3a and 3b, the computer controls the motion of the XYZ positioning table 230 to which the circuit board 210 is mounted. Often the area contained within one cross-sectional image, for example 0.400 inch×0.375 inch, is smaller than the total area of the circuit board or other item to be inspected. In this case, the item is logically represented by multiple XY fields of views which, when combined, include the total inspectable area of the circuit board. The master computer positions each XY field of view for inspection by issuing appropriate motion commands to the XYZ positioning table. After the first XY field of view is in position for inspection, the resulting cross-sectional image is acquired and integrated in the camera. The video signal of the image is then transmitted from the camera to the high speed image analysis computer 272. The circuit board may also be moved to specific Z locations in order to bring different planes of the solder joints into focus in the resulting cross-sectional images.

The preferred scan sequence for a circuit board is to collect all of the required Z level images for a fixed XY location, then move to the next XY location and collect all of the required Z level images for that location. This step and repeat sequence iterates until all necessary areas and levels of the board have been imaged and analyzed.

The fully automated inspection of all solder connections on a circuit board, performed under the control of the master computer, utilizes a preprogrammed inspection routine, custom tailored for the specific circuit board design being inspected. The board is scanned, and each solder connection is examined through the acquisition and analysis of cross-sectional images.

Figure 12:
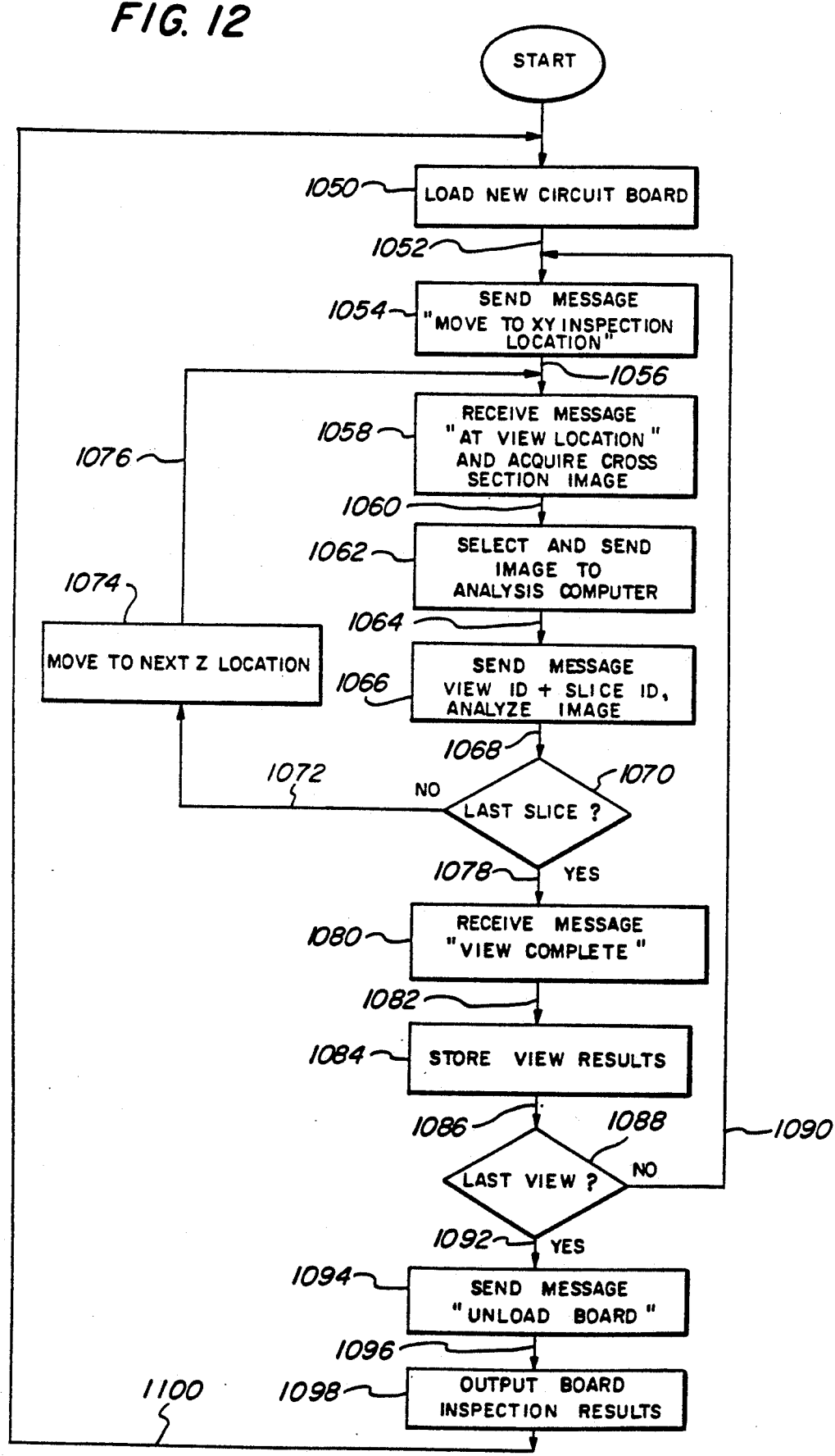
FIG. 12 is a schematic flowchart of the operation of the master control computer, showing the automated sequence of operations.

A flow chart illustrating the steps of this automated inspection routine is shown in FIG. 12. Beginning in activity block 1050, a circuit board for inspection is inserted into the load/unload port 292 of the laminographic apparatus (see FIG. 3c). Control is then transferred via path 1052 to activity block 1054 wherein the master computer sends a message to the XYZ positioning table which causes it to move the circuit board into the first XY view location.

Proceeding via path 1056, the routine enters a first loop comprising activity blocks 1058, 1062, 1066, 1070 and 1074. In activity block 1058, the master computer receives a message that the board is at the first view location. The master computer then controls the X-ray and detector subsystems such that a cross-sectional image of the board at that location is acquired. After the cross-sectional image is acquired, control passes via path 1060 to activity block 1062 wherein the previously acquired cross-sectional image is sent to one of the analysis computers.

Proceeding via path 1064 to activity block 1066, a message is received by the analysis computer which uniquely identifies the view and slice represented by the received image. The image is then analyzed by the analysis computer, while the master computer program proceeds via path 1068 to decision block 1070. In block 1070, the identity of the most recently acquired slice is checked to see if that is the last Z slice to be taken at that XY view location. If more Z slices are required, control passes via path 1072 to activity block 1074. In block 1074, the XYZ positioning table moves the circuit board in the Z direction thus positioning it for the next Z slice to be acquired. Control then proceeds via path 1076 back to activity block 1058. Another cross-sectional image is acquired in block 1058, which is sent to an analysis computer in block 1062, and identified and analyzed in block 1066. The first loop, comprising the steps 1058, 1062, 1066, 1070 and 1074, is repeated until it is determined in decision block 1070 that the last Z slice for the current XY view position has been acquired.

When the last Z slice has been acquired, control is transferred via path 1078 to activity block 1080 wherein a message indicates that the inspection of that particular XY view is complete. For example, if a particular XY view requires three different Z level slices, then the first loop will be executed three times, once for each Z level. At the completion of the third execution of the first loop, a message indicates that all data for that XY view has been acquired and analyzed.

Figures 13, 14:
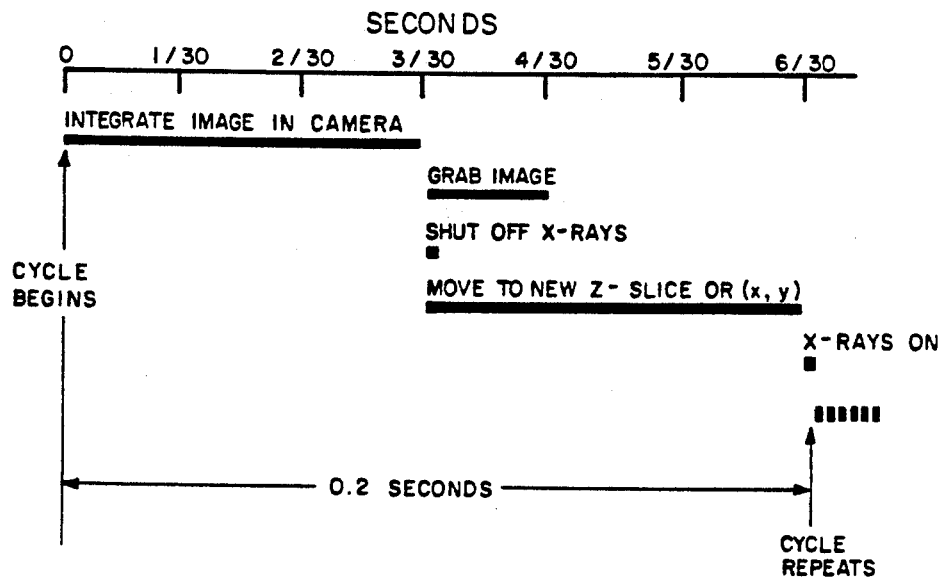
FIG. 13 a diagram of the timing cycle for the coordinated motion of the circuit board and the acquisition of multiple field of view images.
FIG. 14 is an example of an Inspection Report generated by the invention.

A timing diagram for the steps identified as the first loop is shown in FIG. 13. The unit of time chosen is one frame time, or 1/30 second, which is the rate at which the images are transmitted by the camera as video signals. At the start of the first loop cycle, the circuit board is positioned at the desired inspection location, the X-rays are on, and the camera begins to integrate the image for three frame times (0.1 second). During this 0.1 second, the turntable 256 and X-ray source 280 (FIG. 3a) make one complete revolution. During the next consecutive frame time, beginning at time 3/30 seconds, the image is "grabbed" from the camera 258 and sent to one of the image analysis computers 272 (FIG. 11). Meanwhile, the master computer 272 (FIG. 11) executes a first command which stops the production of X-rays (This is accomplished by directing the electron beam 285 into the beam stop 360 in FIG. 4.) and a second command which moves the circuit board to the next view area or slice position for acquisition of another image. This movement is typically completed within 0.1 second. During this 0.1 second, the circuit board is moved to the next position and stopped. The system is preferably designed so that any mechanical vibrations caused by the movement will be substantially dampened before the end of the 0.1 second time period. The computer then executes a command which causes X-ray production to resume and the cycle is repeated. Typical cycle time for the acquisition of a single image is therefore approximately 0.2 second, corresponding to a speed of five images per second.

Even though the time required by the computer to completely analyze an image may exceed the 0.2 second image acquisition cycle time, one embodiment of the laminographic apparatus still performs real time image processing by utilizing the parallel processing analysis computers 272 shown in FIG. 11. The parallel processing architecture enables the system to perform several different activities simultaneously. For example, the system may simultaneously analyze several different images while also acquiring additional images. Thus, the system does not need to wait for each image analysis to be completed before subsequent images can be acquired. The optimum number of analysis computers can be determined, based upon the complexity of the image analyses being performed, such that the image processing computing does not become a bottleneck in the inspection process.

Upon completion of an XY view in block 1080, control is transferred via path 1082 to activity block 1084, wherein the results for that particular XY view inspection are stored in the memory of the master computer. Proceeding via path 1086 to decision block 1088, the XY view identification is checked to determine if additional XY views of the circuit board are required.

If additional XY views are required, then control is transferred via path 1090 to activity block 1054. A second loop comprising steps 1054, 1058, 1062, 1066, 1070, 1074, 1080, 1084 and 1088 is executed multiple times until all of the programmed image locations on the circuit board have been acquired and analyzed.

When all of the programmed image locations have been inspected, control is transferred via path 1092 to activity block 1094 which indicates that the inspection is complete and it is time to unload the board.

Proceeding via path 1096 to activity block 1098, the inspection results for the previously inspected board are output in the form of an inspection report. Control then passes via path 1100 back to the beginning of the inspection routine at activity block 1050 and the system is ready to begin inspection of another circuit board.

An example of a typical inspection report is shown in FIG. 14. Various bookkeeping entries record the date and time 1102 of the inspection, the model number of the circuit board 1104 and the serial number of the specific board inspected 1106. Results of the inspection are tabulated in three columns which identify the device name 1108, the pin number where defects were identified 1110, and the type of solder defect identified 1112. In this particular example, it is seen that on a device identified as U13, there is a solder bridging defect between pins 2 and 3. Similarly, device R17 has insufficient solder at pin 1. The devices U13, R2, R17, etc. are typically electronic devices such as integrated circuit chips, resistors, capacitors, etc. Additionally, the inspection report may provide statistical summaries providing trend analysis of various defects and process control parameters. The inspection report may also include operation summaries showing the chronological history of the machine operation during some past period of time. The operation summaries may include a report of machine utilization factors including the identity of the operators; start times, stop times and dates for each operator's duty shift; and the number of boards processed during each shift.

The total time required to inspect an entire circuit board, utilizing the above described routine, is determined by several factors. Three of these factors are (1) the number of slices (cross-sectional images) at different Z levels needed for each XY view location, (2) the field of view size, i.e., the area covered by each individual image and (3) the size of the circuit board, i.e., the total area to be inspected.

A typical circuit board inspection may require anywhere from one to eight Z slices at each XY location, depending upon the complexity of the devices on the board and the type of solder connections. The field of view is the inspectable area acquired per image, and in one embodiment of the invention is approximately 0.400 inch by 0.375 inch. This field of view size results in high resolution images wherein each pixel has dimensions on the order of 0.0008 inch. Finally, the number of XY views and Z slices required to scan a particular circuit board, mosaic fashion, will determine the total number of views required and hence, the total amount of time required for the inspection.

For example, a 6"×9" circuit board (54 square inches), might have 50 square inches of area requiring inspection. At 0.15 square inches per field of view (0.400 inch times 0.375 inch), approximately 360 XY field of view locations are required to cover the entire board. Assuming, that an average of two Z slices are required at each location, this particular circuit board will require 720 images for a complete inspection. At the rate of five images per second, the total time required to inspect this board would be approximately 144 seconds.

Typical inspection times may range from 20 seconds for very simple circuit boards up to 8 minutes for larger, more complex boards requiring high resolution inspection.

AUTOMATED SOLDER CONNECTION DEFECT ANALYSIS

The laminographic apparatus used in accordance with the present invention is particularly well suited for performing automated inspections of the solder connections between electronic components mounted on circuit boards. In one embodiment, this is accomplished by acquiring high resolution X-ray cross-sectional images of the solder connections and analyzing the images by means of a computer controlled digital image processing procedure. There are presently a multitude of different types of solder connection defects which may be analyzed in this manner. However, the general concept of automated solder connection image analysis may be illustrated by a few illustrative examples. Such examples include bridging of solder between adjacent connection points, insufficient quantity of solder at a connection and missing solder at a connection.

Figure 15:
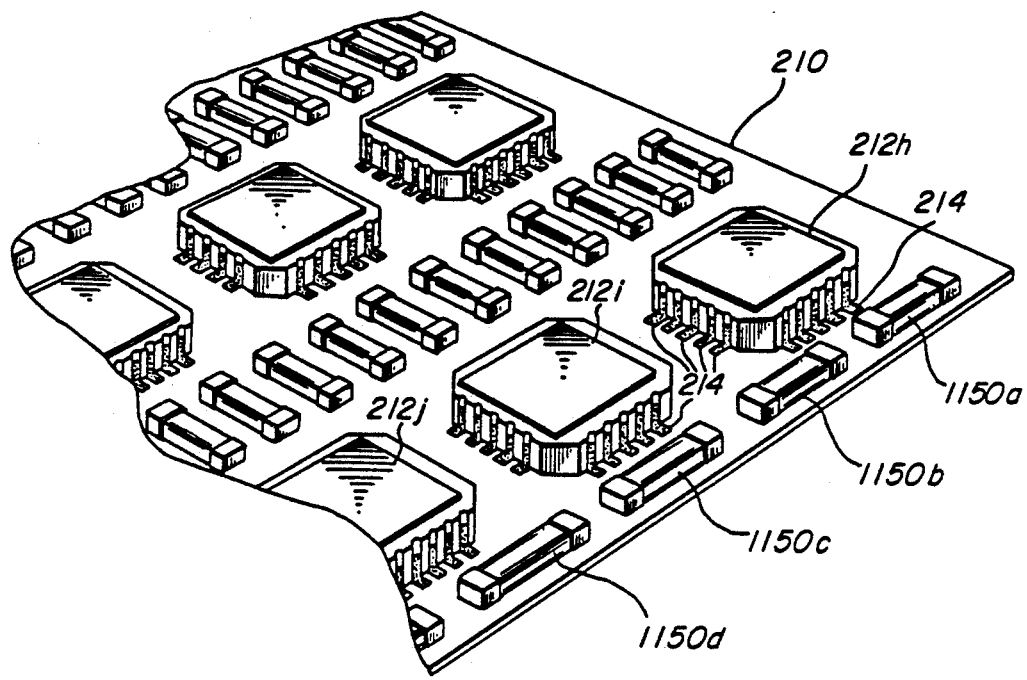
FIG. 15 shows a typical circuit upon which are located multiple electronic devices interconnected by multiple solder connections.

FIG. 15 shows a portion of a typical circuit board 210 upon which are located multiple electronic devices 212 and 1150 interconnected by multiple solder connections 214. In order to simplify the explanation of the automated analysis procedures, a specific type of electronic device and corresponding solder connection will be singled out for detailed discussion. However, it will be understood that the invention is not to be limited by the specific device chosen and that the invention applies to numerous other types of devices, technologies and electrical connections. Specifically, a device employing surface mount technology will be described in detail, however, the invention is also applicable to many other types of circuit board technologies including plated-through-hole technology.

Figure 16:
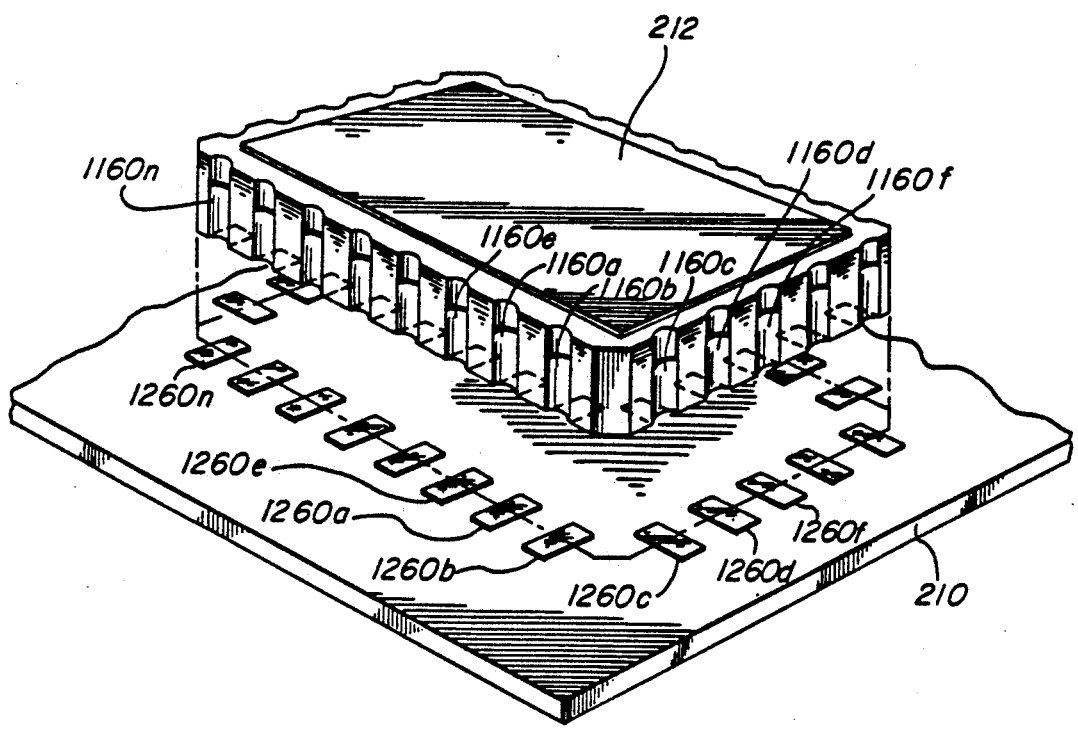
FIG. 16 shows a typical Leadless Chip Carrier device in position for mounting to a circuit board.

Surface Mount Technology (SMT) is a widely used technique wherein electronic devices comprising metallized connector pads are soldered to corresponding metallized connector pads on the surface of a circuit board. FIG. 16 illustrates a typical SMT device 212 shown in an elevated position over the mounting location on the circuit board 210 to which it will be connected. Specifically, the electronic device 212 comprises a package commonly used in the electronics industry and as known in the trade as a Leadless Chip Carrier (LCC). The LCC 212 comprises multiple metallized connector pads 1160a, 1160b, 1160c, . . . , 1160n which, when the LCC is located in position on the circuit board 210, are located immediately adjacent corresponding metallized circuit board connector pads 1260a, 1260b, 1260c,, . . . , 1260n, respectively. The metallized pads 1260 are formed on or near the surface of the circuit board 210 and provide the electrical connection points for interconnecting the various electronic devices 212 and 1150 comprising the completed circuit board assembly.

Figure 17:
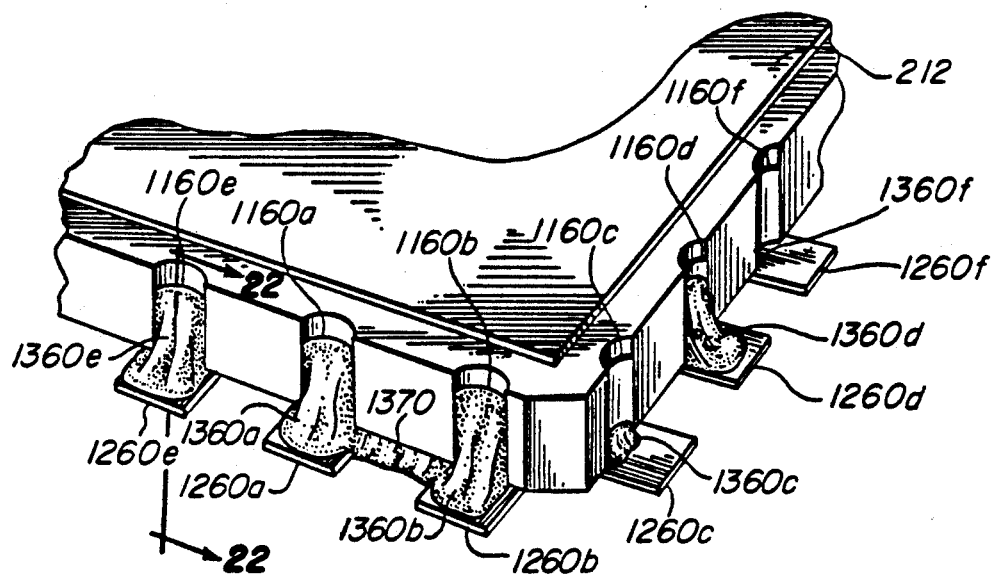
FIG. 17 shows examples of good and defective solder connections formed between an electronic device and a circuit board.

FIG. 17 is an enlarged view of a portion of the LCC 212 illustrating the general visual appearance of solder connections formed between the five metallized connector pad pairs 1160a/1260a through 1160e/1260e. Solder connection 1360e formed between pads 1160e and 1260e is an example of a good connection having no visible defects. A solder bridging defect 1370 is shown between adjacent solder connections 1360a and 1360b. A connection 1360c having insufficient solder is shown between pads 1160c and 1260c. A solder connection 1360d visually appears to have no defects but comprises internal voids. There is no solder shown at a connection 1360f between pads 1160f and 1260f.

Figure 18:
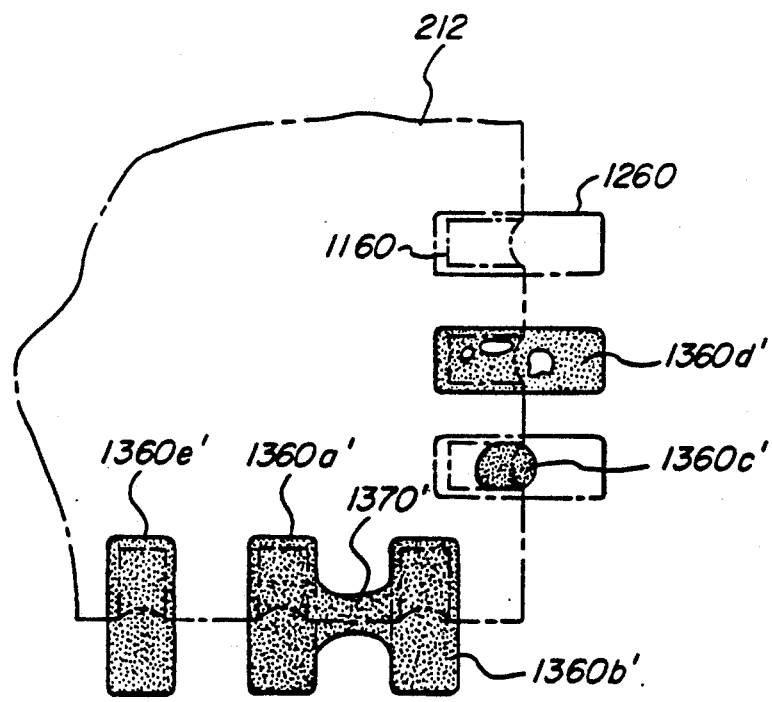
FIG. 18 shows a cross-sectional image of the solder connections in FIG. 17.

FIG. 18 illustrates the appearance of an X-ray cross-sectional image of the portion of the LCC device 212 shown in FIG. 17. The plane shown by the cross-sectional image is parallel to the plane defined by the circuit board 210 and approximately 0.0005 inch above the surface of the circuit board. The phantom lines indicating the location of the device 212, device connection pads 1160 and circuit board connection pads 1260 are shown for reference purposes only and may not be present in an actual cross-sectional image. Image regions 1360a', 1360b', 1360c', 1360d', 1360e' and 1370' correspond to the solder connections 1360a, 1360b, 1360c, 1360d, 1360e and defect 1370, respectively, in the designated image plane.

POSITIONAL DATA ACQUISITION

In order to analyze a given circuit board for solder joint defects, it is often desirable to obtain precise coordinates for the locations of the solder joints to be inspected. In one embodiment, the present invention employs a positional data acquisition procedure to precisely determine the location of the solder joints to be inspected.

A computer aided design (CAD) data file within the master computer 270 contains design data for the circuit board to be inspected. For example, included in the CAD data are the positional coordinates and physical dimensions of each joint on a given circuit board, as well as the component type connected at a given joint. Thus, using the CAD data file, the position of each solder joint to be inspected can be determined. However, due to positional inaccuracies in the movement of the multi-axis positioning table 230, as well as dimension changes of the circuit board 210 due to thermal expansion and contraction, and dimensional variance from board to board, the coordinates stored within the CAD data file do not always exactly match the actual positions of the solder joints on a board. Therefore, there may be a slight positional deviation of the actual position of a given solder joint from the position given by the CAD data for that solder joint.

In order to correct for the slight positional deviations between the coordinates of the solder joints as originally stored in the data file, and the actual locations of the solder joints, the positional data acquisition procedure is run before each analysis. The positional data acquisition procedure initially causes the positioning table 230 to move to the location given by the CAD data for the solder joint to be inspected. For example, the CAD data location of a solder joint to be inspected may be given as a pair of X-Y coordinates which defines the location of the centroid of the solder joint conducting pad.

The positional data acquisition procedure is then used to perform an analysis on a region around the CAD data coordinates to determine the actual location of the contact pad. The analysis employs a conventional doughnut operator to determine the centroid of the contact pad.

An example of a conventional doughnut operator is shown in dashed lines in FIG. 25a. Typically, a doughnut operator includes a "hole" portion (corresponding to the region occupied with ones), and a "ring" portion (corresponding to the region occupied with negative ones). Also shown in FIG. 25a, to the right of the doughnut operator, is a diagrammatic representation of an image region containing a contact pad. Each value within the image region representation corresponds to a gray scale value of a pixel within the region. Note that the region representing the background contains gray scale values of 50 while the region representing the contact pad contains gray scale values ranging from 170 to 200. Also note that the image region representation shown in FIG. 25a is simplified to facilitate illustration of the positional data acquisition method. In practice, the contact pad will be on the order of 100 pixels in length and width, and the background values will not necessarily have a constant value (e.g., 50) in the immediate vicinity of the contact pad. In order to determine the centroid of the pad region, a convolution of the doughnut operator with the pad section of the image is performed as described below.

Figure 25B:
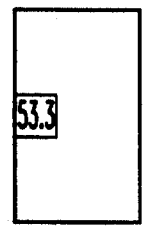

FIG. 25b shows the doughnut operator (in dashed lines) overlaid onto the image region. In order to accurately determine the centroid of the contact pad, the doughnut operator should have a "hole" portion of substantially the same shape and dimensions as the contact pad (e.g., 3 pixels by 5 pixels in this example). It can be seen in FIG. 25b that a portion of the image region corresponding to the contact pad falls within the doughnut "hole," and another portion of the region corresponding to the contact pad falls within the "ring" region of the doughnut operator. It can also be seen from FIG. 25b that some portions of the background region fall within the "hole" portion of the doughnut operator, while other portions of the background fall within the ring portion of the doughnut operator. The doughnut operator acts to transform the values within the image region by averaging the values within the "ring" portion, and subtracting that value from the average of the values within the "hole" portion. The transformed value is then stored and assigned to the coordinates of the pixel corresponding to the center of the doughnut operator in the image region. In the example shown in FIG. 25b, the average of the "hole" portion is 137.3 (2060/15), and the average of the "ring" portion is 84 (1680/20). Thus, the transformed value, 53.3 (137.3−84), is stored and assigned the coordinates corresponding to the center pixel of the doughnut operator.

Figure 25C:
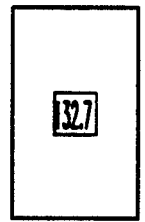
Figure 25D:
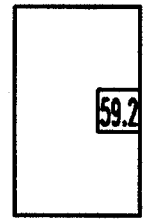

The doughnut operator scans across the entire region of the contact pad (usually from top to bottom and left to right), using the original CAD data location of the pad as a reference location from which to initiate scanning. For example, FIGS. 25b, 25c, and 25d show the doughnut operator scanning across the middle row of the contact pad region. Thus, a transformation value is produced for every pixel within the contact pad region as shown in FIG. 25e. The transformed values along with their coordinates are stored, and the highest transformed value is chosen as the new centroid location of the contact pad. Note that the highest transformed value is typically obtained when the contact pad region is contained entirely within the "hole" portion of the doughnut operator as shown in FIG. 25c. The dimensions of the pad (i.e., the pad width and length) remain the same as the pad dimensions originally stored within the CAD data file, and the new contact pad positional data is stored within a dynamic data file.

IMAGE ANALYSIS FOR DETECTION OF SOLDER BRIDGING DEFECTS

Figure 19:
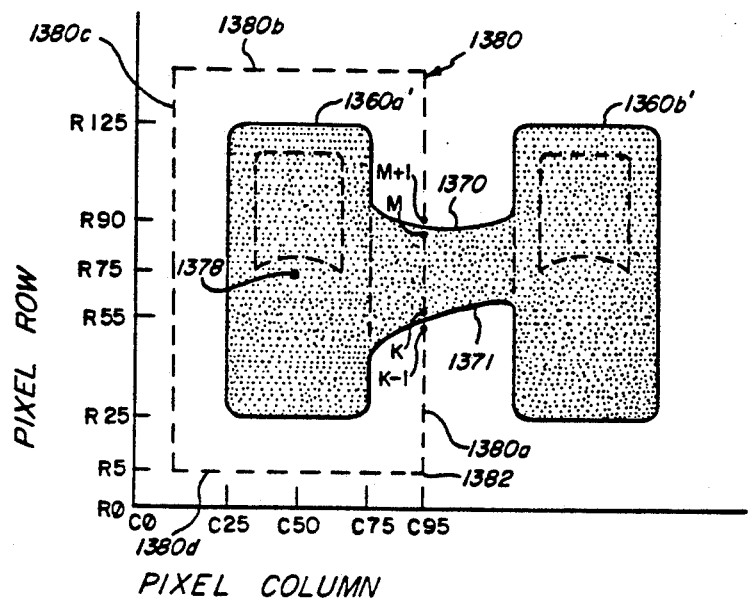
FIG. 19 illustrates the procedure for automatically locating and identifying a solder bridging type defect.

A solder bridging defect is the presence of unwanted solder between traces on a circuit board, between a connection pad and a trace, between two separate connection pads, or between two separate connection pins. An enlarged portion of FIG. 18 at the location of the bridging defect image 1370' between connection pads 1260a and 1260b is shown in FIG. 19. An arbitrary pixel grid comprising columns and rows is also shown to aid in the description of the automated procedure for detecting bridging defects.

Each pixel in the image is associated with an intensity value which corresponds to the optical density of the image represented by that pixel. The intensity values form a gray scale which ranges from zero (black) to 255 (white). The images of high density materials which readily attenuate X-rays, e.g., solder, are represented by relatively low intensity values corresponding to the darker shades of gray near the black end of the gray scale. Conversely, low density materials, e.g., plastic circuit boards, produce images having intensity values corresponding to the lighter shades of gray near the white end of the gray scale. Images having this type of gray scale are known as "positive" images. It will be understood that the relationship between shades of gray and intensity may be reversed to produce what are commonly known as "negative" images. Either negative or positive images may be used in the invention, but for purposes of explanation, negative images will be used. Therefore, pixels within the regions of the image representing solder material, e.g., regions 1360' and 1370', correspond to relatively high gray levels. Pixels in other regions of the image represent lower density materials, e.g., plastic circuit board, and correspond to relatively low gray levels.

The initial step in the image analysis comprises acquiring topographical data and inspection parameters necessary for performing an inspection and evaluation of a solder bridging defect. In one embodiment of the invention, a data file contains this specific information for each image analysis being performed. Once the circuit board is identified, the data file for that specific type of board is recalled and placed in the analysis computer(s) memory. An algorithm for analyzing an image for the presence of a bridging solder defect uses as input, the centroid location and boundaries of the circuit board connection pad 1260, a predetermined search path location and a predetermined differential gray value threshold. For the example shown in FIG. 19, the data file will contain the information that the centroid 1378 of connection pad 1260a is located at column and row pixel coordinates (C50,R75). Additionally, the data file will contain the information that the pixel width of pad 1260a is the difference between pixel column numbers C75 and C25 and that the pad length is the difference between pixel row numbers R125 and R25. Any other inspection parameters, such as the differential gray value threshold and search path location and dimensions, necessary for performing the bridging solder defect analysis will also be retrieved from the data file.

The procedure for analyzing the cross-sectional X-ray image of a solder connection for a solder bridging defect is illustrated in FIG. 19 with respect to solder connection 1360a'. Preferably, the plane of the cross-sectional image lies in a plane which is substantially parallel to the circuit board plane and is approximately 0.0005 inch above the surface of the circuit board. The procedure generally comprises determining, from the image, the presence of unwanted solder along a search path which completely surrounds the solder connection of interest.

Using the topographical data for pad 1260a, an analysis algorithm proceeds to define a search path 1380 around the boundaries of the pad comprising path segments 1380a, 1380b, 1380c and 1380d. The search path is one pixel in width and is positioned at a predetermined distance from the boundaries of the pad. In the embodiment wherein a digital image comprises 512 columns and 480 rows and corresponds to an area on the circuit board of approximately 0.400 inch × 0.375 inch, one pixel width corresponds to a distance of approximately 0.00078 inch on the circuit board. The predetermined distance between the pad boundaries and the search path in FIG. 19 is the difference between pixel columns C95 and C75 and the difference between pixel rows R5 and R25. The predetermined distance may be selected empirically to meet the requirements of any particular analysis application.

The image intensity of each pixel comprising the search path 1380 is compared to the intensity of the adjacent pixels in the search path to determine a differential gray value $\Delta G$. The image intensity or gray value of a particular pixel is given by $I_{C,R}$. The differential gray value $\Delta G_{1,2}$ between two adjacent pixels 1 and 2 is then found by taking the difference between their respective intensities $I_1$ and $I_2$. Each differential gray value $\Delta G_{1,2}$ is then compared to a predetermined threshold value $\Delta G_{Th}$. The threshold value is selected to indicate when one pixel is located in a solder portion of the image and the adjacent pixel is located in a circuit board portion of the image. The presence of unwanted solder along the search path is indicated when a differential gray value exceeds the threshold value.

By way of example, consider a search beginning at a corner 1382 of the search path 1380 located at a first pixel (C95,R5) having an intensity $I_1$ and proceeding up column C95 to the next adjacent pixel on path segment 1380a to a second pixel (C95,R6) having an intensity $I_2$. It is to be understood that this starting position is arbitrary and that any other position along the search path could also be chosen to begin the search. The differential gray value for these first two adjacent pixels is given by $$\Delta G_{1,2} = I_1 - I_2 = I_{C95,R5} - I_{C95,R6} \qquad (7)$$

If the absolute value of the differential gray value $|\Delta G_{1,2}|$ is greater than or equal to the threshold value $\Delta G_{Th}$, then the location of the pixels and the sign, i.e., positive or negative, of the differential gray value are stored as candidate defect indications $D_i$, where i is an integer corresponding to the order in which the defect indication was found. For example, $D_1$ corresponds to the first defect indication encountered along the search path 1380 from the starting position 1382, $D_2$ corresponds to the second defect indication encountered and so on.

In the example shown in FIG. 19, a first defect indication $D_1$ is found at a pixel K, located approximately at (C95,R55). If pixel K is in the solder defect 1370' portion of the image, then the previous pixel K-1 in the search path, located approximately at (C95,R54), is approximately outside the solder portion and will have a higher intensity value than the pixel K. Therefore, an appropriately selected $\Delta G_{Th}$ will be smaller than the absolute value of a differential gray value $|\Delta G_{K-1,K}|$ derived from the intensities $I_{K-1}$ and $I_K$ of these two adjacent pixels K−1 and K. Additionally, $\Delta G_{K-1,K}$ is positive in sign. Similarly, a second defect indication $D_2$ is found at a pixel M located approximately at (C95,R90). If pixel M is in the solder defect 1370' portion of the image, then the subsequent pixel M+1 in the search path, located approximately at (C95,R91), is outside the solder portion and will have a higher intensity value than the pixel M. Therefore, the absolute value of a differential gray value $|\Delta G_{M,M+1}|$ derived from the intensities $I_M$ and $I_{M+1}$ of these two adjacent pixels M and M+1 is greater than $\Delta G_{Th}$. Additionally, $\Delta G_{M,M+1}$ is negative in sign. The presence of the bridge defect 1370' is thus revealed when defect indication $D_1$ is positive and the next defect indication $D_2$ is negative.

The search for defect indications continues around the path 1380 until the entire path has been examined. A report of all the bridges found is then recorded and reported.

Figure 20A:
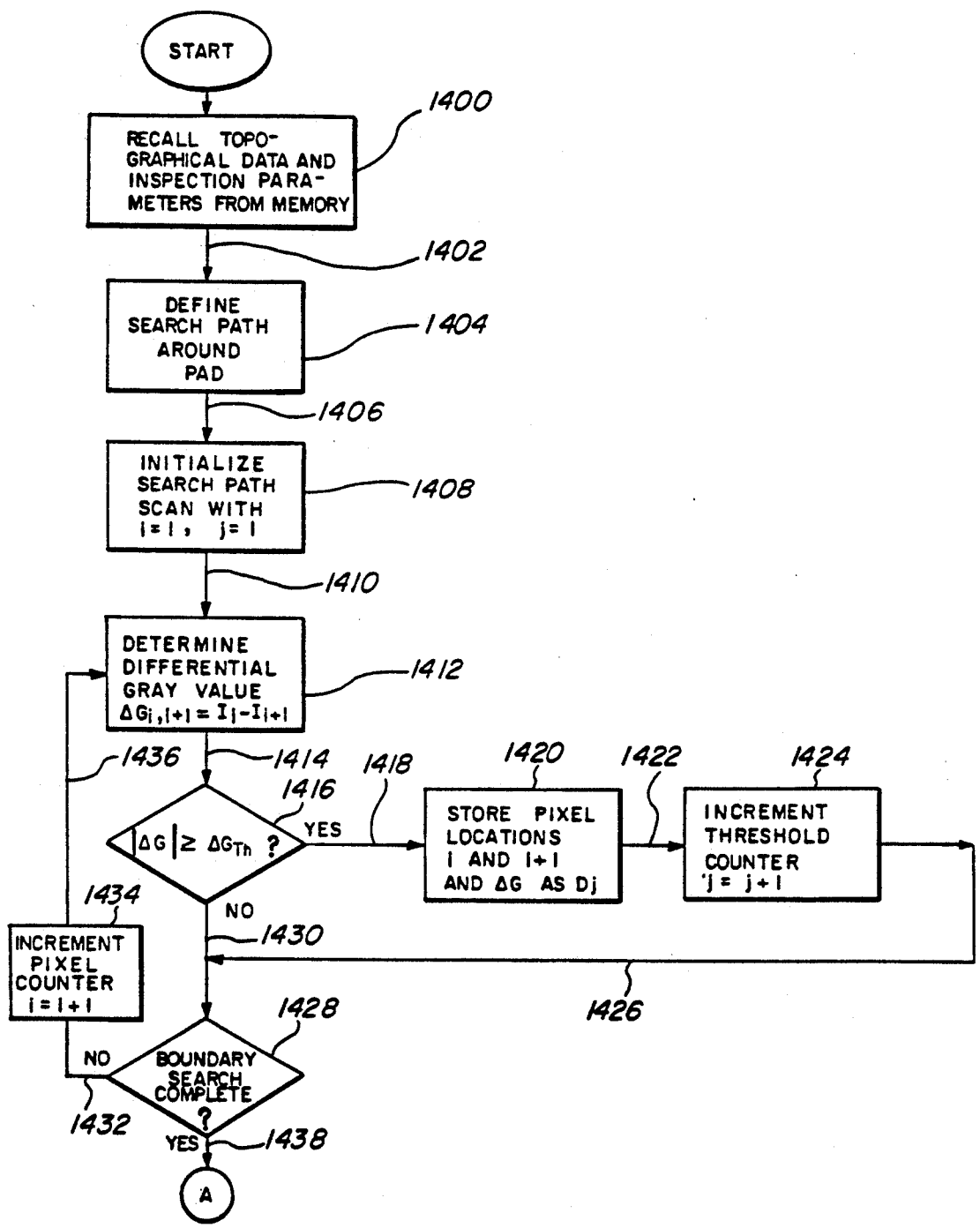
FIG. 20a is a flowchart illustrating the process for automatically locating and identifying a solder bridging defect.
Figure 20B:
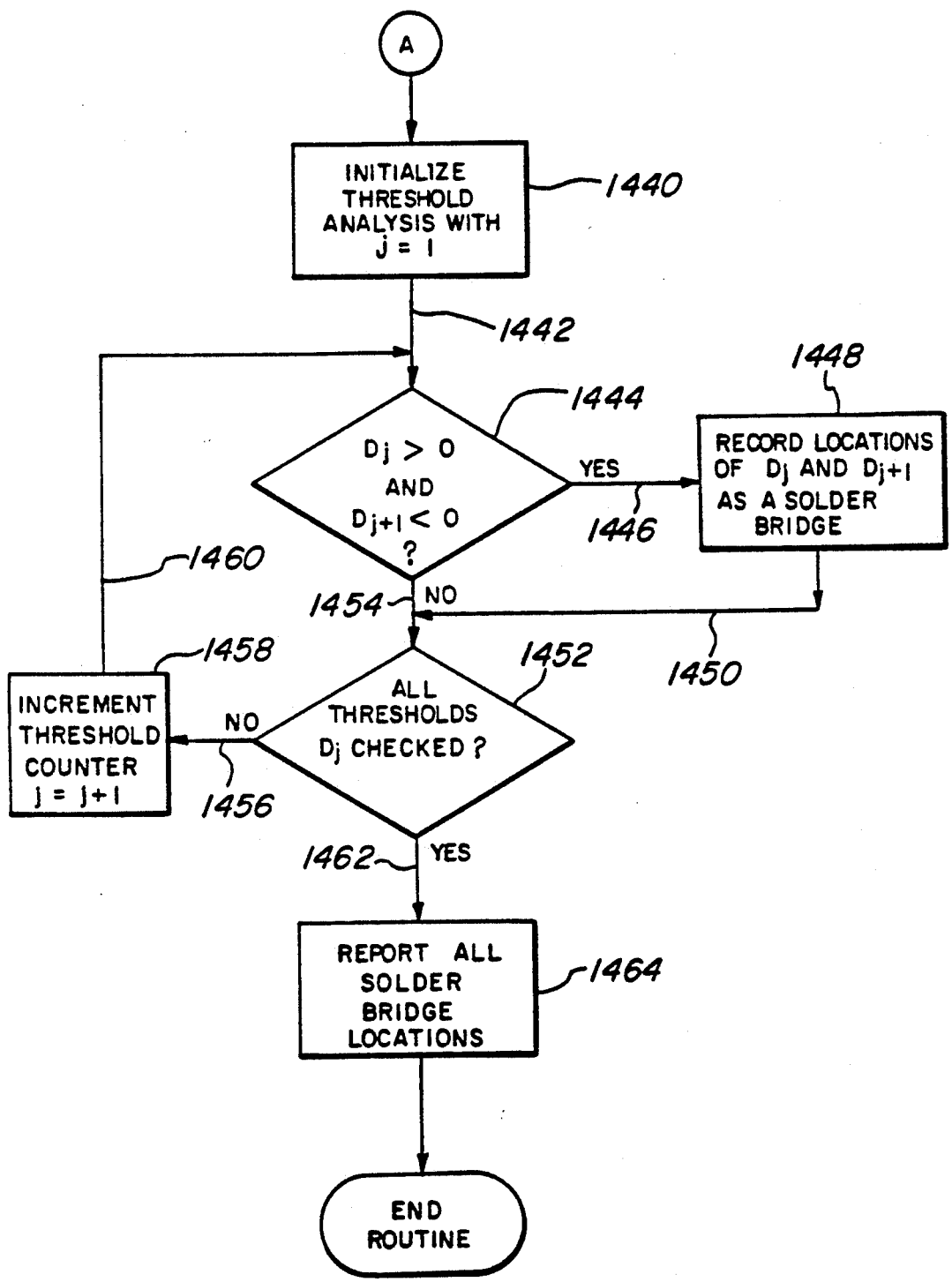

A flowchart illustrating the process for automatically locating solder bridging defects is shown in FIG. 20. Beginning in an activity block 1400, the topographical data and other inspection parameters for the particular connection pad being analyzed are recalled from the analysis computer's memory. Proceeding via a path 1402 into an activity block 1404, the search path around the connection pad is defined utilizing the topographical data and other inspection parameters stored in the memory of the computer. Control is then transferred via a path 1406 to activity block 1408 wherein the search path scan is initialized by setting a pixel counter "i" and a defect indication counter "j" equal to one.

A first loop comprising activity blocks 1412, 1416, 420, 1424, 1428 and 1434 is entered via a path 1410 from activity block 1408. In the first loop, every pixel comprising the search path is examined, differential gray values are calculated and candidate defect locations are identified and stored for further processing at a later time. In the first activity block 1412 of the loop, the differential gray value $\Delta G_{1,2}$ for the first and second pixels in the search path is calculated. This value is passed via a path 1414 to a decision block 1416 wherein the absolute value of the differential gray value $|\Delta G_{1,2}|$ is compared to the predetermined threshold value $\Delta G_{1,2}$. If $|\Delta G_{1,2}|$ is greater than or equal to $\Delta G_{Th}$, control passes via a path 1418 to activity block 1420. In activity block 1420, the locations of pixels 1 and 2 and the sign of $\Delta G_{1,2}$ are stored as a first defect indication $D_1$. Control passes to activity block 1424 via a path 1422 wherein the defect counter "j" is incremented by one. In a decision block 1428, the final block of the first loop, reached via a path 1426, a completion check is performed to determine if the entire search path has been examined. If not, control passes via a path 1432 to activity block 1434, wherein the search path pixel counter "i" is incremented by one. Control then returns via path 1436 to the beginning of the first loop at activity block 1412. The first loop is repeated until all of the pixels comprising the search path have been analyzed, at which time control passes out of the first loop from decision block 1428 via path 1438 to activity block 1440.

In activity block 1440, the defect counter "j" is again initialized to the value one prior to entering a second loop via path 1442. The second loop comprises blocks 1444, 1448, 1452 and 1458. In the second loop, the defect indications $D_j$, identified in the first loop, are examined to determine the locations of solder bridging defects along the search path. Entering the second loop at decision block 1444 with j=1, the signs of defect indications $D_1$ and $D_2$ are determined. If $D_1$ is positive and $D_2$ is negative, then control passes via path 1446 to activity block 1448 wherein the locations of $D_1$ and $D_2$ are recorded and a solder bridging defect is recorded at the search path segment between $D_1$ and $D_2$. Control then passes via path 1450 to a decision block 1452 where a completion test is performed to determine if all of the defect indications $D_j$ have been analyzed. If not, control passes via path 1456 to an activity block 1458 where the defect counter "j" is incremented by one. Control then returns via path 1460 to the beginning of the second loop at decision block 1444. The second loop is repeated until all of the defect indications $D_j$ located along the search path in the first loop have been analyzed for the solder bridging defect. Control then passes out of the second loop from decision block 1452 via path 1462 to activity block 1464. In block 1464, a report of all the solder bridging defects found along the search path is generated and stored for later recall.

IMAGE ANALYSIS FOR DETECTION OF MISSING OR INSUFFICIENT SOLDER DEFECTS

Figure 21:
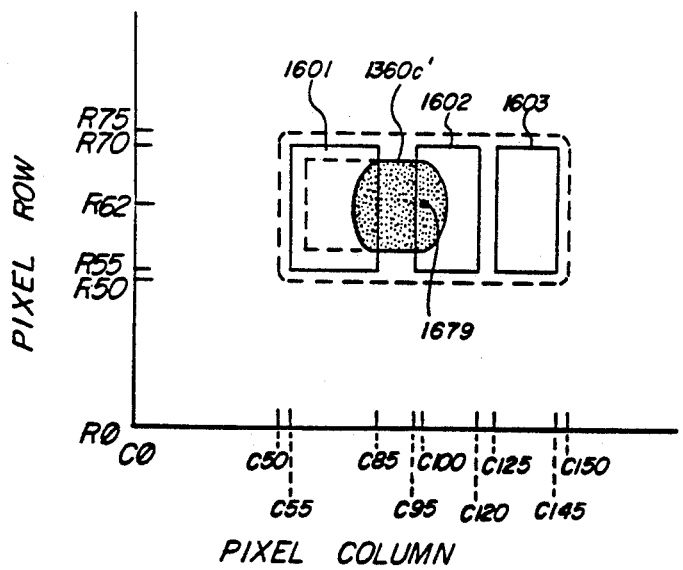
FIG. 21 illustrates the procedure for automatically locating and identifying a solder connection having insufficient solder.

A missing solder defect is defined as the presence of substantially zero or very small quantities of solder at a connection comprising an electronic device connection pad and a corresponding circuit board connection pad. An insufficient solder defect is defined as some solder present at the connection, but not enough to form a proper fillet or to provide sufficient strength to the connection. An enlarged portion of FIG. 18 at the location of the insufficient solder defect image 1360c' between connection pads 1160c and 1260c for a Leadless Chip Carrier (LCC) is shown in FIG. 21. An arbitrary pixel grid comprising columns and rows is also shown to aid in the description of the automated procedure for detecting missing or insufficient solder defects.

A procedure for analyzing the cross-sectional X-ray image of a solder connection for a missing solder or insufficient solder defect is illustrated in FIG. 21 with respect to LCC solder connection image 1360c'. Preferably, the plane of the cross-sectional image lies in a plane which is substantially parallel to the circuit board plane and is approximately 0.0005 inch above the surface of the circuit board. The procedure generally comprises determining, from the image, the thickness of the solder connection in several specific regions.

Figure 22:
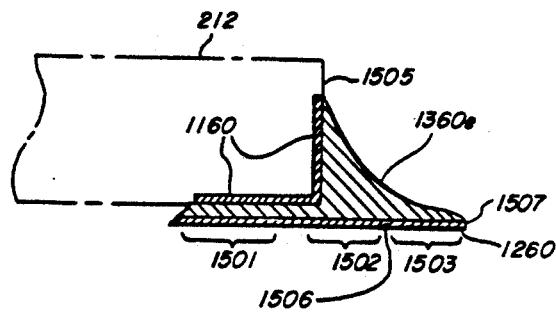
FIG. 22 is a cross-sectional view of a typical good solder connection illustrating three regions of the connection.

Three specific regions of a solder connection are defined in reference to FIG. 22. FIG. 22 is a cross-sectional view of a typical good LCC solder connection, such as connection 1360e. The cross-sectional view is along the line 22—22 in FIG. 17. A first region 1501 of the connection 1360e, sandwiched between the device connection pad 1160 and circuit board connection pad 1260, is designated the "pad" of the connection. A second region 1502, beginning approximately at a side wall 1505 of the device 212 and extending approximately to a point 1506 between the wall 1505 and a border 1507 of the pad 1260, is designated the "heel" portion of the connection 1360e. A third region 1503, beginning approximately at the point 1506 and extending approximately to the border 1507 of the pad 1260, is designated the "toe" portion of the connection 1360e.

Typically, the pad region 1501 comprises a nearly uniform thickness of solder which is relatively thin. The heel region 1502 is generally of non-uniform thickness and comprises the thickest portion of the connection. The toe region 1503 is generally more uniform in thickness than the heel, but is not as thick. The amount of solder comprising the connection 1360e can be estimated from measurements of the average thickness of the solder in each of the three regions 1501, 1502 and 1503.

Figure 23A:
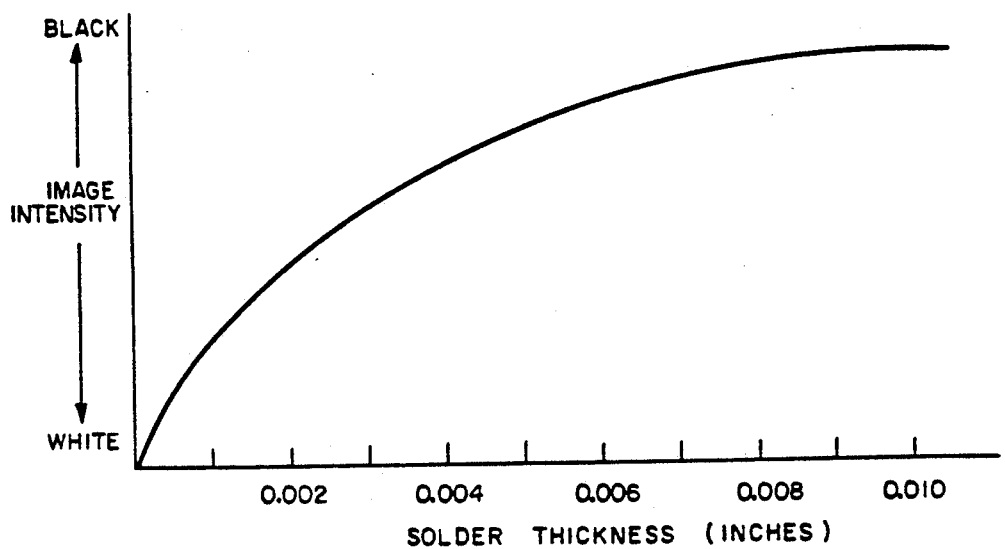
FIG. 23a is a graphical representation of the image intensity versus solder thickness for a cross-sectional image of solder material.

In a laminographic cross-sectional image of solder material, typically a combination of lead and tin, there is a relationship between the intensity of the image and the thickness of the solder material forming the image. FIG. 23a illustrates an example of this general relationship. In this example, it is seen that the image intensity increases from values corresponding to lighter shades of gray (white) to values corresponding to darker shades of gray (black) as the thickness of the solder material increases. That is, the image of a thin section of solder will have a gray level that is less than the gray level of the image of a thicker section of solder. The image of the thin section will appear to be a lighter shade of gray than the image of the thicker section.

Figure 23B:
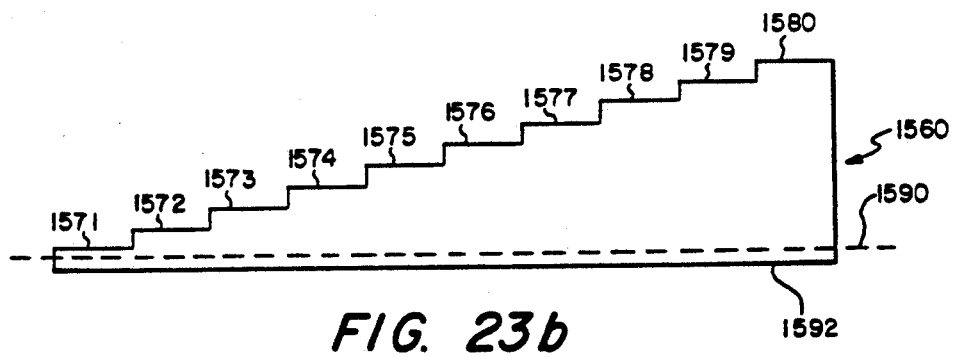
FIG. 23b shows a calibration step wedge used for calibrating the image intensity versus thickness relationship.
Figure 23C:
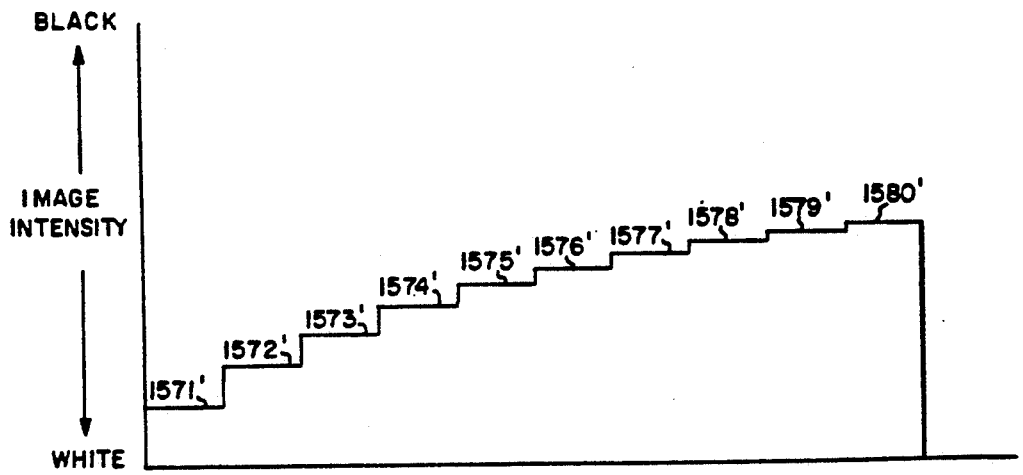
FIG. 23c is a graphical representation of the image intensity versus thickness relationship for the calibration step wedge shown in FIG. 23b.

This relationship may be calibrated by using a calibration step wedge comprising multiple steps of differing thickness. An example of such a step wedge 1560 is shown in FIG. 23b. Step wedge 1560 is constructed of solder material and comprises ten steps 1571 through 1580 having thicknesses ranging from 0.001 inch to 0.010 inch in increments of 0.001 inch. It is possible to construct the step wedge 1560 with other dimensions (e.g., in 2 mil increments from 2 mils to 20 mils, etc.), depending upon the thicknesses of the solder joints and the type of circuit board that is to be inspected. An X-ray laminographic cross-sectional image of the step wedge 1560 taken at a plane including the line 1590 and parallel to a base 1592 of the wedge exhibits the image intensity versus solder thickness relationship shown in FIG. 23c. Since the thicknesses of the steps 1571 through 1580 are known, the corresponding intensities 1571' through 1580' may be compared to intensities of other cross-sectional images of solder material where the thicknesses are not known to determine the unknown thicknesses. (Although this is one method of calibrating the solder thicknesses of the step wedge to correspond to various image intensities, alternative methods can be used. Such an alternative method is described below in relation to FIGS. 23d and 23e.)

The initial step in the analysis for the detection of missing or insufficient solder comprises acquiring topographical data and inspection parameters. One embodiment of the invention provides this specific information in a data file for each analysis to be performed. One method for analyzing an image for the presence of a missing or insufficient solder defect uses as input, the centroid location and boundaries of the connection pad, locations of three inspection windows and six threshold values. In the example shown in FIG. 21, the data file will contain the information that the centroid 1679 of connection pad 1260c is located at column and row pixel coordinates (C100,R62) in FIG. 21. Additionally, the data file will contain the information that the pixel length of pad 1260c is the difference between pixel column numbers C50 and C150 and that the pad width is the difference between pixel row numbers R75 and R50. Any other inspection parameters necessary for performing the analysis will also be retrieved from the data file.

Using the topographical data and inspection parameters for a missing or insufficient solder defect analysis of the image 1360c' at pad 1260c, the image analysis algorithm proceeds to define the boundaries of three inspection windows 1601, 1602 and 1603, shown in FIG. 21. Each window is rectangular in shape and is positioned at a predetermined distance from the boundaries and centroid of the pad. The first window 1601 is defined by four corners having pixel coordinates (C55,R55), (C55,R70), (C85,R70) and (C85,R55). Window 1601 substantially overlaps the pad region 1501 of the solder connection. The second window 1602 is defined by four corners having pixel coordinates (C95,R55), (C95,R70), (C120,R70) and (C120-,R55). Window 1602 substantially overlaps the heel region 1502 of the solder connection. The third window 1603 is defined by four corners having pixel coordinates (C125,R55), (C125,R70), (C145,R70) and (C145,R55). Window 1603 substantially overlaps the toe region 1503 of the solder connection.

The average image intensity within a window is determined by summing the image intensities of all of the pixels comprising the window and dividing by the total number of pixels contributing to the sum. The average intensities thus derived from the pad region window 1601, the heel region window 1602 and the toe region window 1603 are designated $I_P$, $I_H$ and $I_T$, respectively. These average intensities, as previously discussed, are directly related to average thickness $T_P$, $T_H$, and $T_T$ of the solder in each of the respective regions. The presence of a missing or insufficient solder defect is determined by comparing these average thicknesses $T_P$, $T_H$, and $T_T$ to predetermined thickness threshold values $Th_{M,P}$, $Th_{M,N}$, $Th_{M,T}$, $Th_{I,P}$, $Th_{I,H}$, and $Th_{I,T}$. Generally, the missing solder threshold values, $Th_{M,P}$, $Th_{M,H}$ and $Th_{M,T}$, corresponding to the pad, heel and toe regions respectively, are smaller than the insufficient solder threshold values, $Th_{I,P}$, $Th_{I,H}$, and $Th_{I,T}$. That is, $Th_{M,P} < Th_{I,P}$, $Th_{M,N} < Th_{I,H}$ and $Th_{M,T} < Th_{I,T}$. Specifically, if $T_P < Th_{M,P}$, $T_H < Th_{M,H}$ and $T_T < Th_{M,T}$, then the connection is reported as having missing solder. If $Th_{M,P} < T_P < Th_{I,P}$, $Th_{M,H} < T_H < Th_{I,H}$ and $Th_{M,T} < T_T < Th_{I,T}$, then the connection is reported as having insufficient solder.

Figure 24:
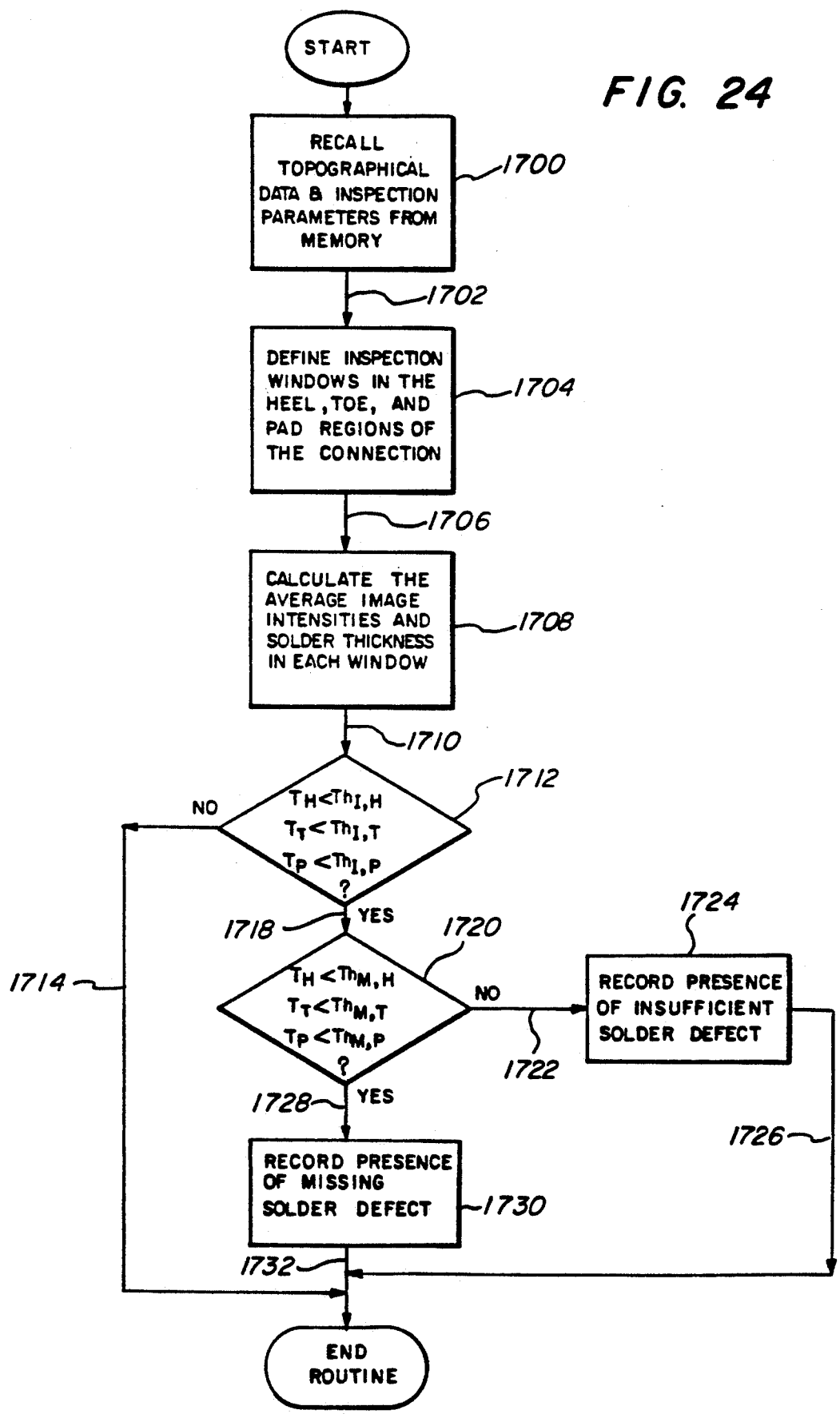
FIG. 24 is a flowchart illustrating the process for automatically locating and identifying a solder connection having missing or insufficient solder.

A flowchart illustrating the process for automatically locating missing or insufficient solder defects is shown in FIG. 24. Beginning in an activity block 1700, the topographical data and other inspection parameters for the particular connection pad being analyzed are recalled from the analysis computer's memory. Proceeding via a path 1702 into an activity block 1704, inspection windows for the pad, heel and toe regions of the solder connection are defined utilizing the topographical data and other inspection parameters stored in the memory of the computer. Control is then transferred via a path 1706 to activity block 1708 wherein the average image intensity within each window is determined and the corresponding average solder thickness is calculated. Control is then transferred to decision block 1712 via path 1710.

In decision block 1712, the average solder thicknesses $T_P$, $T_H$, and $T_T$ within the windows are compared to the insufficient solder thickness threshold values $Th_{I,P}$, $Th_{I,H}$, and $Th_{I,T}$ respectively. If the average thicknesses are not less than the insufficient solder thresholds, control passes via path 1714 to the end of the analysis routine. If the average thicknesses are less than the insufficient solder thresholds, control passes via path 1718 to decision block 1720. In decision block 1720, the average thicknesses $T_P$, $T_H$, and $T_T$ are compared to the missing solder thickness threshold values $Th_{M,P}$, $Th_{M,H}$, $Th_{M,T}$ respectively. If the average thicknesses are not less than the missing solder thresholds, control passes via path 1722 to activity block 1724 wherein the presence of an insufficient solder defect is recorded. Control then passes via path 1726 to the end of the analysis routine. If the average thicknesses are less than the missing solder thresholds in decision block 1720, control passes via path 1728 to activity block 1730 wherein the presence of a missing solder defect is recorded. Control then passes via path 1732 to the end of the routine.

ALTERNATIVE SOLDER THICKNESS CALIBRATION TECHNIQUE

In some environments, the solder joint image intensity produced by a given thickness of solder is a function not only of the thickness of the solder comprising the joint, as described above in reference to FIGS. 23a, 23b, and 23c, but also the image intensity of the background region surrounding the solder joint. Specifically, for many applications, it has been found that the background intensity may contribute an additive component to the overall image intensity level of the solder joint image. Thus, for a fixed solder thickness, the measured intensity of the solder joint will increase as the background intensity level increases. If this is not recognized and corrected, the measured solder thicknesses will vary as a function of the background intensity, thus introducing an error in the solder thickness measurement. It has also been observed that the background intensity introduces a multiplicative component which causes the measured solder joint thickness to be lower than the real thickness as the background intensity level increases.

For many applications the additive component is dominant and the subtraction of a background correction factor from the measured solder joint image intensity is sufficient to provide an accurate determination of the thickness of the solder forming the solder joint image. This additive background correction factor will be referred to hereinafter as the P correction factor. In other applications the multiplicative component may be significant so that the multiplication of the solder joint image intensity by a second background correction factor is desirable to obtain a more accurate measurement of the thickness of the solder forming the solder joint image. This multiplicative background correction factor will be referred to hereinafter as the G correction factor.

In the embodiment described previously in accordance with FIGS. 23a-23c, the P correction factor is equal to the gray level of the image formed by the background region surrounding the solder joint. The P correction factor is applied by subtracting it (i.e., the gray level of the background) from the image intensity of the total image so that only the foreground image (i.e., the image due to the solder) remains. The background gray level of the image may be determined as described in the subroutine block 2550 discussed in detail in reference to FIG. 33 below.

Figure 41:
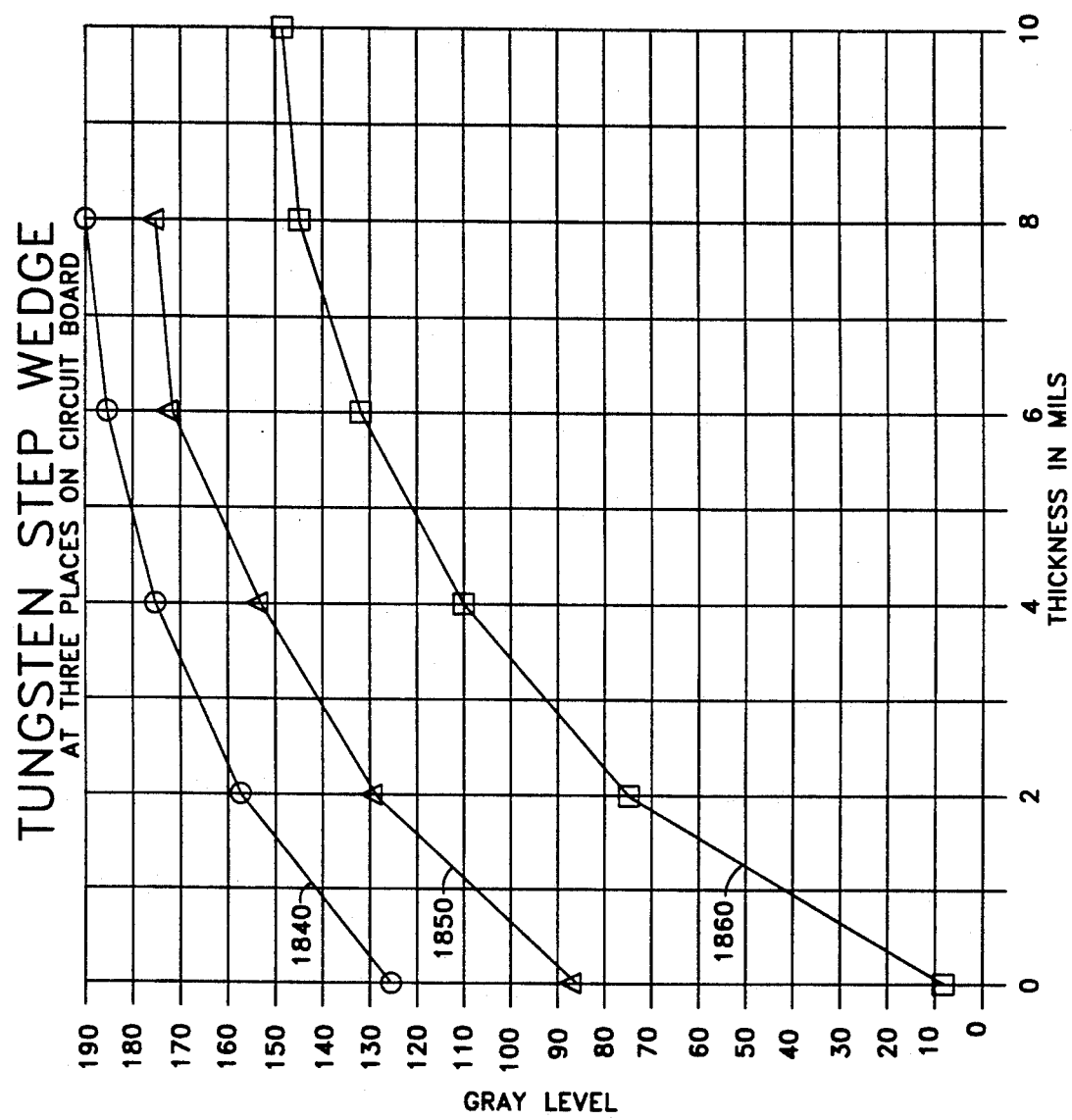
FIG. 41 is a graph which plots gray level versus solder thickness for a step wedge at three different background levels.
Figure 42:
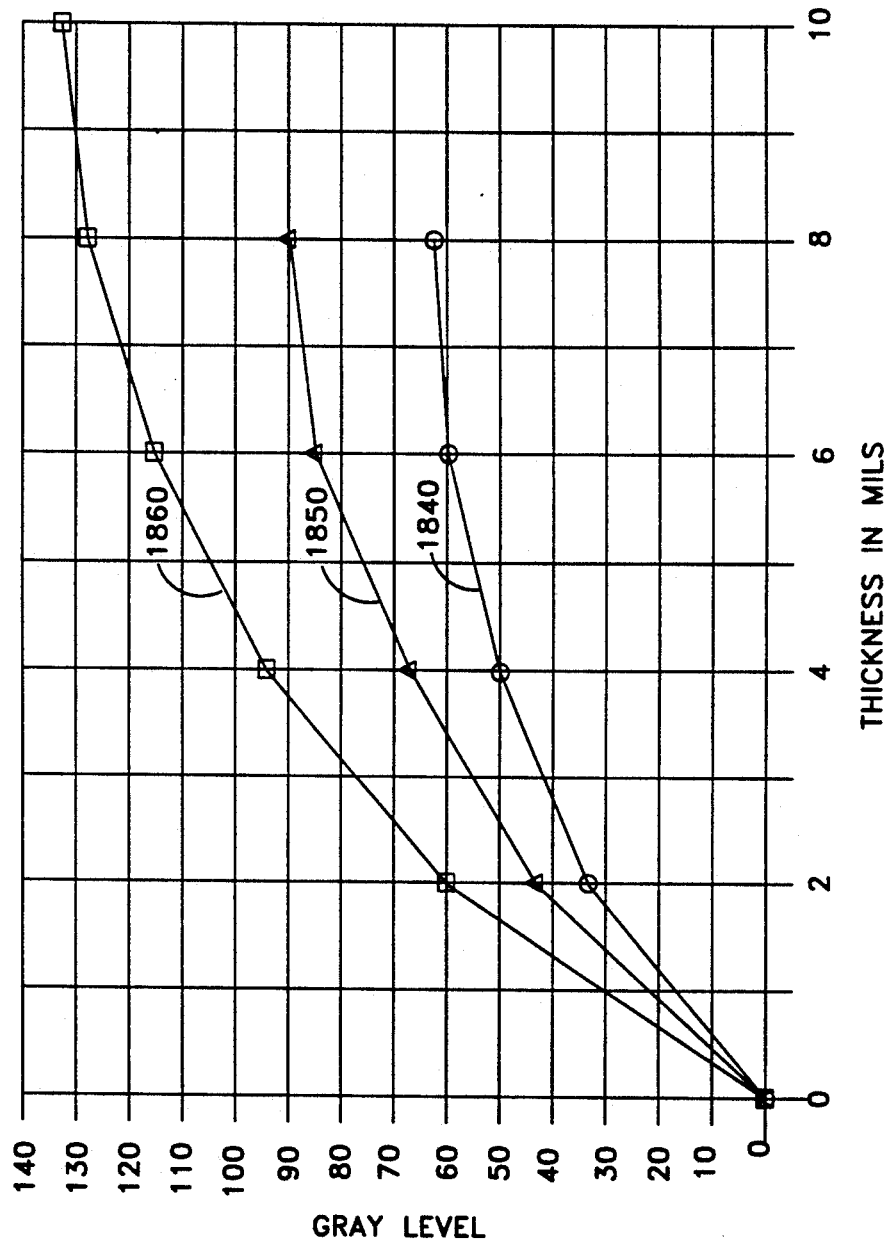
FIG. 42 is a graph which plots gray level versus solder thickness for the step wedge used in the graph of FIG. 41, after a first correction factor is applied.
Figure 43:
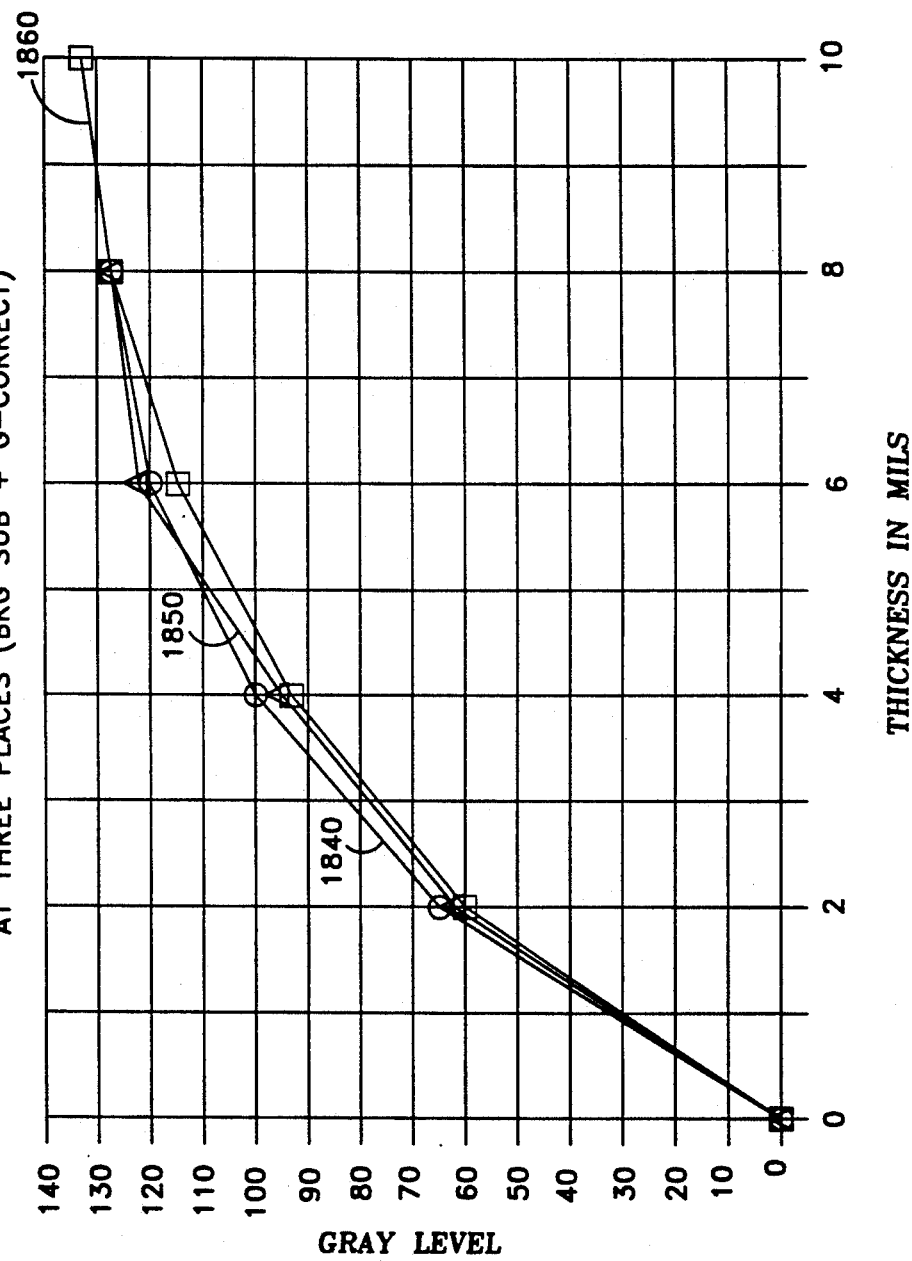
FIG. 43 is a graph which plots gray level versus solder thickness for the step wedge used in the graphs of FIGS. 41 and 42, after a second correction factor has been applied.

FIGS. 41-43 illustrate the effects that variations in background gray level have on solder thickness measurements (FIG. 41), as well as the effects on solder thickness measurements due to additive (FIG. 42) and multiplicative (FIG. 43) compensation.

FIG. 41 is a graph which depicts the measured gray levels versus the thicknesses of the step wedge 1560 at three locations on a circuit board having different background levels. Each curve represents the measured gray levels for the images of the step wedge 1560 at a different background gray level. A top curve 1840 represents the measured gray levels for the image of the step wedge 1560 having a background gray level of 126, a middle curve 1850 represents the measured gray levels for the image of the step wedge 1560 having a background gray level of 86, and a bottom curve 1860 represents the measured gray levels for the image of the step wedge 1560 having a background gray level of 15.

FIG. 42 is a graph which depicts the three curves of FIG. 41 after the additive component has been compensated for by subtracting the P correction factor from each of the three curves. It can be seen in FIG. 42 that even after the additive component of the background intensity has been compensated for, the gray levels corresponding to identical solder thicknesses are still quite varied for the image of the step wedge 1560 at different background levels. Thus, it is desirable in this case to introduce the G correction factor in order to reduce the variance in gray levels for identical solder thicknesses at different background levels.

FIG. 43 depicts the three curves of FIG. 42 after the multiplicative component of the background level has been compensated for by application of the G correction factor. Note that all the curves have been normalized to correspond to the curve 1860 having a background level of 15. Thus, it can be seen that the step wedge calibration technique which compensates for both the multiplicative component and the additive component due to the background level can be used to provide a more accurate measurement of the solder thickness for an inspected solder joint.

In order to compensate for both the additive and multiplicative components introduced by the background level, an alternative calibration technique than that previously described can be used. In this alternate calibration technique, a relationship is determined between the background level and the foreground level of solder joints on a circuit board. This relationship can then be used to determine the G correction factor for a solder joint which forms an image that has a specific background gray level value.

When determining the relationship between the background level and the foreground level of the images of solder joints on a circuit board, a test circuit board, which is similar to the circuit boards to be inspected, is inserted into the inspection device. Advantageously, the test board has a plurality of solder joints which are generally uniform in thickness, but are located in regions of the board which form images having varying background levels. A number of these solder joints (e.g., 200) are then sampled. At each of the sampled solder joints a laminographic cross-sectional image is produced, and a region of interest surrounding the image of the sampled solder joint is defined. The background level of the image formed by the background local to each of the sampled solder joints is then determined. The determined background gray level is subtracted from each pixel within the region of interest so that only the foreground image of the sampled solder joint remains. The average foreground gray level within the region of interest of each sampled solder joint image is then calculated. Thus, the image of each sampled solder joint will have a measured foreground gray level and a measured background gray level.

Figure 44:
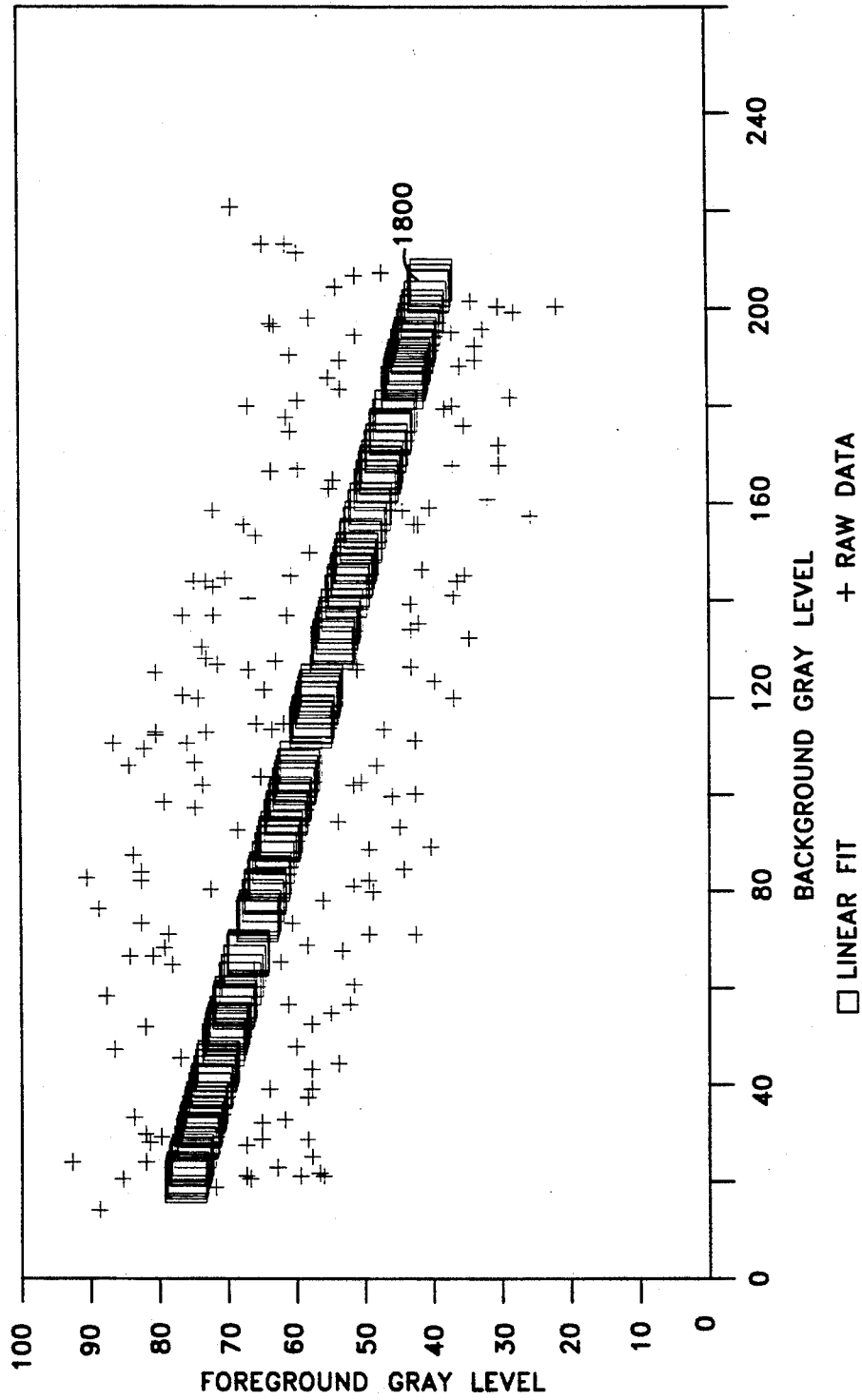
FIG. 44 is a graph which plots foreground gray level versus background gray level for solder joints of like thicknesses.

FIG. 44 is a graph which depicts the relationship between the gray level of the background and the gray level of the foreground for a plurality of sampled solder joints of generally uniform thickness. Each sampled solder joint is represented by a point on the graph of FIG. 44. The foreground gray level and the background gray level associated with each sampled solder joint is given by the coordinates of the point. Also depicted in FIG. 44 is a line 1800 which approximately fits the data points. The line 1800 indicates the overall relationship between the foreground gray level and the background gray level, and may, for example, be fit to the data points by the method of least squares. It should be noted that the characteristics of the line 1800 do not vary significantly for different thicknesses of the sampled solder joints, as long as all of the sampled solder joints are of substantially uniform thickness. For example, the general characteristics of the line 1800 would remain essentially the same if all the sampled solder joints were 5 mils thick or if all the sampled solder joints were 8 mils thick. This relationship between the foreground gray level and the background gray level can be used to determine the value of the G correction factor, which should be applied to a solder joint image having a given background image gray level.

In order to determine the G correction factor for a given background gray level, the graph of FIG. 44 is normalized with respect to a selected foreground gray level. For example, if the selected foreground gray level is 77, each of the values on the foreground gray level axis is divided by 77. The normalized foreground gray level axis then becomes the G correction factor axis which has a G correction factor corresponding to each background gray level. FIG. 45 depicts a graph which plots G correction factor versus background gray level for the data of FIG. 44 normalized to a foreground value of 77. The information correlating the G correction factor and the background gray level is advantageously implemented as a look-up file. The image analysis computer 272 stores the look-up file which contains the G correction factor corresponding to each background gray level. Note that the selection of the normalizing foreground gray level is preferably not arbitrary. Rather, the selected foreground gray level should correspond to a background gray level that is superimposed on the step wedge 1560 when calibrating the step wedge 1560. In this example, the background level corresponding to the foreground value of 77 is approximately 15. Thus a background of 15 will be superimposed on the step wedge 1560 during its calibration.

Figure 23D:
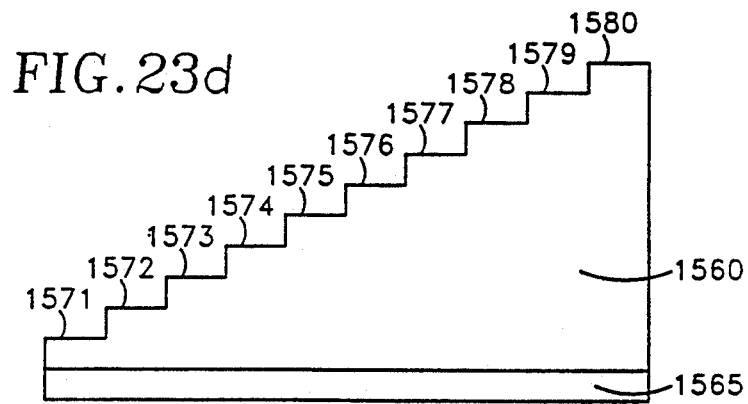
FIG. 23d shows the calibration step wedge of FIG. 23b with an additional platform secured to its base to provide a background level.

When calibrating the step wedge 1560, a laminographic cross-sectional image is taken of the step wedge 1560. The step wedge 1560 is advantageously placed on a platform 1565 as shown in FIG. 23d. The platform 1565 is constructed so that a low background gray level (i.e., 15 in this example, although values in the range of 10–20 may be acceptable for other cases) will be superimposed onto the image formed by the step wedge 1560.

Figure 23E:
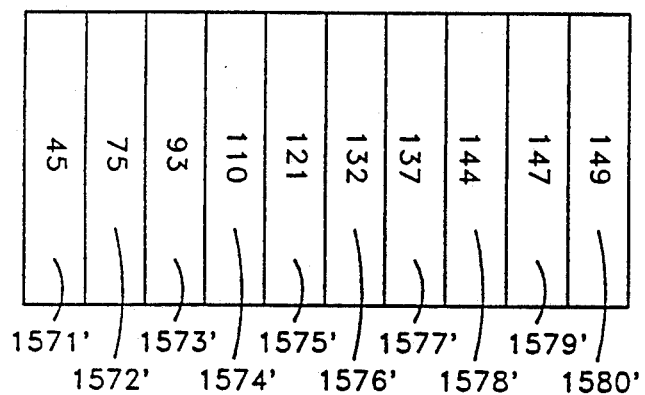
FIG. 23e is a schematic representation showing exemplary gray scale values corresponding to each step of the step wedge in FIG. 23d when a cross-sectional image of the step wedge is taken.
Figure 23F:
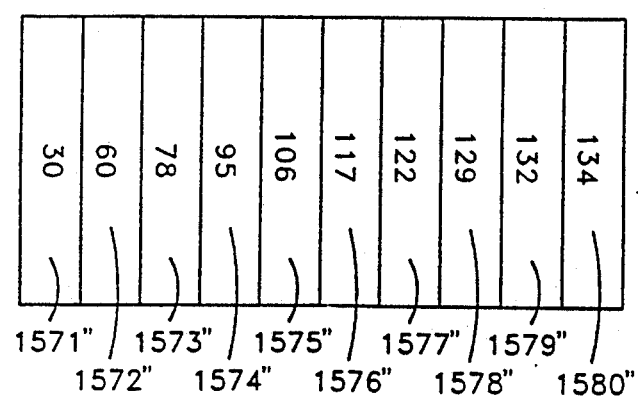
FIG. 23f shows the different gray scale values corresponding to each step in the step wedge of FIG. 23d when the gray scale due to the background platform is subtracted.

FIG. 23e is a cross-sectional image of the step wedge 1560 which shows representative gray level values corresponding to the image intensities 1571' through 1580' of the steps 1571 through 1580 when the platform 1565 is affixed to the step wedge 1560. The additive component of the background level is compensated for by subtracting the P correction factor (e.g., 15 in this example) from each measured gray level value within the cross-sectional image of the step wedge 1560, thereby leaving only the foreground image of the step wedge 1560. After the P correction factor has been subtracted, the average foreground gray level of each step of the step wedge 1560 is calculated. FIG. 23f is a cross-sectional image of the step wedge 1560 which shows sample foreground gray level values corresponding to the image intensities 1571" through 1580" of the steps 1571 through 1580 after subtraction of the P correction factor.

Thus, after the P correction factor has been subtracted from each measured gray level in the cross-sectional image of the step wedge 1560, only the foreground image of the step wedge 1560 remains. Note that, because the G correction factor is defined to be 1 for the background level that is superimposed onto the image formed by the step wedge 1560 (i.e., the background level due to the platform 1565), it is not necessary to apply the G correction factor to the measured foreground gray level values of the step wedge 1560.

For each solder thickness, the measured foreground gray level is output to a reference file which correlates the known solder thickness of each step of the step wedge 1560 with its corresponding measured foreground gray level. That is, the measured intensity minus the background. The reference file is advantageously stored within the image analysis computer 272. This provides a reference table from which to determine the solder thickness corresponding to a measured foreground gray level.

To obtain a calibrated gray level that can be used to determine the solder thickness of an inspected solder joint, the background gray level local to the inspected solder joint is determined. The determined background gray level is then subtracted from the gray levels of the pixels within the region of interest of the inspected solder joint image to obtain a foreground image of the solder joint. The G correction factor corresponding to the determined background gray level for the inspected solder joint is then found in the look-up file. Finally, the average foreground gray level of the inspected solder joint is divided by the G correction factor to obtain the calibrated foreground gray level.

The calibrated foreground gray level is used to reference a corresponding calibration solder thickness value. The solder thickness value corresponding to the calibrated foreground gray level can be found in the reference file that was made from the analysis of the step wedge 1560. For example, if the calibrated foreground gray level of an inspected solder joint is 95, the corresponding average solder thickness of the inspected joint will be approximately the thickness of the step 1574 of the step wedge 1560 (recall that the steps 1571–1580 of the step wedge 1560 are in a 1 mil incremental thicknesses from 1 mil to 10 mils in this example, so that the thickness of step 1574 is 4 mils).

ALTERNATIVE METHOD FOR DETECTION OF INSUFFICIENT/EXCESS SOLDER DEFECTS

An excess solder defect is defined as a quantity of solder which is in excess of a predefined nominal solder quantity plus an upper incremental solder quantity threshold. Excess solder may result in the presence of solder on portions of the circuit board, the component, or the conductive pad regions, where solder is unnecessary or even detrimental to performance of the connection. An insufficient solder defect is defined as a quantity of solder which is below the predefined nominal solder quantity minus a lower incremental solder quantity threshold. Insufficient solder may result in poor fillet quality and may not provide sufficient strength to the connection between conductive pads of a component and circuit board.

The range of solder quantity values between the nominal value minus the lower threshold, and the nominal value plus the upper threshold is the acceptable range of solder quantity which provides optimum quality in the connection between conducting pads. In many instances, the solder quantity may be correlated with the thickness of solder at a particular location. The particular values of the acceptable range of quantity, (i.e., thicknesses) may be determined by performing a statistical analysis on a number of test joints having varying solder thicknesses and selecting the thickness which has the lowest failure rate under expected operating conditions.

Figure 26:
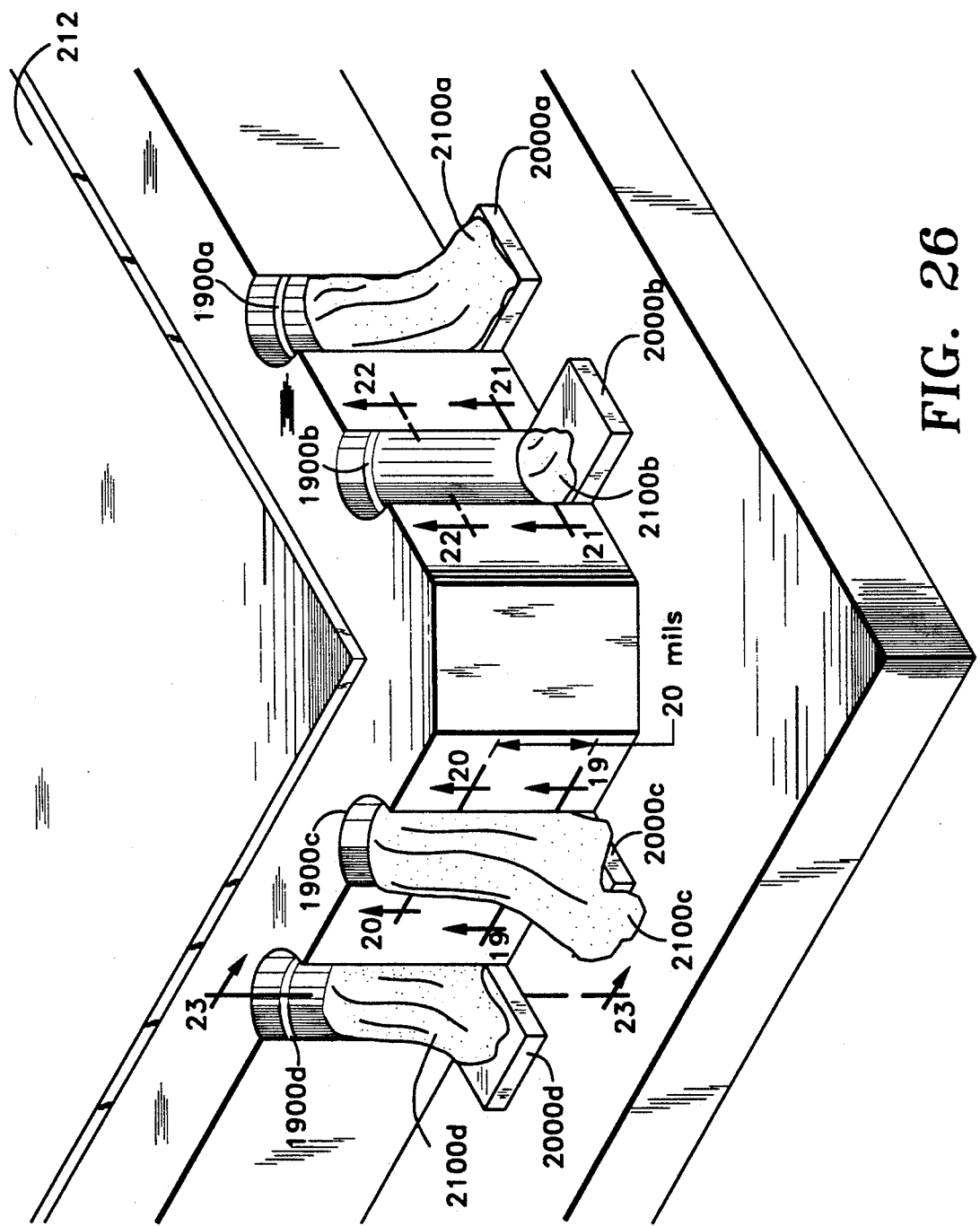
FIG. 26 is a perspective view of a Leadless Chip Carrier device having connections with varying thicknesses of solder.

The procedure for detecting an insufficient or excess solder defect generally comprises determining the average solder thickness within a predefined region of interest, calculating the ratio between the determined solder thickness and a predefined nominal solder thickness for that region, and comparing the calculated ratio to upper and lower threshold ratio values. This procedure for determining insufficient or excess solder defects will be described in detail with reference to FIGS. 25–39. FIG. 26 depicts an enlarged view of a portion of the LCC 212 illustrating the general visual appearance of solder connections formed between four metallized connector pad pairs 1900a/2000a through 1900d/2000d respectively. Connector pads 1900a through 1900d are on the LCC 212 while connector pads 2000a through 2000d are on the circuit board 210. Solder connection 2100d formed between the board/component connector pad pair 1900d/2000d is an example of a good connection having no visible defects. Solder connection 2100b, formed between the board/component conducting pads 1900b/2000b, is an example of a solder connection having an insufficient amount of solder to form a proper fillet and insure that the strength of the connection is sufficient. Solder connections 2100c and 2100a, formed between the board/component conducting pads 1900c/2000c and 1900a/2000a respectively, are examples of solder connections having an excess amount of solder. It can be seen from FIG. 26 that the solder connection 2100a does not spill out of the conductive pad region, however it is detected as an excess solder defect because the thickness of the connection 2100a exceeds the upper solder thickness ratio. Solder connection 2100c is an example of a gross excess solder defect where the solder is not contained wholly within the pad regions.

FIG. 27 depicts the appearance of an X-ray cross-sectional image of the portion of the LCC device 212 shown in FIG. 26. The plane shown by the cross-sectional image in FIG. 27 is parallel to the plane defined by the circuit board 210 and is approximately 0.0005 inch above the surface of the circuit board 210. The phantom lines indicating the location of the device 212 are shown for reference purposes only and may not be present in an actual cross-sectional image. Image regions 2100a', 2100b', 2100c', and 2100d' correspond to the solder connections 2100a, 2100b, 2100c, and 2100d, respectively, in the designated image plane.

FIG. 28 depicts an enlarged portion of FIG. 27 at the location of the excess solder defect image 2100c'. Note that the cross-sectional image 2100c' of the solder connection 2100c is taken at approximately the level of the board surface (i.e., 0.0005 inch above the surface of the circuit board 210 in one embodiment). The outline of the conducting pad 2000c and the edge of the LCC 212 are shown in phantom for reference only, and may not be present in an actual cross-sectional image of the solder connection 2100c. An arbitrary pixel grid comprising columns and rows is also shown to aid in the description of the automated procedure for detecting excess/insufficient solder defects.

Figure 30:
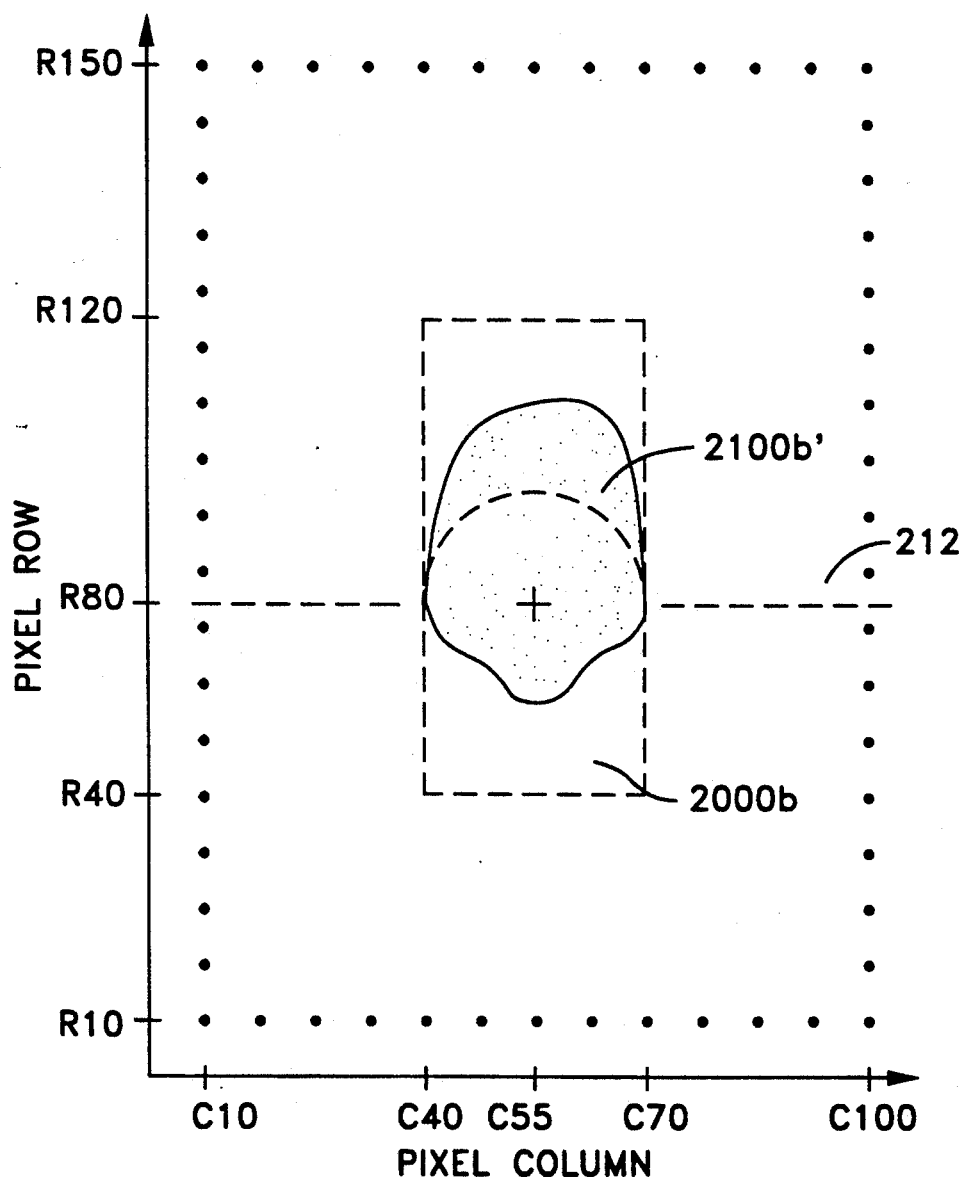
FIG. 30 is an enlarged cross-sectional view showing in greater detail the insufficient solder connection of FIG. 27.

FIG. 30 depicts an enlarged portion of FIG. 27 at the location of the insufficient solder defect image 2100b'. Note that the cross-sectional image 2100b' of the solder connection 2100b is also taken at approximately the level of the board surface (i.e., 0.0005 inch above the surface of the circuit board 210 in one embodiment). The outline of the conducting pad 2000b and the edge of the LCC 212 are shown in phantom for reference only, and may not be present in an actual cross-sectional image of the solder connection 2100b. An arbitrary pixel grid comprising columns and rows is also shown to aid in the description of the automated procedure for detecting excess/insufficient solder defects.

The procedure for detecting excess or insufficient solder defects described herein is used to test for both excess and insufficient solder defects for each defined region of interest. Thus, for purposes of the following description, the procedure will be illustrated only in reference to FIG. 28. It should be understood, however, that the procedure for detecting excess or insufficient solder defects can be applied equally in reference to the solder connection image 2100b' depicted in FIG. 30.

The initial step in the analysis of the image 2100c' in FIG. 28 comprises acquiring topographical data and inspection parameters necessary for performing an inspection and evaluation of an excess or insufficient solder defect. In one embodiment, the method for analyzing an image for the presence of an excess or insufficient solder defect uses as input, the centroid location and boundaries of the connection pad 2000c, a predetermined nominal solder thickness value, and two threshold values. In the example of FIG. 27, the CAD data file will contain the information that the connection pad 2000c has a centroid 2150 located at column and row pixel coordinates (C55,R80) as shown. Additionally, the CAD data file will contain the information that the pixel width of pad 2000c is 30 (the difference between pixel column numbers C40 and C70) and that the pad length is 80 pixels (the difference between pixel row numbers R120 and R40). Other inspection parameters necessary for performing the analysis will also be retrieved from the CAD data file.

Using the topographical data for pad 2000c, a joint-dependent region of interest (ROI) is defined. In this example, the defined region of interest is advantageously centered at the centroid 2150, and has boundaries determined by the pixel dimensions of the pad 2000c. It may be desirable in certain instances, however, to define other regions of interest which do not have boundaries determined by the pixel dimensions of the pad, such as the regions of interest 1601, 1602, and 1603 shown in FIG. 21. In the example shown in FIG. 27, the region of interest coincides with the pad boundaries and is 30 pixels wide (from C70 to C40) and 80 pixels long (from R120 to R40). The defined boundaries of the region of interest, are used to calculate the average thickness of the solder within the region of interest. Note that determining the average solder thickness within a predefined region of interest, with a corresponding predefined area, is substantially equivalent to determining the volume of solder within the region of interest, as the volume is equal to the area of the region of interest multiplied by the average solder thickness within the region of interest.

In order to accurately calculate the average solder thickness within the region of interest, it is desirable to know the image intensity of the background so that the variation in image intensity due to the background can be calibrated out of the system. In order to determine a background value, a background path 2200 is defined around the region of interest. In one embodiment, the background path 2200 is one pixel wide and is defined by path segments 2200a (from C10 to C100), 2200b (from R150 to R10), 2200c (from C100 to C10), and 2200d (from R10 to R150) as shown in the example in FIG. 28. Although the background path 2200 defined herein is one pixel wide and surrounds the region of interest, it is not essential that the background value be determined using a path of this model. For example, the path 2200 could be two or more pixels in width, and the path 2200 could be defined so that it is located to the right or the left of the region of interest.

When determining the background reference intensity value, the gray levels of all the pixels comprising the background path 2200 are averaged.

In some cases, the path 2200 may include portions which are not generally considered part of the background. For example, the path 2200 may include the image of a solder ball on the circuit board 210 which is intercepted by the background boundary path 2200, or perhaps the lead of an adjacent component. In such cases, it is desirable to filter out the effects due to unwanted features along the path 2200. Since the portions of the path 2200 which correspond to unwanted features typically have significantly higher gray levels than the true background gray level, the effects due to unwanted features can be filtered out by performing a second averaging of only those pixels which have a gray level which is lower than the first average gray level. The second average gray level is then selected to be the background reference gray level.

For example, in a situation when the unwanted features have higher gray levels than the true background, it is expected that the distribution of gray levels will include a few high gray levels (corresponding to the image of the unwanted feature), and a number of lower gray levels (corresponding to the background image). Therefore, it is expected that the higher gray levels will fall above the average value of all the pixels in the path 2200. When a second average is taken of only those values below the first average, none of the higher gray levels will be included. Thus, the gray levels corresponding to the unwanted image are filtered out of the second average calculation of the background intensity.

Once the background gray level is obtained, the image intensity due to the background within the region of interest is calibrated out of the system. One method of performing this calibration is to subtract the background reference gray level from the gray level assigned to each pixel within the region of interest. The calibrated gray levels of the pixels within the region of interest are then averaged to determine the calibrated average image intensity within the region of interest. An alternate method of performing the background calibration correction, described above with reference to FIGS. 23d-23f, is to subtract the background gray level (the P correction factor) from the gray level of each pixel within the region of interest. The resulting gray levels of the pixels are then averaged to provide an average gray level for the entire region of interest. The average gray level is then divided by the G correction factor to provide a final calibrated average image intensity. The calibrated average image intensity within the region of interest is then converted to an average solder thickness as determined by the image intensity versus solder thickness relationship stored within the reference file produced from the step wedge calibration discussed above.

When the solder thickness has been determined, the solder thickness value is divided by the predetermined nominal solder thickness in order to produce a solder thickness ratio. The solder thickness ratio is compared to an upper solder thickness ratio threshold and a lower solder thickness ratio threshold. If the solder thickness ratio is greater than the upper solder thickness ratio threshold, then an excess solder defect is reported. If the solder thickness ratio is less than the lower solder thickness ratio threshold, then an insufficient solder defect is reported. If the solder thickness ratio falls between the upper and lower solder thickness ratio thresholds, then a good joint is reported.

As an illustrative example, assume that the nominal solder thickness for the procedure described herein is 0.008 inch. Assume further that the upper solder thickness ratio threshold is 1.2, and the lower solder thickness ratio threshold is 0.8.

When analyzing the solder joint 2100b, and the solder joint 2100c, a surface cross-sectional slice is taken, and the average solder thickness for that slice is determined. The average solder thickness for the joint 2100c at the surface slice shown in FIG. 28 may be, for example, 0.012 inch, while the average solder thickness for the joint 2100b at the surface slice shown in FIG. 30 may be, for example, 0.004 inch. The solder thickness ratio for the joint 2100c is calculated as 0.012/0.008, or 1.50. This exceeds the upper solder thickness ratio threshold value of 1.2 so that an excess solder defect is reported. The solder thickness ratio for the joint 2100b is calculated as 0.004/0.008, or 0.50. This is less than the lower solder thickness ratio threshold value of 0.8 so that an insufficient solder defect is reported.

In addition to the report indicating if a joint is excess, insufficient, or good, a second report is output by the inspection system which indicates the solder thickness ratio for each inspected joint. As each joint is inspected, any trends in joint thickness can be observed to determine if the solder application process should be altered to avoid the production of defective solder joints. Thus, it is possible to make a quantitative evaluation of the solder application process. For example, during inspection of a number of circuit boards, an upward trend in solder thickness ratio might be detected for the inspected solder joints on successive circuit boards. In response, the solder joint inspection system would transmit a signal to the solder application device (e.g., a wave flow machine, or a paste printer). The signal transmitted to the solder application device would alter the solder application process to reduce the quantity of solder deposited on the contact pads of subsequent circuit boards. In this manner, the report generated by the solder joint inspection device acts as a process control feedback system which monitors the solder application process and provides feedback to insure that defective joints are not produced and that the process is continually adjusted to ensure optimum performance. This process control feedback system may be fully automated, semiautomated or manual.

In one embodiment, the process control feedback system is fully automated so that immediate and direct control of the solder application process is maintained by the solder joint inspection device. Ideally, all solder joints produced would have a solder thickness equal to the predefined nominal solder thickness. Therefore, the process control feedback system is advantageously implemented to detect and compensate for any variations away from the nominal solder thickness value.

The process control feedback system may be implemented as a microprocessor system having an interface for both the solder joint inspection device, and the solder application device. Data relating to the solder thicknesses of inspected solder joints are advantageously transmitted to the microprocessor. The transmitted data may include the solder thickness, and the location of an inspected joint. The microprocessor in turn evaluates the transmitted data to determine what adjustments need to be made in the solder application process. The microprocessor is advantageously pre-programmed, according to the conditions and specifications of manufacture for a given solder application device, so that the appropriate feedback signals are transmitted from the microprocessor to the solder application device.

The process control feedback system may also be implemented using a programmable read only memory (PROM). In this embodiment, the PROM is advantageously pre-programmed so that feedback signals appropriate to control and maintain the quality of the electrical interconnections formed by the solder application device are generated in response to data from the defect and SPC files.

Figure 32A:
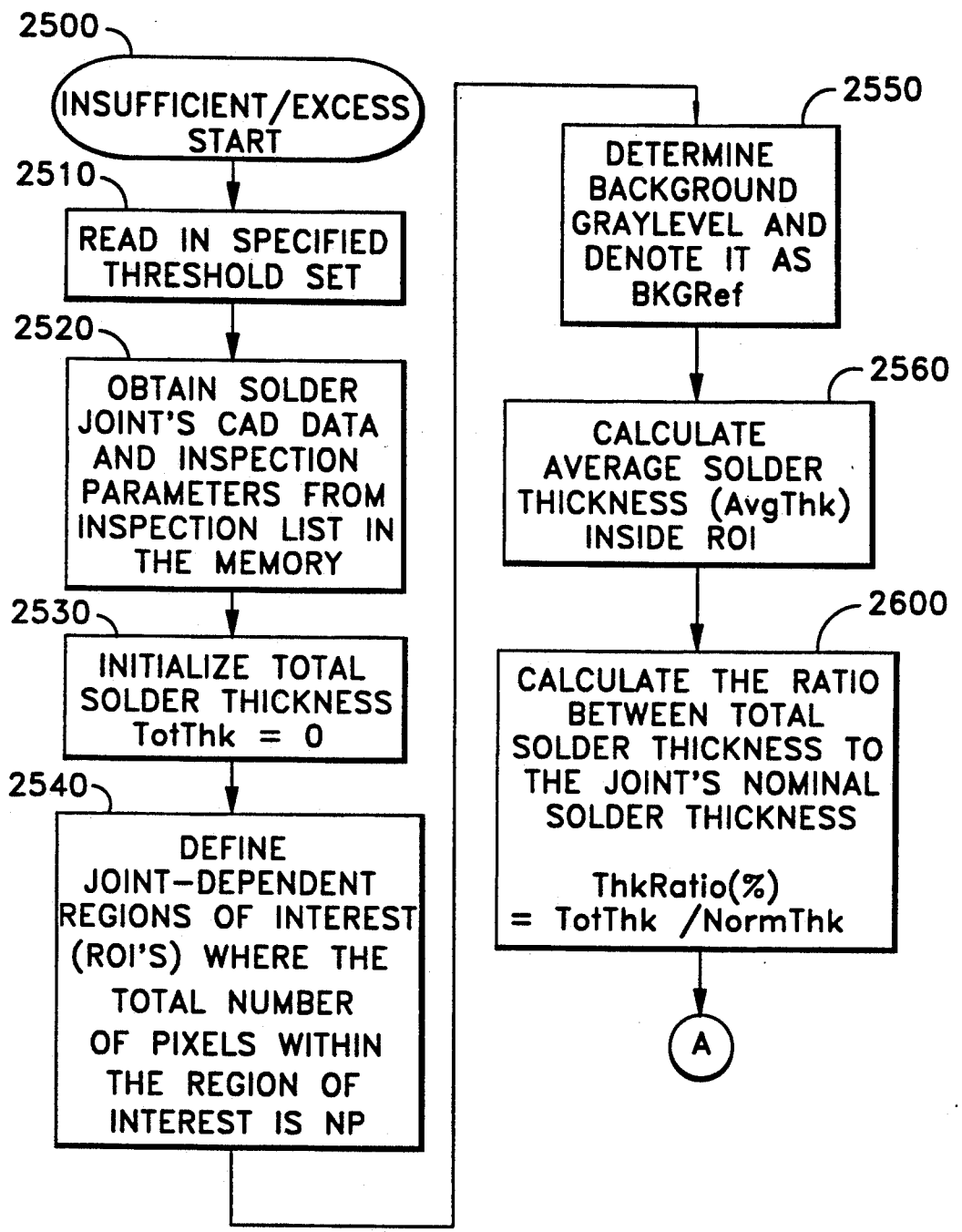
FIGS. 32a and 32b are a flowchart illustrating the process for automatically locating and identifying an excess or insufficient solder defect.
Figure 32B:
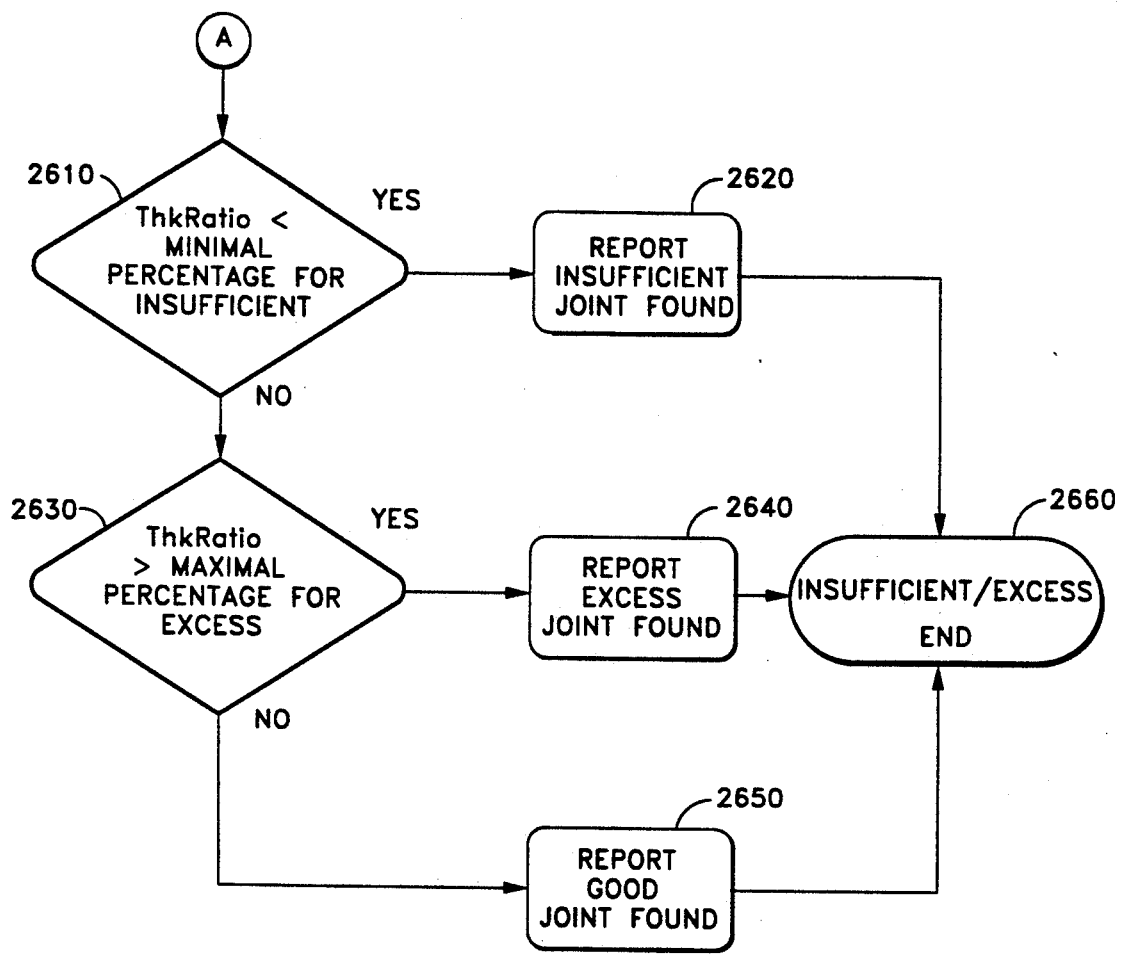

FIGS. 32a and 32b depict a flowchart which details the method of detecting insufficient/excess solder defects according to the present invention. The method begins in a start block 2500 and proceeds to read in the specified threshold data set in a process block 2510. The threshold data set includes a particular joint's nominal solder thickness, NormThk, as well as upper and lower solder thickness percentage threshold values. The method then proceeds to a process block 2520 wherein the CAD data and inspection parameters for the joint to be inspected are obtained from the data file. This data includes the centroid location and the pad dimensions (i.e., the pixel width of the pad, PW, and the pixel length of the pad, PL) of the joint to be inspected. The method then continues to a process block 2530 wherein the variable TotThk, which represents the total solder thickness is set to zero.

After the total solder thickness value, TotThk, is set to zero, the method enters a process block 2540 wherein one or more regions of interest are defined local to the joint to be inspected. The gray level of each pixel within a given region of interest is denoted as P(i,j), where i indicates the pixel row coordinate, and j indicates the pixel column coordinate. The total number of pixels within the region of interest is designated as NP.

The method then enters a subroutine block 2550. A subroutine block indicates that a sub-method is used to process information. Although a brief description of the subroutine block 2550 will be presented here, a detailed description of the function of the subroutine block 2550 is presented below in reference to FIG. 33. In the subroutine block 2550, the reference gray level of the background is determined. As previously explained, in a laminographic image, a sharp image is produced by the object in the focal plane, while a blurred image is produced by other objects which are not in the focal plane. The gray levels produced by the object in the focal plane of the X-ray beam are generally high, while the gray levels produced by the other objects not in the focal plane tend to be lower. If a solder joint is in the focal plane, some of the image intensity is produced by the thickness of the solder joint, while the rest of the image intensity is a result of the background image. The total image intensity is then determined as the sum of the background image intensity and the focal plane, or foreground, image intensity. In addition to this additive effect, the foreground image intensity produced by a given thickness of solder also varies linearly as a function of the background image intensity, so that a multiplicative effect is introduced. Thus, in order to determine the image intensity due exclusively to the thickness of the solder joint, it is advantageous to know the background gray level, BKGRef.

After the background reference value, BKGRef, is determined in the subroutine block 2550, the average thickness inside the region of interest is calculated in a subroutine block 2560. In the subroutine block 2560, the background reference value is subtracted from the gray level, P(i,j), of each pixel. The resulting values (i.e., P(i,j)−BKGRef) are then summed and stored as a value PixelSUM. PixelSUM is subsequently divided by NP, the total number of pixels within the region of interest, to obtain the average gray level, PixelAverage. Finally, the value PixelAverage is divided by the G correction factor to obtain a calibrated gray level value of PixelAverage/G. The average solder thickness is then determined in the subroutine block 2560 based upon the reference file which correlates solder thickness and image intensity as determined in the step wedge calibration procedure discussed above. In one embodiment, the reference file stores a thickness value corresponding to each calibrated gray level. The subroutine block 2560 is discussed in detail below in reference to FIG. 34.

After the solder thickness has been determined in the subroutine block 2560, the method enters into a process block 2600 wherein the solder thickness of the inspected joint is divided by the predetermined nominal solder thickness value (e.g., 0.008 inch as in the previous example). The resulting value is multiplied by 100 to obtain the solder thickness percentage ratio.

Following the calculation of the solder thickness percentage ratio, the method continues into a decision block 2610 wherein a comparison is performed to determine if the solder thickness percentage ratio is less than the lower solder thickness percentage threshold. If the solder thickness percentage ratio, ThkRatio, is less than the lower solder thickness percentage threshold, then an insufficient solder defect is reported in a process block 2620. If ThkRatio is not less than the lower solder thickness percentage ratio, the method enters a decision block 2630.

In the decision block 2630, a comparison is performed to determine if the solder thickness percentage ratio is greater than the upper solder thickness percentage threshold. If the solder thickness percentage ratio is greater than the upper solder thickness percentage threshold, then an excess solder defect is reported in a process block 2640. If ThkRatio is not greater than the upper solder thickness percentage ratio, then a good joint is reported in a process block 2650. Once a joint quality report has been made, the method ends in a process block 2660.

Figure 33:
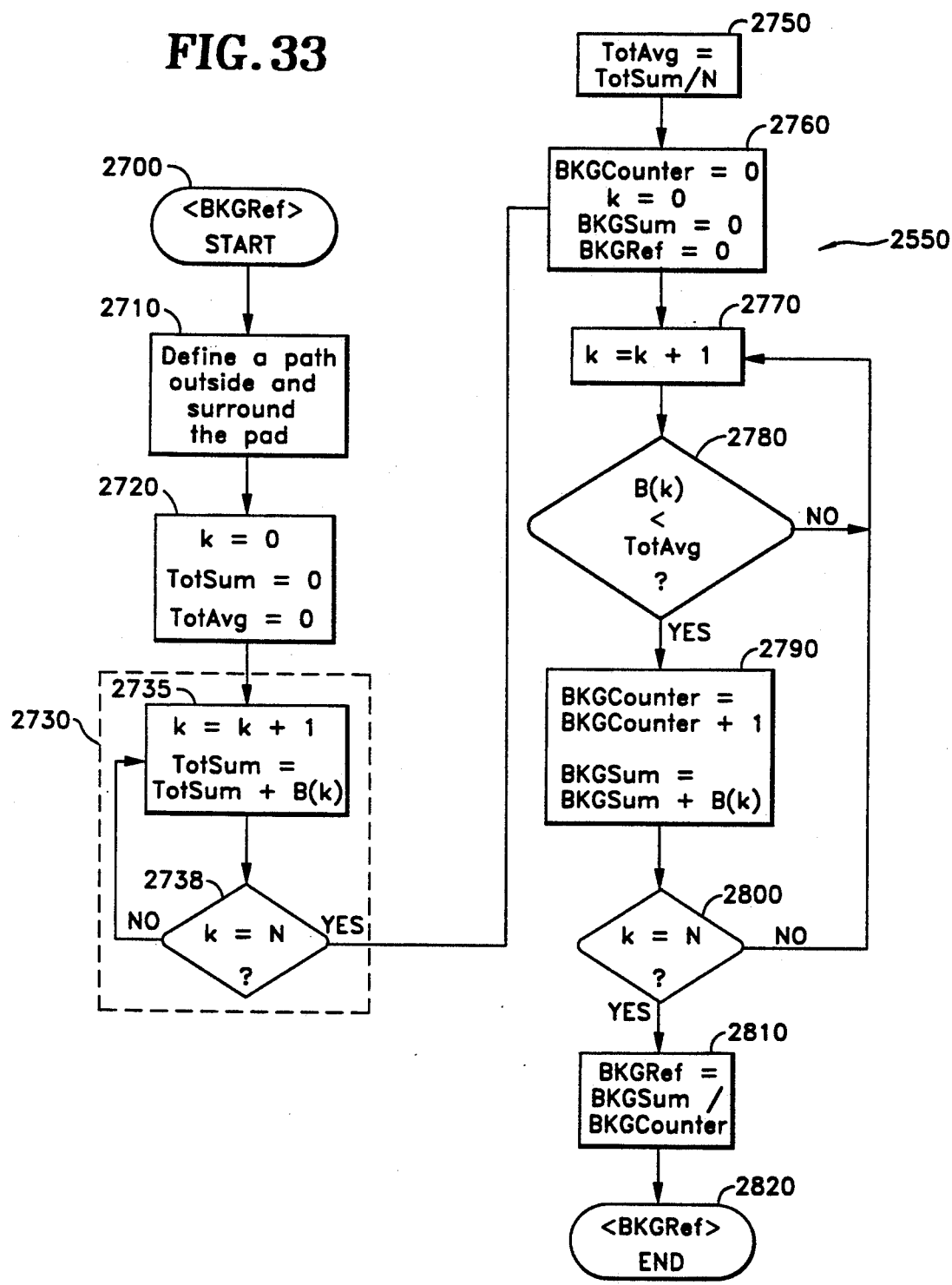
FIG. 33 is a flowchart illustrating the process for determining the background gray scale value local to an inspected solder joint.

FIG. 33 depicts a flowchart which details the background reference subroutine block 2550. The background reference subroutine block 2550 begins in start block 2700. The method then enters into a process block 2710. In the process block 2710, a path having N pixels is defined around the region of interest. Each pixel in the path has a gray level denoted as B(k), where k varies from 1 to N.

After a path is defined in the process block 2710, the method proceeds to a process block 2720 wherein certain variables, including k as well as the total gray level, TotSum, and the average gray level, TotAvg, are initialized to zero. The method then enters a loop 2730 which totals the gray levels of all the pixels along the path. In a process block 2735, the value of k is incremented, and adds the corresponding gray level, B(k), to the variable TotSum. The method then continues to a decision block 2738 wherein a test is performed to determine if the variable k is equal to N. If the variable k is not equal to N, this indicates that not all the gray levels of the pixels in the path have been accumulated into the sum TotSum. The method therefore returns to the process block 2735 wherein the variable k is incremented and the corresponding gray level, B(k), is added to the variable TotSum. The method continues in the loop 2730 until k equals N indicating that all the pixels in the path have been summed.

After all the gray levels have been tallied, the method enters a process block 2750 wherein the average gray level, TotAvg, is obtained by dividing the sum of all the gray levels along the path, TotSum, by the total number of pixels in the path, N.

As mentioned above, it is possible that some regions along the path are not considered part of the background image (e.g., solder balls, solder bridges, etc.). Therefore, the value of TotAvg may not accurately represent the background reference gray level. The effects due to non-background images within the path can be offset by performing a second averaging on all the gray levels which fall below the value of TotAvg. This is because the images along the path which are not part of the background tend to have higher gray levels than the background gray level. Thus, those gray levels which are due to non-background images will typically fall above the average gray level for all the pixels within the path. If a second averaging is then performed on all the gray levels which fall below the original average value, the non-background gray levels will be excluded from the second averaging, thereby providing a more representative value for the background reference image intensity.

In order to initiate the second averaging sequence, the method proceeds to a process block 2760 wherein a second set of variables is initialized to zero. The second set of variables includes a tabulator variable, BKGCounter, which accounts for the total number of pixels along the path having a gray level less than the average gray level of all the pixels on the path. The second set of variables also includes a summation variable, BKGSum, which sums the gray levels of all the pixels having a gray level less than the average gray level. The variable indicating the final calculated background gray level, BKGRef, as well as the variable k are also initiated to zero in the process block 2760.

After all the variables have been initialized, the method continues to a process block 2770 wherein the variable k is incremented. The method then enters a decision block 2780 wherein a test is performed to determine if B(k), the gray level of the kth pixel along the path, is less than the previously calculated average gray level TotAvg. If B(k) is not less than TotAvg, then the method returns to the process block 2770 and k is once again incremented. This effectively withdraws from the averaging process any pixels having a gray level greater than the value of TotAvg.

When the gray level of a pixel is determined to be less than the value of TotAvg in the decision block 2780, then the method proceeds to a process block 2790 wherein the value of BKGCounter is incremented by one, and the value of B(k) is added to the value of BKGSum. The method then enters a decision block 2800 wherein a test is performed to determine if k is equal to N, that is, to determine if all the pixels in the path have been summed. If k is not equal to N, this implies that not all of the pixels in the path have been accounted for and the process returns to the process block 2770 wherein k is again incremented by one. This cycle continues until all the pixels in the defined path have been summed.

Once all the pixels in the path have been processed, the method enters a process block 2810, wherein the background reference gray level, BKGRef, is calculated. BKGRef is calculated by dividing the sum of the gray levels falling below the value of TotAvg, by the total number of pixels having an image intensity which is less than TotAvg. This is accomplished by dividing BKGSum by BKGCounter. After the background reference gray level is calculated in the process block 2810, the method proceeds to an end block 2820 and the method exits the subroutine block 2550.

Figure 34:
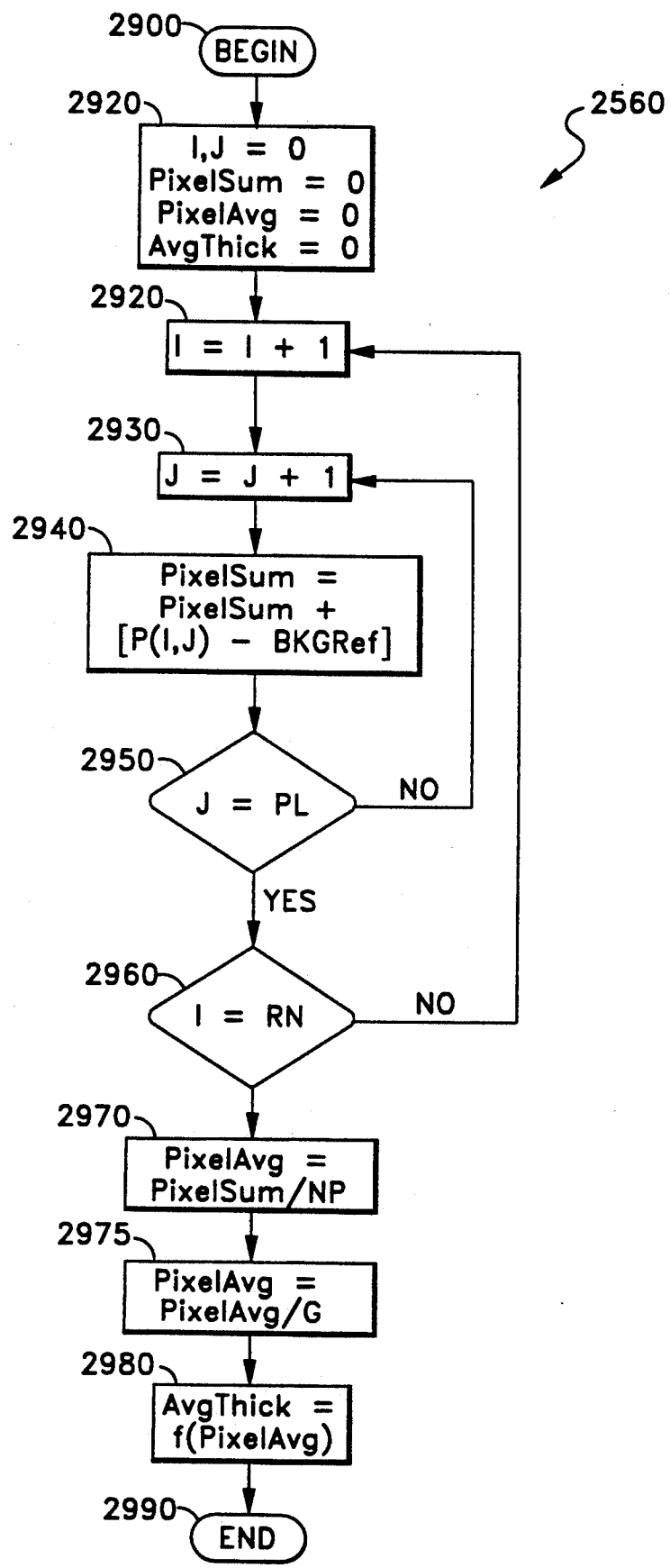
FIG. 34 is a flowchart illustrating the process for calculating the average solder thickness of an inspected solder joint.

FIG. 34 details the method of the subroutine block 2560 shown in FIG. 32a wherein the average solder thickness within the region of interest is calculated. After entering the subroutine block 2560, the method begins in a start block 2900. The method then proceeds to a process block 2910 wherein the subroutine variables are initialized to zero. The subroutine variables include counting variables i and j, a variable PixelSUM, which cumulates the calibrated gray levels of all the pixels within the region of interest, and a variable PixelAverage, which is assigned the calibrated average gray level of all the pixels within the region of interest. The average solder thickness subroutine variables also include a variable AvgThick which is assigned the average solder thickness which corresponds to the calibrated average gray level PixelAverage. The variable AvgThick is also initialized to zero.

The method then proceeds into a dual counting loop which allows all the pixel gray levels along a row, and then along each column, to be summed until the gray levels of all the pixels within the region of interest are tabulated. The method first enters into a process block 2920, wherein the column counting variable, i, is incremented. The method then continues into a process block 2930 wherein the row counter variable, j, is incremented.

After the row counter variable j has been incremented, the method then enters a process block 2940 wherein the value of the variable PixelSum is augmented by the calibrated gray level corresponding to the pixel at the coordinates (i,j). The gray level corresponding to the pixel at the coordinates (i,j) is denoted as P(i,j). In order to compensate for the additive effect due to the background, and thereby obtain the image intensity due only to the foreground, the background reference gray level, BKGRef, is subtracted from the gray level P(i,j). Thus, the value of PixelSUM is augmented by a value P(i,j)-BKGRef in the process block 2940.

After the value of PixelSUM is thus augmented, the method continues to a decision block 2950, wherein a test is performed to determine if j is equal to the pixel length of the region of interest, PL. If j is equal to the pixel length of the region of interest, PL, this indicates that a column of pixels has been completed, and the method continues into a decision block 2960. Otherwise, the method returns to the process block 2930 wherein the variable j is again incremented by one. This first cycle continues until a column has been completed. When a column has been completed, the method enters into the process block 2960 wherein a test is performed to determine if the variable i is equal to the pixel width of the region of interest, PW. If the variable i is equal to PW, this indicates that all the pixels in the region of interest have been accounted for, and the method enters into a process block 2970. Otherwise, the method returns to the process block 2920 wherein the variable i is again incremented by one. This cycle continues until all the pixels within the region of interest have been tabulated.

Once all the pixels within the region of interest have been tabulated, the method enters into the process block 2970 wherein the variable PixelAverage is assigned the value of PixelSUM/NP (where NP is the total number of pixels within the region of interest). The value of PixelSUM/NP is the average gray level due only to the foreground within the region of interest.

Following the calculation of PixelAverage, the method enters a process block 2975 wherein PixelAverage is divided by the G correction factor. The G correction factor which corresponds to the value of BkgRef is obtained from the look-up file stored within the image analysis computer 272. The resulting value (i.e., PixelAverage/G), is the calibrated average gray level.

Once the calibrated average gray level is calculated, the method enters a process block 2980 wherein the average solder thickness within the region of interest is determined. As discussed above in relation to FIG. 23c, the relationship between image intensity and solder thickness is determined in a conventional calibration procedure using the step wedge 1560 of varying solder thicknesses, and stored within a reference file within the image analysis computer 272. Thus, for each gray level, a corresponding solder thickness value is stored within the memory of the analysis computer 272. In the process block 2980, the solder thickness corresponding to the calibrated average gray level is output from the subroutine block 2560. The method finally proceeds into the end block 2990 and exits the average solder thickness subroutine 2560.

Heretofore the method of detecting excess/insufficient solder defects has been described for the case where it is sufficient to take a cross-sectional image slice at only one level, specifically, a level which is near the surface of the circuit board. However, in certain cases it may be desirable to take a cross-sectional image slice at more than one level. For example, it is advantageous to take more than one cross-sectional slice in some applications where the inspected solder joint is quite thick, as in the case of an LCC type device. This is because certain difficulties arise when inspecting solder joints having a thickness in excess of 0.020 inch.

Figure 23G:
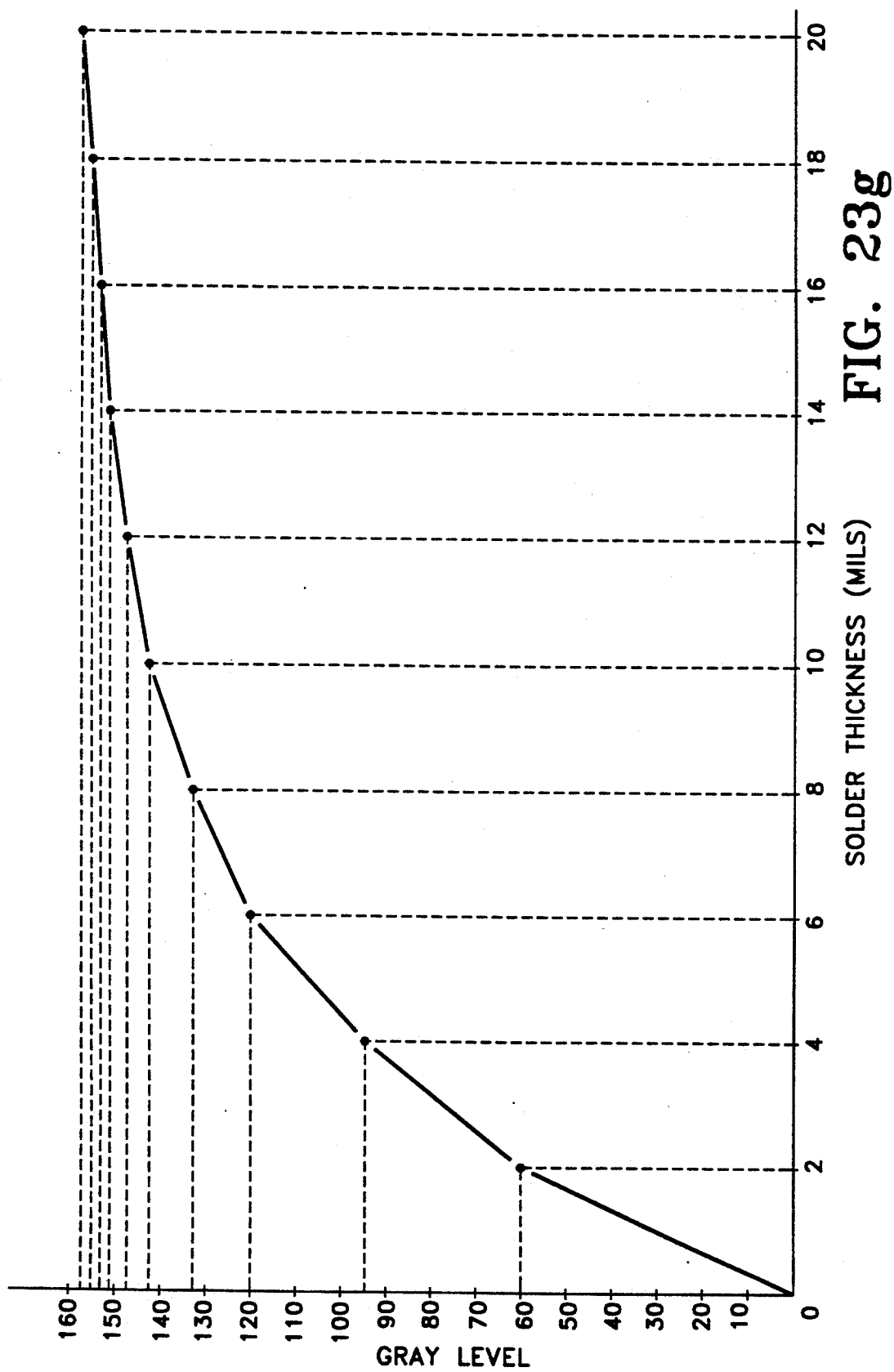
FIG. 23g is an exemplary graph that plots one relationship between solder thickness and gray scale up to and including 20 mils of solder.

Due to blurring and decreased sensitivity as a function of thickness, solder thicknesses above a certain threshold are more difficult to measure accurately. As can be seen from the graph of image intensity versus solder thickness shown in FIG. 23g, the image intensity becomes asymptotic for solder thicknesses in excess of 0.020 inches. That is, at low solder thicknesses, an increase in solder thickness results in a corresponding increase in image intensity, however, at higher solder thicknesses (e.g., 0.020 inch) an increase in solder thickness results in a much smaller corresponding increase in image intensity. Thus, as the inspected solder joint becomes thicker, it becomes more difficult to differentiate between image intensities, so that it is difficult to determine an exact solder thickness for a given gray level. In many applications it has been found that solder which is in excess of 0.020 inch from the focal plane of the X-ray beam is incorporated within the background image. This is due in part, to the severe blurring associated with the laminography process of objects outside of the focal plane.

Thus, for solder joints in excess of a certain thickness, the analysis method can be modified to obtain cross-sectional images at multiple levels within the solder joint. The number of levels to be analyzed for a given joint is advantageously stored within the threshold data set (discussed above in relation to the process block 2510 in FIG. 32a). Each level is preferably separated by a distance equal to the maximum discernable solder thickness (e.g., 0.020 inches in one embodiment). In order to determine the total thickness for a solder connection using multiple slices, the determined thickness at each slice is added to the thickness of the next slice until all slices for a given solder connection have been analyzed.

As an illustrative example, consider a solder cylinder having a thickness of 30 mils adjacent to, and on a common surface with, a slab of solder having a thickness of 10 mils. When a cross-sectional slice is taken at the surface level, a solder thickness of 20 mils will be measured for the cylinder, while a solder thickness of 10 mils will be measured for the slab. Note that, even though the actual thickness of the cylinder is 30 mils, a solder thickness of 20 mils will be measured for the cylinder at the surface level because the maximum discernible solder thickness in this embodiment is 20 mils. When a second cross-sectional slice is taken at a level 20 mils above the surface, then a solder thickness of 10 mils will be measured for the cylinder, while no solder will be measured for the slab. Thus, the total measured solder thickness for both the cylinder and the slab will be the addition of the two measurements (i.e., 30 mils for the cylinder and 10 mils for the slab).

In the case of the solder connection 2100c, it is desirable to obtain more than one slice to accurately determine the total solder thickness of the joint 2100c. After the average solder thickness is calculated at the surface level within the region of interest shown in FIG. 27, a second cross-sectional slice is taken at a level which is advantageously 0.020 inch above the level of the first cross-sectional slice. The procedure for determining the solder thickness at the second cross-sectional image level is the same as the procedure used to determine the solder thickness at the first cross-sectional image level.

Figure 29:
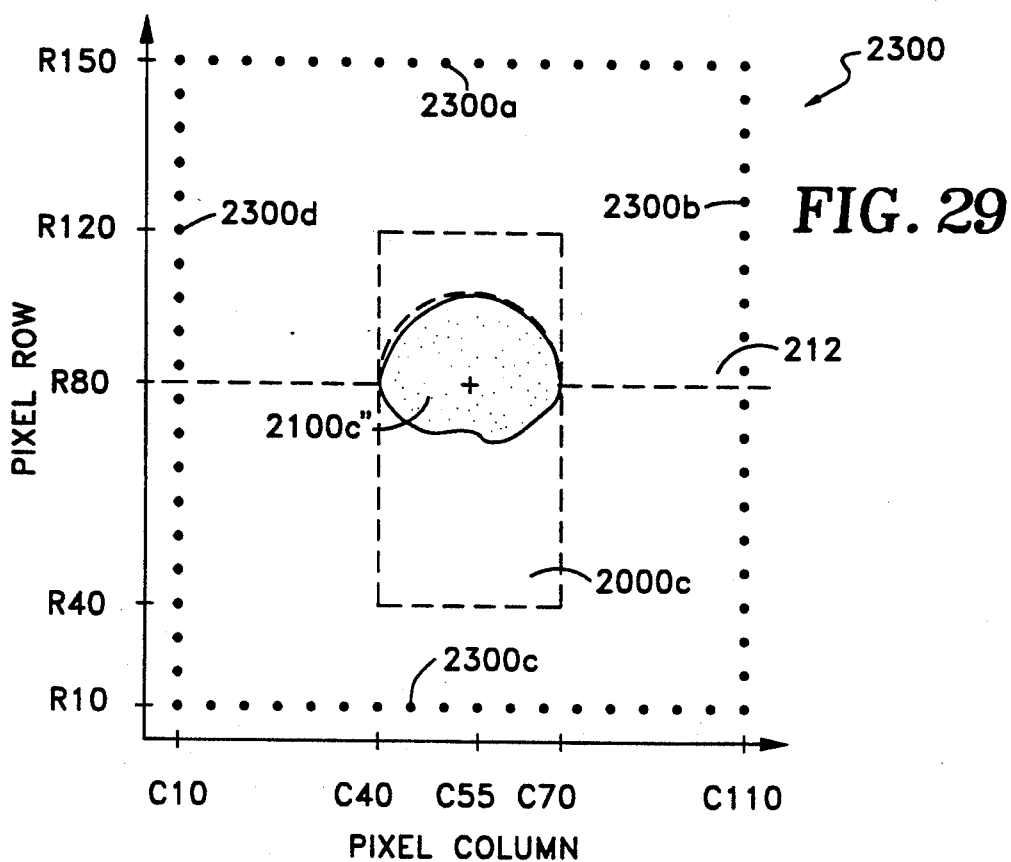
FIG. 29 is a cross-sectional view which shows how the excess solder connection might appear if the cross-sectional slice were taken at a level of approximately 20 mils above the board surface.

FIG. 29 depicts a cross-sectional image 2100c″ which corresponds to the solder connection 2100c at a height approximately 0.0205 inch above the board surface. The outline of the pad 2000c, and the edge of the LCC 212 are shown for reference only and may not appear in the actual cross-sectional image. The average image intensity is then calculated within the region of interest (the region of interest is defined again in this case to correspond to the boundaries of the pad 2000c). The procedure of calculating the average image intensity within the region of interest shown in FIG. 29 includes the steps of: 1) determining the background reference gray level using a path 2300 shown in FIG. 28; 2) calibrating out the effects due to the background image intensity by subtracting the background reference gray level from the gray level of each pixel in the region of interest; and 3) averaging the calibrated gray levels within the region of interest and dividing the obtained value by the G correction factor to obtain the calibrated average gray level within the region of interest. The solder thickness at the second cross-sectional slice can then be determined using the relationship between image intensity and solder thickness shown in FIG. 23f.

The total thickness of the solder connection 2100c is then obtained by adding the solder thickness value obtained from the first cross-sectional slice taken 0.0005 inch above the board surface, and the solder thickness value obtained from the second cross-sectional slice taken 0.0205 inch above the board surface.

When the total solder thickness has been determined by summing the solder thicknesses at each cross-sectional level, the total solder thickness is divided by the predetermined nominal solder thickness in order to produce a solder thickness ratio. The solder thickness ratio is compared to an upper and lower solder percentage threshold. If the solder thickness ratio is greater than the upper solder percentage threshold, then an excess solder defect is reported. If the solder thickness ratio is less than the lower solder percentage threshold, then an insufficient solder defect is reported. If the solder thickness ratio falls between the upper and lower solder percentage thresholds, then a good joint is reported.

As an illustrative example, assume that the nominal solder thickness for the procedure described herein is 0.016 inch. Assume further that the upper solder percentage threshold is 1.2, and the lower solder percentage threshold is 0.8.

When analyzing the solder joint 2100b, and the solder joint 2100c, the first step in the procedure is to take a surface cross-sectional slice and determine an average solder thickness from that image slice. The average solder thickness for the joint 2100c determined from the surface slice shown in FIG. 28 may be, for example, 0.014 inch, while the average solder thickness for the joint 2100b at the surface slice shown in FIG. 30 may be, for example, 0.004 inch.

Figure 31:
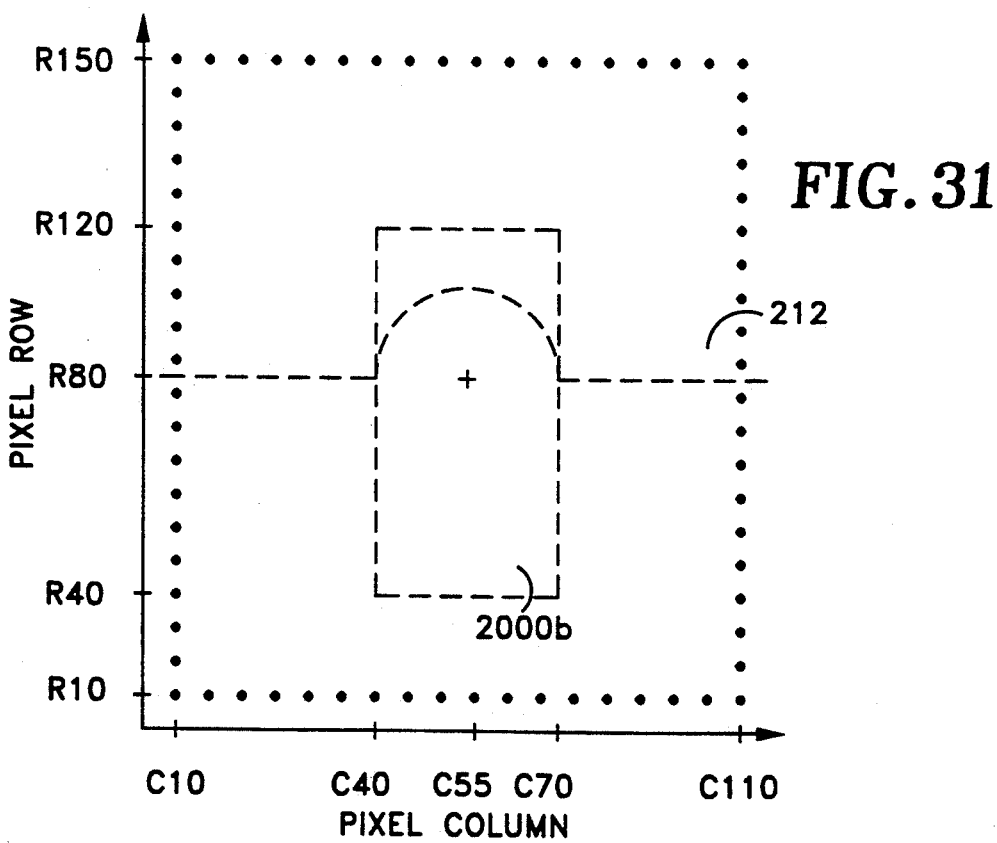
FIG. 31 is a cross-sectional view which shows how the insufficient solder connection might appear if the cross-sectional slice were taken at a level of approximately 20 mils above the board surface.

The next step in the procedure is to take a second cross-sectional slice for each solder joint and determine the average solder thickness for that slice position. The average solder thickness of the joint 2100c at the second slice shown in FIG. 29 may be, for example, 0.006 inch. FIG. 31 depicts a cross-sectional image of the solder joint 2100b at a level 0.0205 inch above the surface of the circuit board 210. The average solder thickness of the joint 2100b at the second slice shown in FIG. 31 may be, for example, 0 inches indicating no solder present. Thus, the total average solder thickness for the joint 2100c is 0.020 inch (0.014+0.006), while the total average solder thickness for the joint 2100b is 0.004 inch.

The solder thickness ratio for the joint 2100c is calculated as 0.020/0.016, or 1.25. This exceeds the upper solder percentage threshold value of 1.2 so that an excess solder defect is reported. The solder thickness ratio for the joint 2100b is calculated as 0.004/0.016, or 0.25. This is less than the lower solder percentage threshold value of 0.8 so that an insufficient solder defect is reported.

Figure 35A:
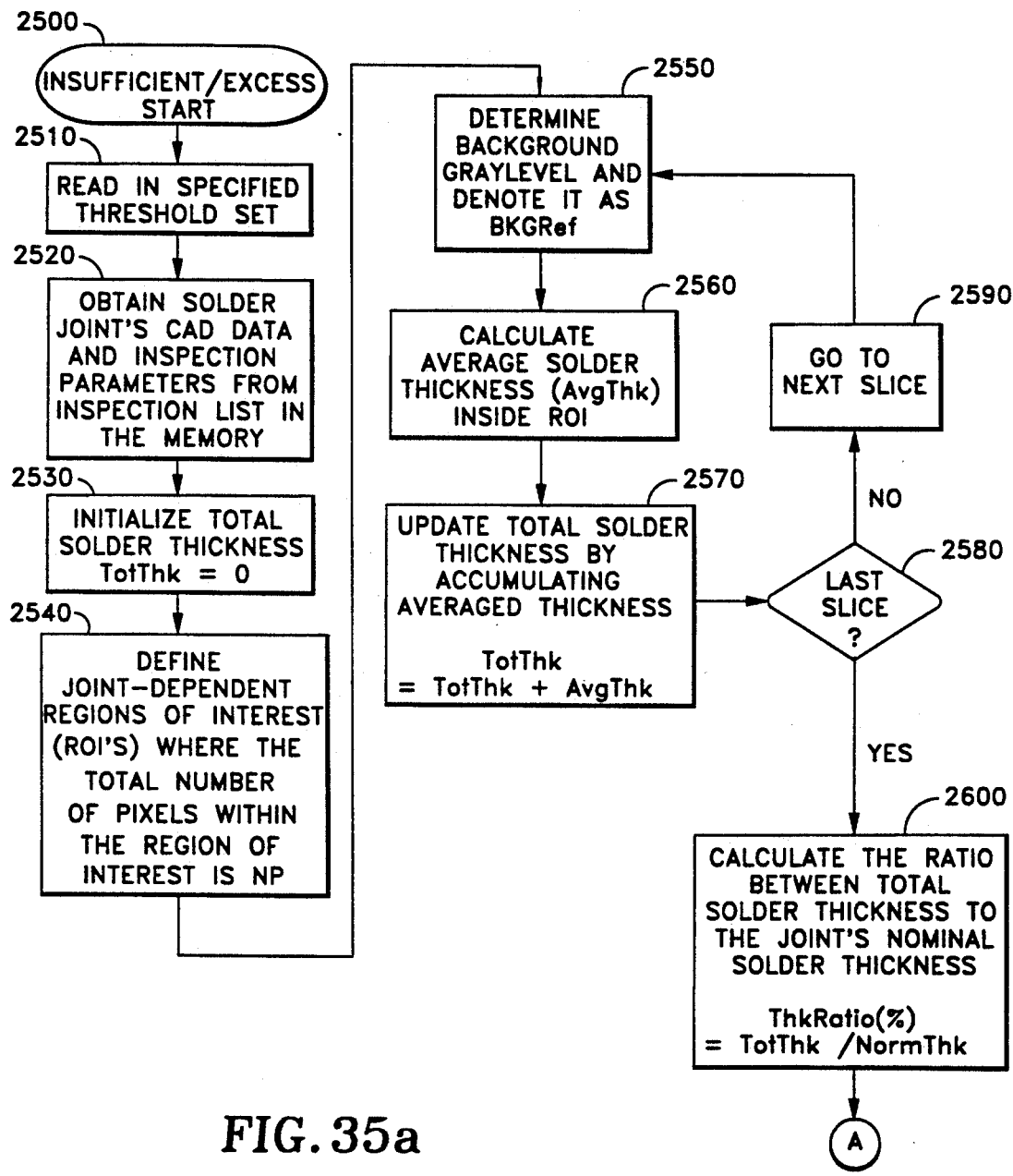
FIGS. 35a and 35b are a flowchart illustrating the process for automatically locating and identifying an excess or insufficient solder defect for solder connections where cross-sectional slices are taken at multiple levels.
Figure 35B:
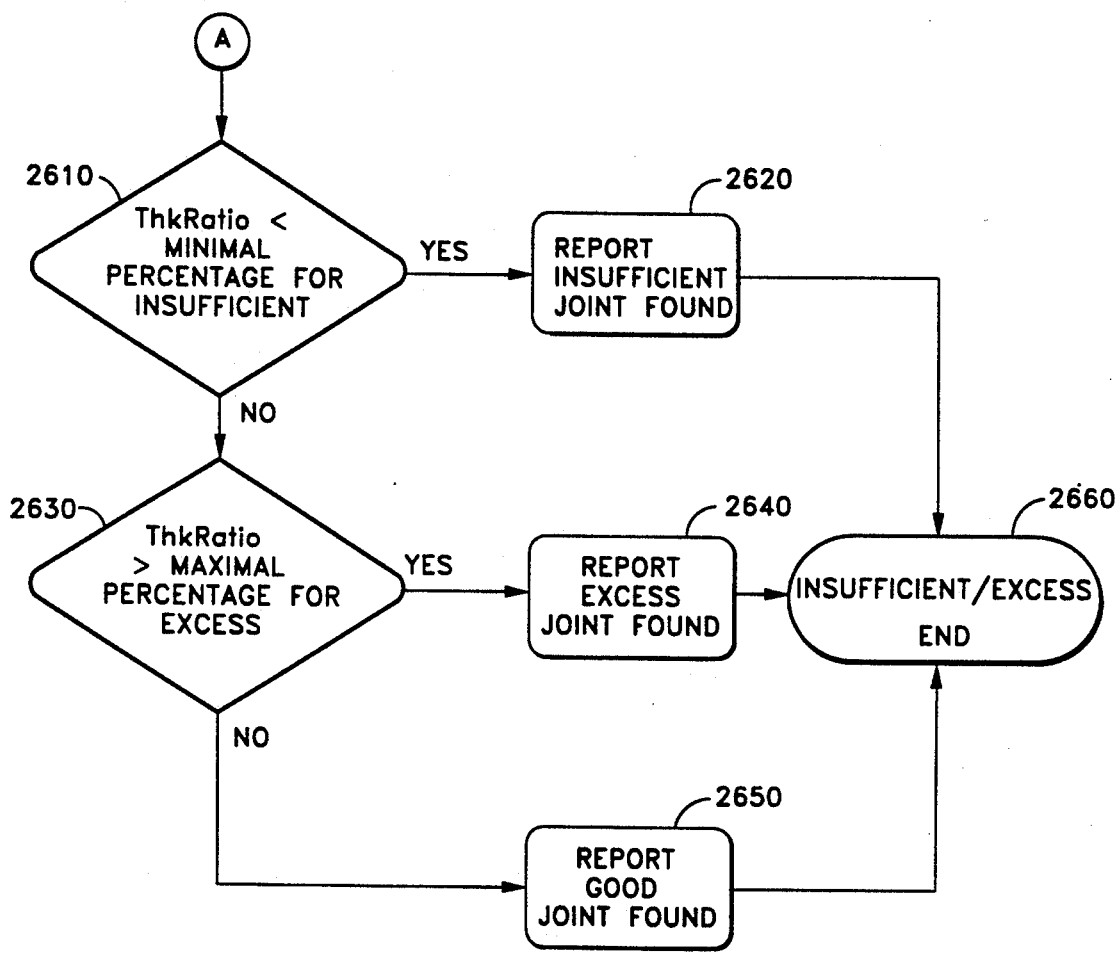

FIGS. 35a and 35b depict a flowchart which details the method of detecting insufficient/excess solder defects modified to take cross-sectional images at multiple levels. The method described in accordance with the flowchart of FIGS. 35a and 35b is similar to the method shown in the flowchart of FIGS. 32a and 32b, with slight modifications made to provide for analysis of multiple levels for a single solder joint. Specifically, a loop comprising a process block 2570, a decision block 2580, and a process block 2590 has been inserted between the subroutine block 2560 and the process block 2600.

The method begins in the process block 2500, and then proceeds to the process blocks 2510 and 2520 wherein the threshold and CAD data are obtained. In the case where multiple slices are to be taken, the threshold data set includes the number of slices (e.g., two) to take for the inspected joint. The method then enters the process block 2530, wherein the total solder thickness value, TotThk, is initialized to zero. The method then proceeds to the process block 2540 wherein a region of interest is defined. Finally, the background intensity value, BKGRef, and the average solder thickness, AvgThick, for the slice at a given level are determined in the process blocks 2550, 2560 respectively.

Once the solder thickness for the designated cross-sectional level has been determined in the subroutine block 2560, the total cumulative solder thickness for the inspected joint is calculated in the process block 2570 by adding the solder thickness obtained in the subroutine block 2560 to the previous total solder thickness value. The method then proceeds to the decision block 2580 which determines if the previous cross-sectional slice is the last cross-sectional slice to be taken.

If the previous cross-sectional slice is not the last slice to be taken, the method enters the process block 2590 wherein a control signal is generated by the master computer 270 to move the positioning table 230 to the next Z-axis inspection level. At the new inspection level, the method proceeds once again into the subroutine block 2550 to determine the background reference value, and subsequently enters the subroutine block 2560 wherein the average solder thickness at the new inspection level is determined. The method then re-enters the process block 2570 wherein the total solder thickness value is updated by adding the previous total solder thickness to the solder thickness of the last inspected level. This cycle continues until all the slice levels have been analyzed.

If the previous cross-sectional slice is the last slice to be analyzed, then the method enters into the process block 2600 wherein the solder thickness percentage ratio is calculated. The method continues into the decision block 2610 to determine if the solder thickness percentage ratio, ThkRatio, is less than the lower solder thickness percentage threshold. If so, an insufficient solder defect is reported in the process block 2620. If ThkRatio is greater than the lower solder thickness ratio, the method enters the decision block 2630 to determine if ThkRatio is greater than the upper solder thickness percentage threshold. If ThkRatio is greater than the upper solder thickness percentage threshold, then an excess solder defect is reported in the process block 2640. If ThkRatio is between the upper and lower solder thickness percentage ratio, a good joint is reported in the process block 2650. Once a joint quality report has been made, the method ends in the process block 2660.

It should be noted that, in the majority of inspection applications, a single cross-sectional slice is sufficient to analyze for solder defects. Some solder joints on LCC and through-hole devices are advantageously inspected with multi-slice views.

Figure 36:
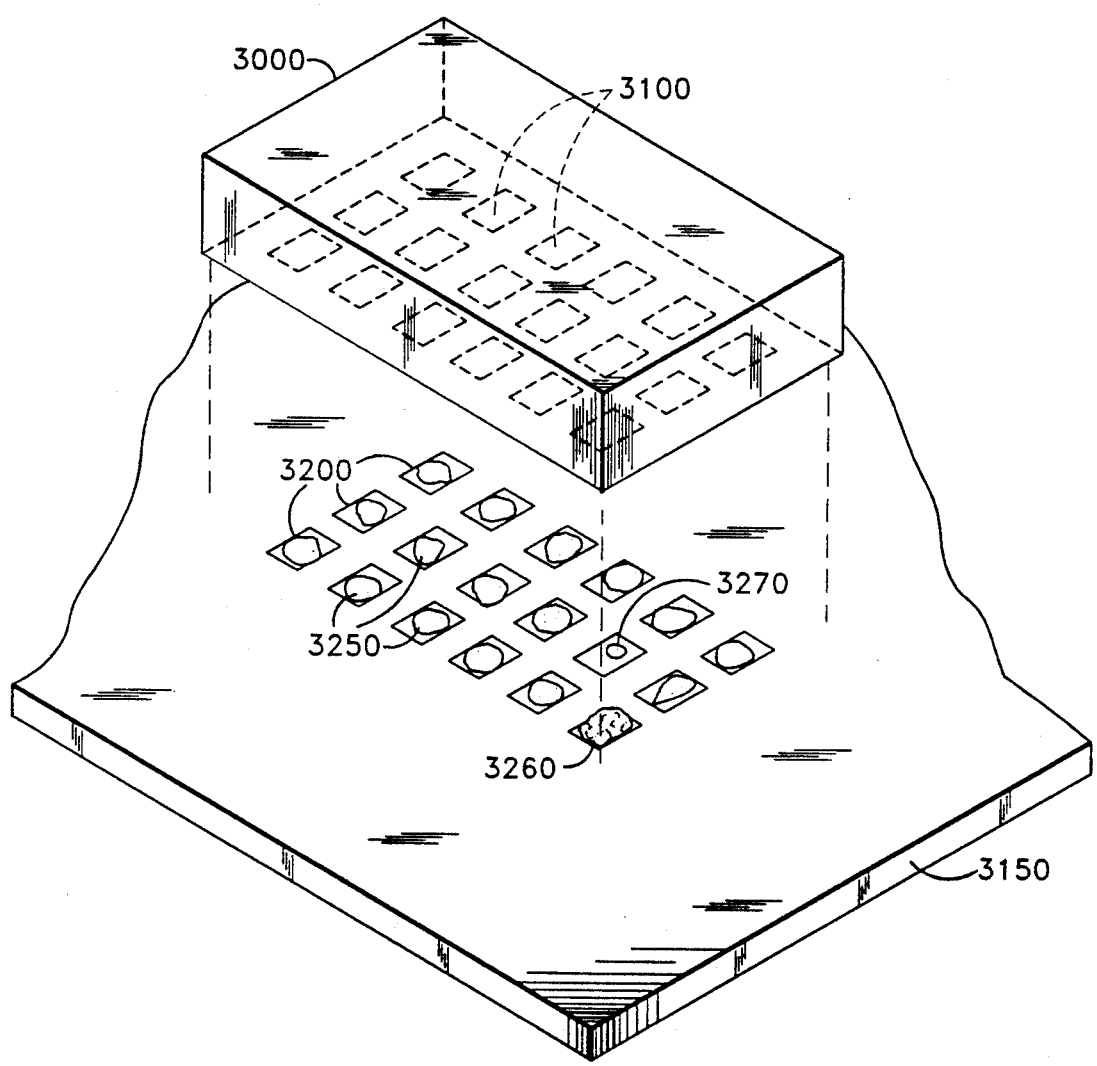
FIG. 36 is a perspective exploded view depicting the manner in which a Flip Chip device is electrically connected to the contact pads on a circuit board.

Although the procedure for detecting insufficient and excess solder defects has been described with reference to a LCC type solder joint, the system and process described above may be applied to other solder joint connection types as well. For example, a leadless surface grid chip, as shown in FIG. 36, commonly referred to as a flip chip, has solder connections which may be analyzed using the above described system and process for detecting insufficient or excess solder. In a flip chip, the contact pads are formed in a grid on the underside of the chip. A corresponding grid of contact pads is provided on the surface of the circuit board. Bumps of solder are formed on the circuit board contact pads. As the contact pad grid on the underside of the flip chip is aligned with the contact pad grid on the surface of the circuit board, and the flip chip is pressed onto the circuit board surface, the solder bumps provide an electrical connection between the contact pads on the circuit board, and the contact pads on the flip chip.

FIG. 36 depicts a flip chip device 3000 having contact pads 3100 on its underside. The flip chip 3000 is mounted onto a circuit board 3150 having contact pads 3200. Also depicted in FIG. 36 are solder bumps 3250 which provide an electrical connection between the contact pads 3100 and the contact pads 3200 so that a solder joint is formed between each pair of contact pads. Note that most of the solder joints to be inspected are hidden so that they cannot be inspected either visually or by using conventional X-ray inspection. By employing the laminography process described herein however, a cross-sectional view at or near the surface of the circuit board 3150 can be taken which allows the solder connections of a flip chip to be analyzed. FIG. 36 further shows a solder bump 3260 having an excess amount of solder, and a solder bump 3270 having an insufficient amount of solder.

Figure 37:
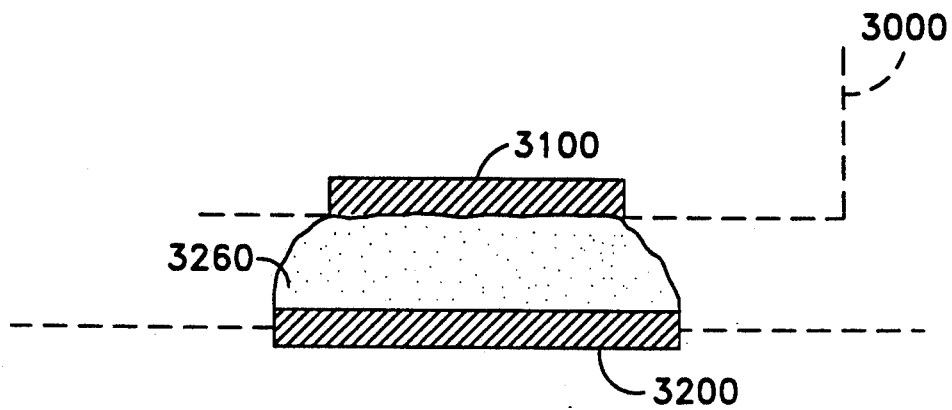
FIG. 37 is a cross-sectional view showing a side slice of an excess solder connection for a Flip Chip device.
Figure 38:
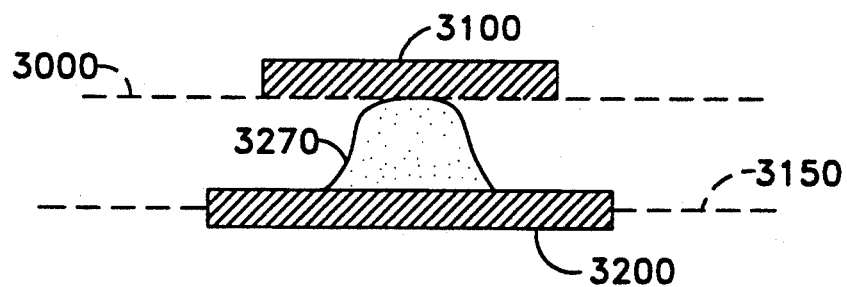
FIG. 38 is a cross-sectional view showing a side slice of an insufficient solder connection for a Flip Chip device.

FIGS. 37 and 38 further illustrate the characteristics of the solder connections 3260 and 3270 made between circuit board contact pads 3200 and the contact pads 3100 of the flip chip 3000. FIG. 37 is a cross-sectional side view of the solder connection 3260 when the flip chip 3000 is positioned onto the circuit board 3150. Note that the solder connection 3260 extends over the entire contact pad region. FIG. 38 is a cross-sectional side view of the solder connection 3270 when the flip chip 3000 is positioned onto the circuit board 3150. Note that the solder connection 3270 extends over a small portion of the contact pad region. In order to detect excess and/or insufficient solder defects for connections on a flip chip device, the method for detecting insufficient and excess solder defects described above may be employed as follows.

Figure 39:
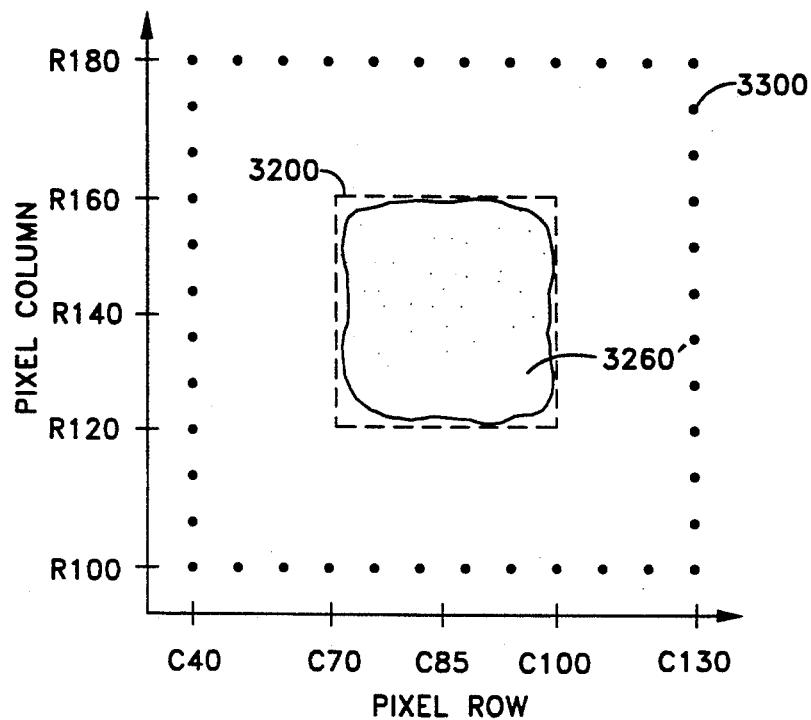
FIG. 39 is a top view cross-sectional slice of an excess solder connection for a Flip Chip device.
Figure 40:
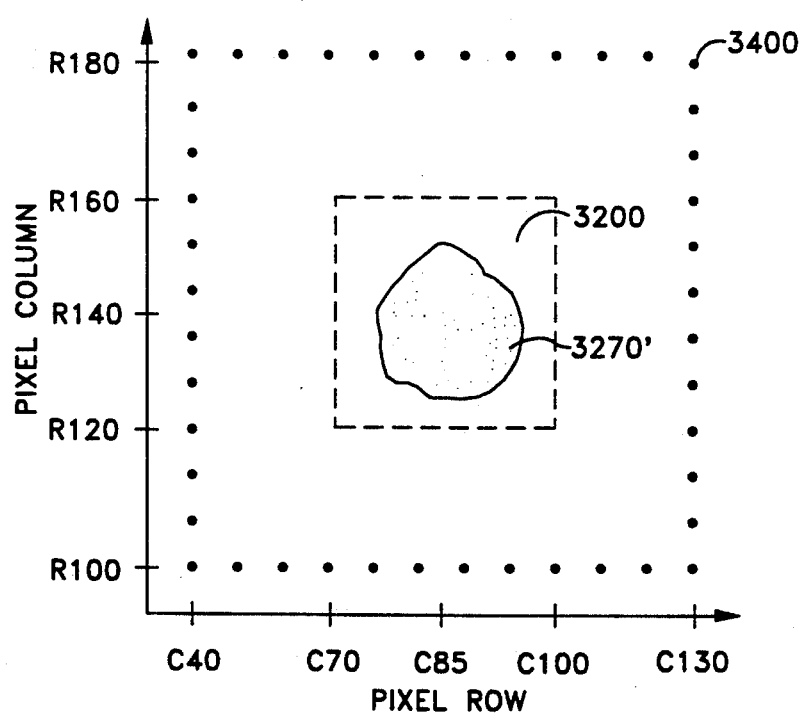
FIG. 40 is a top view cross-sectional slice of an insufficient solder connection for a Flip Chip device.

FIGS. 39 and 40 depict cross-sectional images 3260' and 3270' of the solder connections 3260 and 3270 respectively. The cross-sectional images 3260', 3270' are advantageously taken in a plane which is substantially parallel to the surface of the circuit board 3150, and at a height of 0.0005 inch above the surface of the circuit board 3150. The contact pads 3200 shown in phantom in FIGS. 39 and 40, are shown for reference only, and may not appear in the actual cross-sectional image.

The method for determining excess/insufficient solder defects in the case of the flip chip 3000 is substantially the same as that described in accordance with the flowchart of FIGS. 32a and 32b. As in the case of the LCC solder connection analysis, the method for determining excess/insufficient solder defects first obtains the positional CAD data for the joint to be inspected. After obtaining the CAD data from the data file, a region of interest is then defined which corresponds approximately to the dimensions of the board contact pad 3200.

Note, that the thickness of all the solder joints 3250 is essentially determined by the distance between the flip chip 3000 and the circuit board 210. Thus, a solder joint formed between the board contact pads 3200, and the chip contact pads 3100 will have substantially the same thickness for varying quantities of solder. Thus, if a region of interest is defined to incorporate only the image of an area covered by solder, then the average solder thickness within the defined region of interest may appear the same for an excess and an insufficient solder defect.

In the case of the flip chip device 3000, the contact pads 3200, are made slightly larger than the desired area of solder contact, so that a good solder joint will have solder covering most, but not all, of the pad 3200. Therefore, when the average solder thickness is measured over the entire contact pad region, a good joint will have an average solder thickness which is a little less than the distance between the flip chip 3000 and the circuit board 210. This is because the region of interest is defined to correspond to the dimensions of the pad 3200, and will include regions which do not have solder. Thus, the average image intensity of the entire region of interest will be less than the average image intensity due to the solder joint, and the calculated average solder thickness will be less than the actual average thickness of the solder joint.

The insufficient solder joint 3270 will cover a smaller region of the contact pad 3200 than the region covered by a good solder joint, while the excess solder joint 3260 will cover a larger region of the contact pad 3200 than the region covered by a good solder joint. Thus, when the region of interest is defined to correspond to the boundaries of the contact pad 3200, the average image intensity of an image 3270' produced by the solder joint 3270 will be less than the average image intensity of a good joint. Similarly, when the region of interest is defined to correspond to the boundaries of the contact pad 3200, the average image intensity of an image 3260' produced by the solder joint 3260 will be greater than the average image intensity of a good joint.

When an appropriate region of interest has been defined, the background image intensity local to the inspected solder joint is determined as described above in relation to the flowchart of FIG. 33. For example, in FIG. 39, a background path 3300 is defined around the solder connection image 3260', while in FIG. 40, a background path 3400 is defined around the solder connection image 3270'. The average solder thickness within the region of interest is then determined as described in accordance with the flowchart of FIG. 34. Note that, because the solder connections employed with flip chip devices do not typically exceed 0.020 inch, only one cross-sectional slice is necessary to obtain the total solder thickness of the solder connections 3260, 3270.

Once the average solder thickness within the region of interest is determined, the ratio between the determined solder thickness and the predetermined nominal solder thickness is calculated. This ratio is then compared to an upper threshold value to determine if there is an excess solder defect, and a lower threshold value to determine if there is an insufficient solder defect.

In this manner, the method for detecting excess and insufficient solder defects described above may be used to detect defects in solder connections such as those employed in accordance with a flip chip device. Moreover, the method for detecting excess and insufficient solder defects described herein may be applied to detect excess and insufficient solder defects for other solder joint types. Other types of joints may require some variations in the shape and size of the predefined path and the region of interest. For example the method of the present invention may be used to detect excess and insufficient solder defects in J-lead joint types, gull wing joint types, surface mount pin grid array device joints, spade and radial device through hole joints, axial device through hole joints, and solder joints for capacitive, resistive, and inductive elements.

The system and processes described herein were developed primarily for the inspection of solder connections on printed circuit boards. However, the invention may also be useful for the inspection of other objects and features, for example, regions of metal forming electrical interconnections and circuit traces within the layers of a multilayer board. While the above description comprises embodiments of the invention as applied to the inspection of solder connections between electronic devices on printed circuit boards, there are other applications which will be obvious to those skilled in the art.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A method of detecting an insufficient solder defect comprising the steps of:
   producing a cross-sectional image of a cutting plane of a solder joint;
   analyzing said cross-sectional image to determine the thickness of a portion of said solder joint;
   defining a lower solder thickness threshold value; and
   comparing said thickness to said lower threshold value.

2. A method as defined in claim 1 wherein said analyzing step further comprises the steps of:
   defining a region of interest on said image;
   partitioning said region of interest into a grid of pixels;
   assigning an image intensity value to each of said pixels wherein said image intensity value corresponds to the intensity of the portion of the image represented by each of said pixels;
   calculating an average image intensity value of the pixels within said region of interest; and
   correlating said average image intensity value with a calibration standard.

3. A method of detecting an excess solder defect comprising the steps of:
   producing a cross-sectional image of a cutting plane of a solder joint;
   analyzing said cross-sectional image to determine the thickness of a portion of said solder joint;
   defining an upper solder thickness threshold value; and
   comparing said thickness to said upper threshold value.

4. A method as defined in claim 3 wherein said analyzing step further comprises the steps of:
   defining a region of interest on said image;
   partitioning said region of interest into a grid of pixels;
   assigning an image intensity value to each of said pixels wherein said image intensity value corresponds to the intensity of the portion of the image represented by each of said pixels;
   calculating an average image intensity value of the pixels within said region of interest; and
   correlating said average image intensity value with a calibration standard.

5. A method of measuring the thickness of connective material forming an electrical connection, said method comprising the steps of:
   exposing said connective material to a source of transmissive energy;
   detecting the intensity of said transmissive energy which passes through said material;
   producing a cross-sectional image of a cutting plane of said material with said detected energy;
   defining a region of said cross-sectional image corresponding to a region of said material wherein the thickness of said material is to be determined;
   calculating an average image intensity for said region and
   comparing said average image intensity to a calibration standard which correlates image intensity with material thickness.

6. An apparatus for measuring the thickness of material forming an electrical connection comprising:
   an imaging system for producing a cross-sectional image of a cutting plane of an electrical connection; and
   an image analysis system for analyzing said cross-sectional image to determine the thickness of said material, said image analysis system further comprising:
      means for defining a region of said cross-sectional image corresponding to a region of said material wherein the thickness of said material is to be determined;
      a processor for calculating an average image intensity value for said region; and
      a comparator for comparing said average image intensity value to a calibration standard having a correlation between image intensity and material thickness to obtain the thickness of said material forming said electrical connection.

7. A method of detecting a defect in a solder joint comprising the steps of:
   producing a cross-sectional image of said solder joint wherein said image displays features of said solder joint against a background;
   dividing said cross-sectional image into a pixel grid wherein each of said pixels in said grid has an image intensity value which corresponds to the intensity of said image at the location of said pixel;

defining a region of interest;

determining a background image intensity value of said cross-sectional image, said determining step further including the steps of:
defining a background region; and
calculating an average background value;

subtracting said average background value from the image intensity values of each pixel comprising said region of interest to create a set of background-corrected image intensity values for the pixels comprising said region of interest;

calculating an average of said background-corrected image intensity values for the pixels comprising said region of interest;

providing a calibration standard which correlates image intensity value with solder thickness value; and comparing said average of said background-corrected image intensity value within said region of interest to said calibration standard to determine an average solder thickness value for said region of interest.

8. A method as defined in claim 7 wherein said step of calculating an average background level comprises the steps of:
filtering out pixels within said background region which do not correspond to a part of said background; and
determining an average background value which is equal to the average image intensity value of the pixels within said background region that correspond to a part of said background.

9. A method as defined in claim 8 wherein said filtering step comprises the steps of:
calculating an upper boundary value which is equal to the average image intensity value of all of the pixels within said background region; and
selecting those pixels which have image intensity values that are below said upper boundary value as pixels that correspond to a part of said background.

10. A method as defined in claim 7 further comprising the steps of:
defining a nominal solder thickness value, an upper threshold solder thickness value and a lower threshold solder thickness value;
dividing said average solder thickness value for said region of interest by said nominal solder thickness value to produce a solder thickness ratio value; and
comparing said solder thickness ratio value to said upper threshold value and said lower threshold value.

11. A method for monitoring and controlling a solder application apparatus which forms solder joints, said method comprising the steps of:
producing cross-sectional images of cutting planes of a plurality of solder joints;
determining the thickness of each of said plurality of solder joints;
comparing said determined solder thickness with a nominal solder thickness;
generating a feedback signal in response to said comparison; and
providing said feedback signal to said solder application device.

12. A method as defined in claim 11 wherein said comparing step comprises the step of dividing said determined solder thickness value by said nominal solder thickness value.

13. A method as defined in claim 11 wherein said generating step comprises the steps of:
accessing a predetermined set of response data; and
outputting a control signal from said set of response data.

14. A method as defined in claim 13 wherein said set of response data is programmed into a PROM table.

15. A method as defined in claim 13 wherein said set of response data is programmed into a microprocessor.

16. A method as defined in claim 11, further comprising the step of increasing the solder deposition rate of said solder application device if said determined solder thickness is less than said nominal solder thickness.

17. A method as defined in claim 11, further comprising the step of decreasing the solder deposition rate of said solder application device if said determined solder thickness is greater than said nominal solder thickness.

18. A method for determining, in a digital cross-sectional image of a circuit board, the centroid of an image feature having a predetermined shape, said method comprising the steps of:
defining a pixel template having an inner region, an outer region and a reference pixel; wherein said inner region is of substantially the same shape as said image feature and said outer region substantially surrounds said inner region;
creating a centroid image having a one to one pixel correlation with a portion of said circuit board image containing said image feature, said creating step further comprising the steps of:
a) superimposing said template on said portion of said circuit board image;
b) summing the image intensity values of pixels comprising said circuit board image falling within said inner region of said template;
c) summing the image intensity values of said digital image falling within said outer region of said template;
d) taking the difference of said inner region sum and said outer region sum;
e) defining the intensity of a pixel of said centroid image corresponding to said template reference pixel to be equal to said difference; and
f) repeating steps a) through e) until a substantial number of the pixels comprising said portion of said circuit board image have bee covered by said template reference pixel;
comparing the image intensity values of the pixels comprising said centroid image to locate the pixel having the maximum value; and
defining a pixel of said circuit board image corresponding to said maximum value pixel of said centroid image to be the location of the centroid of said image feature.

19. An apparatus for measuring the thickness of material forming an electrical connection comprising:
an imaging system for producing a cross-sectional image of an electrical connection;
an image analysis system for analyzing said cross-sectional image to determine the thickness of said material, said image analysis system further comprising:
means for defining a region of said cross-sectional image corresponding to a region of said material wherein the thickness of said material is to be determined;

a processor for calculating an average image intensity value for said region;

a means for subtracting a first correction factor from said average image intensity value and setting the resulting difference equal to a first corrected intensity value;

a means for multiplying said first corrected intensity value by a second correction factor, said product equal to a second corrected intensity value; and a comparator for comparing said second corrected intensity value to a calibration standard having a correlation between image intensity value and material thickness.

20. A method of measuring the thickness of material forming a subject electrical connection comprising the steps of:

producing a cross-sectional image of said subject electrical connection;

analyzing said cross-sectional image to determine the thickness of said material, said analyzing step further comprising the steps of:

defining a region of said cross-sectional image corresponding to a region of said material wherein the thickness of said material is to be determined;

calculating an average image intensity value for said region;

subtracting a first correction factor from said average image intensity value and setting the resulting difference equal to a first corrected intensity value;

multiplying said first corrected intensity value by a second correction factor, said product equal to a second corrected intensity value; and comparing said second corrected intensity value to a calibration standard having a correlation between image intensity value and material thickness.

21. A method as defined in claim 20, wherein said first correction factor is equal to the background level of said cross-sectional image.

22. A method as defined in claim 20, wherein said second correction factor is determined by the steps of:

sampling a plurality of electrical connections having a substantially uniform thickness;

determining a background level local to each of said electrical connections;

determining a foreground level for each of said electrical connections, said foreground level being equal to an average image intensity value of said image region corresponding to said electrical connection, minus said background level local to said electrical connection;

correlating said foreground and background levels of said electrical connections;

normalizing said foreground levels with respect to a preselected foreground level, said preselected foreground level being within a range of foreground levels that corresponds to said determined background levels;

determining a background level local to said subject electrical connection; and designating the normalized foreground level which is correlated with said determined background level local to said subject electrical connection as said second correction factor.

23. A method as defined in claim 2, wherein said preselected foreground level is equal to the foreground level corresponding to the lowest of said determined background levels.

24. A method of measuring the volume of connective material forming an electrical connection, said method comprising the steps of:

exposing said connective material to a source of transmissive energy;

detecting the intensity of said transmissive energy which passes through said material;

producing a cross-sectional image of said material with said detected energy;

defining a region of said cross-sectional image corresponding to a region of said material wherein the volume of said material is to be determined, said region having a predetermined area;

calculating an average image intensity for said region;

comparing said average image intensity to a calibration standard which correlates image intensity with material thickness to obtain an average thickness measurement value over said region of interest; and multiplying said obtained average thickness measurement value by said predetermined area of said region of interest to obtain the volume of said connective material.

25. An apparatus for measuring the volume of material forming an electrical connection comprising:

an imaging system for producing a cross-sectional image of a cutting plane of an electrical connection; and an image analysis system for analyzing said cross-sectional image to determine the volume of said material, said image analysis system further comprising:

means for defining a region of said cross-sectional image corresponding to a region of said material wherein the volume of said material is to be determined, said region having a predetermined area;

a processor for calculating an average image intensity value for said region;

a comparator for comparing said average image intensity value to a calibration standard having a correlation between image intensity and material thickness; and a multiplier for calculating the volume of said connective material within said region of interest using said material thickness and said predetermined area.

26. An apparatus for measuring the thickness of material forming an electrical connection comprising:

an imaging system for producing a cross-sectional image of a cutting plane of an electrical connection; and an image analysis system for analyzing said cross-sectional image to determine the thickness of said material, said image analysis system further comprising:

a processor for calculating an average image intensity value for a region of said cross-sectional image corresponding to a region of said material wherein the thickness of said material is to be determined; and a comparator for comparing said average image intensity value to a calibration standard having a correlation between image intensity and material thickness.

27. An apparatus for monitoring and controlling a solder application device which forms solder joints, said apparatus comprising:

a solder joint inspection device which determines the thickness of each of said solder joints wherein said solder joint inspection device comprises:
  an imager that produces cross-sectional images of cutting planes of solder joints; and
  an image analyzer which analyzes said cross-sectional images to determine the thickness of each of said solder joints;
a comparator which compares said determined solder thickness with a nominal solder thickness and provides an output comparison value; and
a controller which receives as input said comparison value and generates a feedback signal which causes said solder application device to increase or reduce the amount of solder deposited onto said solder joints.

28. An apparatus for measuring the thickness of material forming an electrical connection comprising:
  an imaging system for producing a cross-sectional image of an electrical connection; and
  an image analysis system for analyzing said cross-sectional image to determine the thickness of said material, said image analysis system further comprising:
    a processor that calculates an average image intensity value for a region of said cross-sectional image corresponding to a region of said material wherein the thickness of said material is to be determined, said processor further comprising a subtractor which subtracts a first correction factor from said average image intensity value and sets the resulting difference equal to a first corrected intensity value, said processor further comprising a multiplier which multiplies said first corrected intensity value by a second correction factor and sets the resulting product equal to a second corrected intensity value; and
    a comparator that compares said second corrected intensity value to a calibration standard having a correlation between image intensity and material thickness to obtain said material thickness.

29. An apparatus for measuring the volume of material forming an electrical connection comprising:
  an imaging system for producing a cross-sectional image of a cutting plane of an electrical connection; and
  an image analysis system for analyzing said cross-sectional image to determine the volume of said material, said image analysis system further comprising:
    a processor that calculates an average image intensity value for a region of said cross-sectional image corresponding to a region of said material wherein the volume of said material is to be determined, said region having a predetermined area, said processor further comprising a comparator that compares said average image intensity value to a calibration standard having a correlation between image intensity and material thickness, said processor further comprising a multiplier that calculates the volume of said connective material within said region of interest using said material thickness and said predetermined area.

30. A method of detecting an insufficient solder defect comprising the steps of:
  producing a cross-sectional image of a cutting plane of a solder joint;
  analyzing said cross-sectional image to determine the thickness of a portion of said solder joint, said analyzing step further comprising the steps of:
    defining a region of interest on said image;
    partitioning said region of interest into a grid of pixels;
    assigning an image intensity value to each of said pixels wherein said image intensity value corresponds to the intensity of the portion of the image represented by each of said pixels;
    calculating an average image intensity value of the pixels within said region of interest; and
    correlating said average image intensity value with a calibration standard; defining a lower solder thickness threshold value; and comparing said thickness to said lower threshold value.

31. A method of detecting an excess solder defect comprising the steps of:
  producing a cross-sectional image of a cutting plane of a solder joint;
  analyzing said cross-sectional image to determine the thickness of a portion of said solder joint, said analyzing step further comprising the steps of:
    defining a region of interest on said image;
    partitioning said region of interest into a grid of pixels;
    assigning an image intensity value to each of said pixels wherein said image intensity value corresponds to the intensity of the portion of the image represented by each of said pixels;
    calculating an average image intensity value of the pixels within said region of interest; and
    correlating said average image intensity value with a calibration standard; defining an upper solder thickness threshold value; and comparing said thickness to said upper threshold value.

* * * * *